US012649937B2

(12) United States Patent
Schirmer et al.

(10) Patent No.: US 12,649,937 B2
(45) Date of Patent: Jun. 9, 2026

(54) PRODUCTION OF NON-NATIVE MONOUNSATURATED FATTY ACIDS IN BACTERIA

(71) Applicant: Genomatica, Inc., San Diego, CA (US)

(72) Inventors: Andreas W. Schirmer, San Diego, CA (US); Erin Frances Perry, San Marcos, CA (US); Alma Itzel Ramos-Solis, San Diego, CA (US); Angelica Zabala-Bautista, San Diego, CA (US)

(73) Assignee: GENOMATICA, INC., San Diego, CA (US)

( * ) Notice: Subject to any disclaimer, the term of this patent is extended or adjusted under 35 U.S.C. 154(b) by 336 days.

(21) Appl. No.: 18/284,349

(22) PCT Filed: Mar. 22, 2022

(86) PCT No.: PCT/US2022/021290
§ 371 (c)(1),
(2) Date: Sep. 27, 2023

(87) PCT Pub. No.: WO2022/212119
PCT Pub. Date: Oct. 6, 2022

(65) Prior Publication Data
US 2024/0229086 A1 Jul. 11, 2024

Related U.S. Application Data

(60) Provisional application No. 63/167,355, filed on Mar. 29, 2021.

(51) Int. Cl.
| | |
|---|---|
| *C12N 1/20* | (2026.01) |
| *C12N 9/02* | (2006.01) |
| *C12N 9/04* | (2006.01) |
| *C12N 9/10* | (2006.01) |
| *C12N 9/12* | (2006.01) |
| *C12N 9/16* | (2006.01) |
| *C12N 9/88* | (2006.01) |
| *C12P 7/6409* | (2022.01) |

(52) U.S. Cl.
CPC .............. *C12P 7/6409* (2013.01); *C12N 1/20* (2013.01); *C12N 9/0006* (2013.01); *C12N 9/0008* (2013.01); *C12N 9/0071* (2013.01); *C12N 9/1029* (2013.01); *C12N 9/1288* (2013.01); *C12N 9/16* (2013.01); *C12N 9/88* (2013.01); *C12Y 101/01001* (2013.01); *C12Y 102/0103* (2013.01); *C12Y 114/19002* (2013.01); *C12Y 118/01002* (2013.01); *C12Y 203/01084* (2013.01); *C12Y 207/08007* (2013.01); *C12Y 301/02014* (2013.01); *C12Y 402/01059* (2013.01)

(58) Field of Classification Search
CPC .......... C12N 9/10; C12N 9/1029; C12N 9/00; C12N 9/88; C12P 7/6409
See application file for complete search history.

(56) References Cited

U.S. PATENT DOCUMENTS

| | | | |
|---|---|---|---|
| 6,255,276 | B1 | 7/2001 | Frater et al. |
| 9,481,899 | B2 | 11/2016 | Schirmer et al. |
| 9,587,231 | B2 | 3/2017 | Hom et al. |
| 9,598,706 | B2 | 3/2017 | Keasling et al. |
| 9,670,512 | B2 | 6/2017 | Schirmer et al. |
| 9,683,219 | B2 | 6/2017 | Rude et al. |
| 9,683,247 | B2 | 6/2017 | Lutes et al. |
| 9,758,769 | B2 | 9/2017 | Greenfield et al. |
| 9,873,865 | B2 | 1/2018 | Rude et al. |
| 9,879,239 | B2 | 1/2018 | Shumaker et al. |
| 9,890,401 | B2 | 2/2018 | Hu et al. |
| 9,951,322 | B2 | 4/2018 | Hom et al. |
| 12,221,644 | B2 * | 2/2025 | Schirmer ....... C12Y 402/01059 |
| 2010/0298612 | A1 | 11/2010 | Behrouzian et al. |
| 2015/0050708 | A1 | 2/2015 | Burgard et al. |
| 2016/0130616 | A1 | 5/2016 | Schirmer et al. |
| 2019/0136272 | A1 | 5/2019 | Otte et al. |

FOREIGN PATENT DOCUMENTS

| | | |
|---|---|---|
| WO | 2009111513 A1 | 9/2009 |
| WO | WO-2010/062480 A2 | 6/2010 |
| WO | WO-2013152052 A2 | 10/2013 |

(Continued)

OTHER PUBLICATIONS

Partial Supplementary Search Report from EP Application No. 22781894.5 dated Sep. 17, 2025.
Wang et al (2004). *Functional replacement of the FabA and FabB proteins of Escherichia coli fatty acid synthesis by Enterococcus faecalis FabZ and FabF homologues.* J. Biol. Chem, 279(33): 34489-34495.
International Search Report from PCT Application No. PCT/US2022/02190 dated Jul. 17, 2022.
Written Opinion from PCT Application No. PCT/US2022/21290 dated Aug. 30, 2022.

(Continued)

*Primary Examiner* — Tekchand Saidha
(74) *Attorney, Agent, or Firm* — Harness Dickey & Pierce P.L.C.

(57) ABSTRACT

Recombinant proteobacteria, including γ-proteobacteria, comprising a heterologous acyl-ACP desaturase and a heterologous acyl-ACP thioesterase, wherein the native dual 3-hydroxy acyl-ACP dehydratase/isomerase is deleted are provided herein. The recombinant proteobacteria produce non-native monounsaturated free fatty acids or derivatives thereof. Methods of producing non-native monounsaturated free fatty acids or derivatives thereof are also provided, in addition to cell cultures and fatty acid compositions produced by the recombinant proteobacteria. The recombinant proteobacteria may be used to produce insect pheromones or precursors thereof, and fragrances or precursors thereof.

17 Claims, 8 Drawing Sheets
Specification includes a Sequence Listing.

(56)　　　　　References Cited

FOREIGN PATENT DOCUMENTS

| WO | WO-2014201474 A1 | 12/2014 |
| WO | WO-2015157719 A9 | 10/2015 |
| WO | WO-2016207339 A1 | 12/2016 |
| WO | WO-2017087846 A1 | 5/2017 |
| WO | 2017214133 A2 | 12/2017 |
| WO | WO-2018109163 A1 | 6/2018 |
| WO | WO-2018109167 A1 | 6/2018 |
| WO | WO-2020047088 A1 | 3/2020 |

OTHER PUBLICATIONS

Magnuson et al. (1993). *Regulation of fatty acid biosynthesis in Escherichia coli.* Appl. Microbial Rev, 57(3):522-542.

Schultz et al. (1996). *Expression of a delta 9 14:0-acyl carrier protein fatty acid desaturase gene is necessary for the production of omega 5 anacardic acids found in pest-resistant geranium (Pelargonium xhortorum.* PNAS, 16: 8771-9775.

Cahoon & Shanklin (2000). *Substrate-dependent mutant complementation to select fatty acid desaturase variants for metabolic engineering of plant seed oils.* PNAS, 97: 121350-12355.

Heath & Rock (1996). *Roles of the FabA and FabZ β-Hydroxyacyl-Acyl Carrier Protein Dehydratases in Escherichia coli Fatty Acid Biosynthesis.* J. Biol. Chem, 271: 27795-27801.

Yuan et al. (1994). *Modification of the substrate specificity of an acyl-acyl carrier protein thioesterase by protein engineering.* PNAS, 92: 10639-10643.

Jing et al. (2011). *Phylogenetic and experimental characterization of an acyl-ACP thioesterase family reveals significant diversity in enzymatic specificity and activity.* BMC. Biochem, 12: 44.

Tupec et al. (2017). *Biotechnological potential of insect fatty acid-modifying enzymes.* Z. Naturforsch, 72: 387-403.

Lindquist et al. (1996). *Crystal structure of delta9 stearoyl-acyl carrier protein desaturase from castor seed and its relationship to other di-iron proteins.* EMBO J, 15: 4081-4092.

Johnson & Greenberg (1975). *Mapping of sul, the suppressor of lon in Escherichia coli.* J. Bacteriol, 122: 570-574.

Nettleton J.A (2016). *Dietary Fatty Acids: Is it Time to Change the Recommendations.* Ann Nutr Metab, 68:249-257.

Rosano & Ceccarelli (2014). *Recombinant protein expression in Escherichia coli: advances and challenges.* Front Microbial, 5: 172.

Yujin Cao et al. (2014). *Production of free monounsaturated fatty acids by metabolically engineered Escherichia coli.* Biotechnol Biofuels.; 7: 59.

Campbell & Cronan (2001). *Escherichia coli FadR Positively Regulates Transcription of the fabB Fatty Acid Biosynthetic Gene.* J. Bacteriol. 183: 5982-5990.

Zhang et al. (2008). *Membrane lipid homeostasis in bacteria.* Nature Rev.6: 222-233.

Winkler (2018). *Carboxylic acid reductase enzymes (CARs).* Cur. Op. Chem. Biol. 43: 23-29.

My et al. (2015). *Reassessment of the genetic regulation of fatty acid synthesis in E. coli.* J. Bacteriol. 197: 1862-1872.

* cited by examiner

Chemical Formula: $C_{13}H_{27}O_2SSi^{\bullet}$
Exact Mass: 275.15

Chemical Formula: $C_6H_{13}S^{\bullet}$
Exact Mass: 117.07

Fig. 3A trimethylsilyl 11,12-bis(methylthio)hexadecanoate
Molecular Weight: 420.79

Chemical Formula: $C_{15}H_{31}O_2SSi^*$
Exact Mass: 303.18
Molecular Weight: 303.56

Chemical Formula: $C_6H_{13}S^*$
Exact Mass: 117.07
Molecular Weight: 117.23

PRODUCTION OF NON-NATIVE MONOUNSATURATED FATTY ACIDS IN BACTERIA

CROSS REFERENCE TO RELATED PATENT APPLICATIONS

This application is a national stage application under 35 U.S.C. § 371 of PCT International Application No. PCT/US2022/021290, which has an international filing date of 22 Mar. 2022 and claims the domestic benefit of U.S. Provisional Patent Application No. 63/167,355. The contents of each application recited above are incorporated herein by reference in their entirety.

REFERENCE TO A SEQUENCE LISTING

This application contains references to amino acid sequences and/or nucleic acid sequences which have been submitted concurrently herewith as the sequence listing text file entitled "6281099_1.TXT", file size 93 KiloBytes (KB), created on 14 Mar. 2022. The aforementioned sequence listing is hereby incorporated by reference in its entirety pursuant to 37 C.F.R. § 1.52(e)(5).

FIELD

The disclosure relates to the field of specialty chemicals and methods for their synthesis. The disclosure provides proteobacteria engineered to produce non-native monounsaturated fatty acids and derivatives thereof. The disclosure further provides biochemical pathways, recombinant microorganisms and methods for the biological production of various monounsaturated free fatty acids and derivatives thereof.

BACKGROUND

Monounsaturated fatty acids (mUFAs) and fatty acid derivatives are attractive as the basis for many different products. For example, mUFAs are a component of good nutrition (see e.g., Nettleton J. A (2016) Ann Nutr Metab. 68:249-257); they serve as the basis for production of numerous useful molecules such as e.g., flavors and fragrances (see e.g., International Patent Application Publication WO 2016/157719). Production of musk fragrance precursors from native mUFA derivatives (e.g., musk macrolactone cis-isoambrettolide) or from non-native ω-9 mUFA derivatives (e.g., musk macrolactone ambrettolide) have been described. See WO 2014/201474 and WO 2020/047088, both incorporated herein by reference in their entirety.

Additionally, mUFAs are also ideal components for biodiesel since mUFAs improve fluidity at low temperatures and contribute to oxidative stability of the biodiesel product (see e.g., Yujin Cao et al. (2014) Biotechnol Biofuels.; 7: 59).

Most sources of mUFAs for nutrition, biodiesel, and for flavor and/or fragrance chemicals depend on plant or animal origins and thus can be limited in both quantity and quality.

In recent years, technology for the production of fatty acids and fatty acid derivatives has been successfully developed see e.g., U.S. Pat. Nos. 9,951,322; 9,890,401; 9,879,239; 9,873,865; 9,758,769; 9,683,247; 9,683,219; 9,670,512; 9,598,706; 9,587,231; 9,481,899 (each of which is incorporated herein by reference in its entirety). It would be greatly beneficial to be able to use such technology for the industrial scale production of mUFAs and fatty acid derivatives. In particular, it would be greatly beneficial to use recombinant proteobacteria to prepare mUFAs and fatty acid derivatives.

Recombinant proteobacteria possess many advantages over other microorganisms for the industrial production of fatty acid derivatives (see e.g., Front Microbiol. 2014; 5: 172). Despite the advantages, there are drawbacks when it comes to the production of mUFAs and fatty acid derivatives. As is well known in the art, most proteobacteria, such as E. coli, incorporate double bonds into mUFAs between the seventh and eighth carbon counting from the reduced end of the carbon chain (i.e., at the omega-7 (ω-7) position). Thus, the production of monounsaturated fatty acids having double bonds in e.g., the ω-3, ω-5, ω-6, ω-8, ω-9, ω-11, ω-12, etc. positions are non-native to most proteobacteria.

Most proteobacteria incorporate double bonds in the ω-7 position of mUFAs through the paradigmatic "oxygen independent" (anaerobic) mUFA biosynthetic pathway (see e.g., Magnuson et al. (1993) Appl. Microbial Rev. 57(3):522-542). E. coli has two 3-hydroxy acyl-ACP dehydratases, FabZ and FabA. The key enzyme for mUFA synthesis is FabA, which is a dual function dehydratase/isomerase. FabA isomerizes trans-2-decenoyl-ACP to cis-3-decenoyl-ACP. The latter cannot be reduced by trans-2-enoyl-ACP reductase (FabI), but can be elongated by R-keto-acyl-ACP synthase I (FabB) thereby fixing the double bond position in the ω-7 position (see e.g., FIG. 1). FabA is very specific for isomerizing trans-2-decenoyl-ACP leading to the predominant production of ω-7 mUFAs in these proteobacteria.

Therefore, with regard to the synthesis of diverse mUFAs, manufacturers who desire to produce mUFAs having a double bond in a position other than the ω-7 position and who desire to harness the advantages and power of a bacterial platform are faced with a conundrum. Proteobacteria, which can produce mUFAs on an industrial scale, generally produce mUFAs with a double bond in the ω-7 position of the fatty acid. Thus, wild-type proteobacteria are limited in the breadth of mUFAs they can produce.

Consequently, new methods are needed for the production of mUFA molecules that allow for the production of a full spectrum of mUFA molecules, including, but not limited to, mUFAs with double bonds in non-native positions, such as ω-3, ω-5, ω-6, ω-8, ω-9, ω-11, ω-12, etc.

SUMMARY

Disclosed herein are recombinant proteobacteria comprising an acyl-ACP desaturase and an acyl-ACP thioesterase, one or both which may be heterologous, wherein a native dual 3-hydroxy acyl-ACP dehydratase/isomerase (FabA) is deleted or attenuated, and wherein the recombinant proteobacterium produces a non-native mUFA or a derivative thereof. In various embodiments, the recombinant proteobacteria further comprises one or more additional enzymes such as a ferredoxin, a ferredoxin reductase, and/or a flavodoxin reductase, a 3-hydroxyacyl-ACP-dehydratase (FabZ), a carboxylic acid reductase, an alcohol dehydrogenase, a phosphopantetheinyl transferase, an alcohol acetyl-CoA transferase, a ω-hydroxylase, an alcohol oxidase/dehydrogenase, a fatty acid metabolism regulator protein (fadR), a aldehyde hydrogenase, and a β-ketoacyl-ACP synthase, wherein one or more of the additional enzymes are heterologous. In some recombinant proteobacteria comprising an acyl-ACP desaturase and an acyl-ACP thioesterase, the recombinant proteobacteria further comprise a heterologous dual 3-hydroxy acyl-ACP dehydratase/isomerase (FabA).

The recombinant proteobacterium may be a γ-proteobacterium, such as *Escherichia coli*. The recombinant proteobacterium may produce one or more non-native mUFAs, including, but not limited to, mUFAs having a double bond at the ω-3, ω-5, ω-6, ω-9, ω-11, ω-12, or other position.

Also disclosed herein are methods for producing a non-native mUFA or a derivative thereof, said method comprising culturing a recombinant proteobacterium comprising a heterologous acyl-ACP desaturase and a heterologous acyl-ACP thioesterase, wherein the native dual 3-hydroxy acyl-ACP dehydratase/isomerase (FabA) is deleted or attenuated.

Also disclosed herein are nucleotide sequences encoding one or both of a heterologous acyl-ACP desaturase and/or a heterologous acyl-ACP thioesterase, which is operably linked to one or more heterologous regulatory elements. The nucleotide sequence may be in a vector.

Also disclosed herein are insect pheromones and insect pheromone precursors comprising the non-native mUFAs or derivatives thereof produced by the disclosed recombinant proteobacteria comprising a heterologous acyl-ACP desaturase and a heterologous acyl-ACP thioesterase, wherein a native dual 3-hydroxy acyl-ACP dehydratase/isomerase (FabA) is deleted or attenuated and a method for preparing the insect pheromones or insect pheromone precursors.

Also disclosed herein are fragrances and fragrance precursors comprising the non-native mUFAs or derivatives thereof produced by the disclosed recombinant proteobacteria comprising a heterologous acyl-ACP desaturase and a heterologous acyl-ACP thioesterase, wherein a native dual 3-hydroxy acyl-ACP dehydratase/isomerase (FabA) is deleted or attenuated and a method for preparing the fragrances or fragrance precursors.

Also disclosed herein is the use of the recombinant proteobacterium comprising a heterologous acyl-ACP desaturase and a heterologous acyl-ACP thioesterase, wherein a native dual 3-hydroxy acyl-ACP dehydratase/isomerase (FabA) is deleted or attenuated for producing an insect pheromone, insect pheromone precursor, fragrance, and/or fragrance precursor.

Also disclosed herein are compositions comprising more ω-5 unsaturated fatty acid derivatives than ω-7 unsaturated fatty acid derivatives. The compositions may be produced by the recombinant proteobacterium disclosed herein. For example, a composition may comprise more ω-5 unsaturated fatty alcohols than ω-7 unsaturated fatty alcohols, e.g. about 90% of ω-5 unsaturated and about 10% ω-7 unsaturated fatty alcohols (e.g. about 80% of z11-hexadecenol and about 10% of z13-octadecenol and about 10% of z9-hexadecenol).

BRIEF DESCRIPTION OF THE DRAWINGS

Figure 3A:
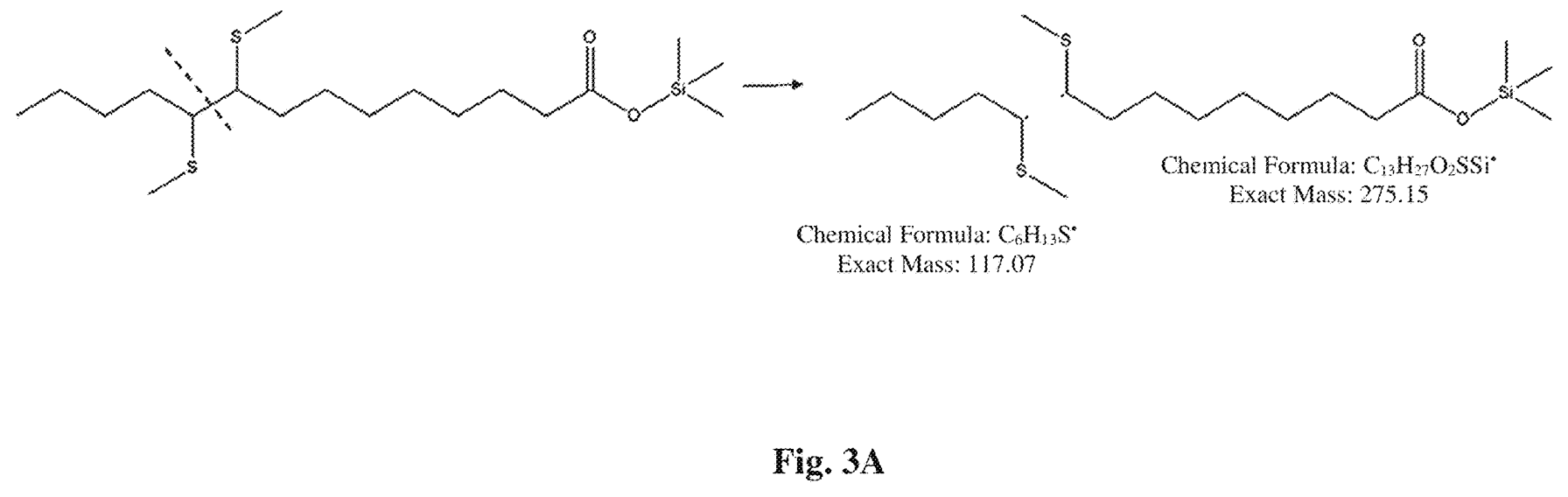

FIG. 3A depicts a fragmentation of ω-5 Δ9-tetradecenoic acid after derivatization by dimethyl disulfide (DMDS).

4

Figure 4A:
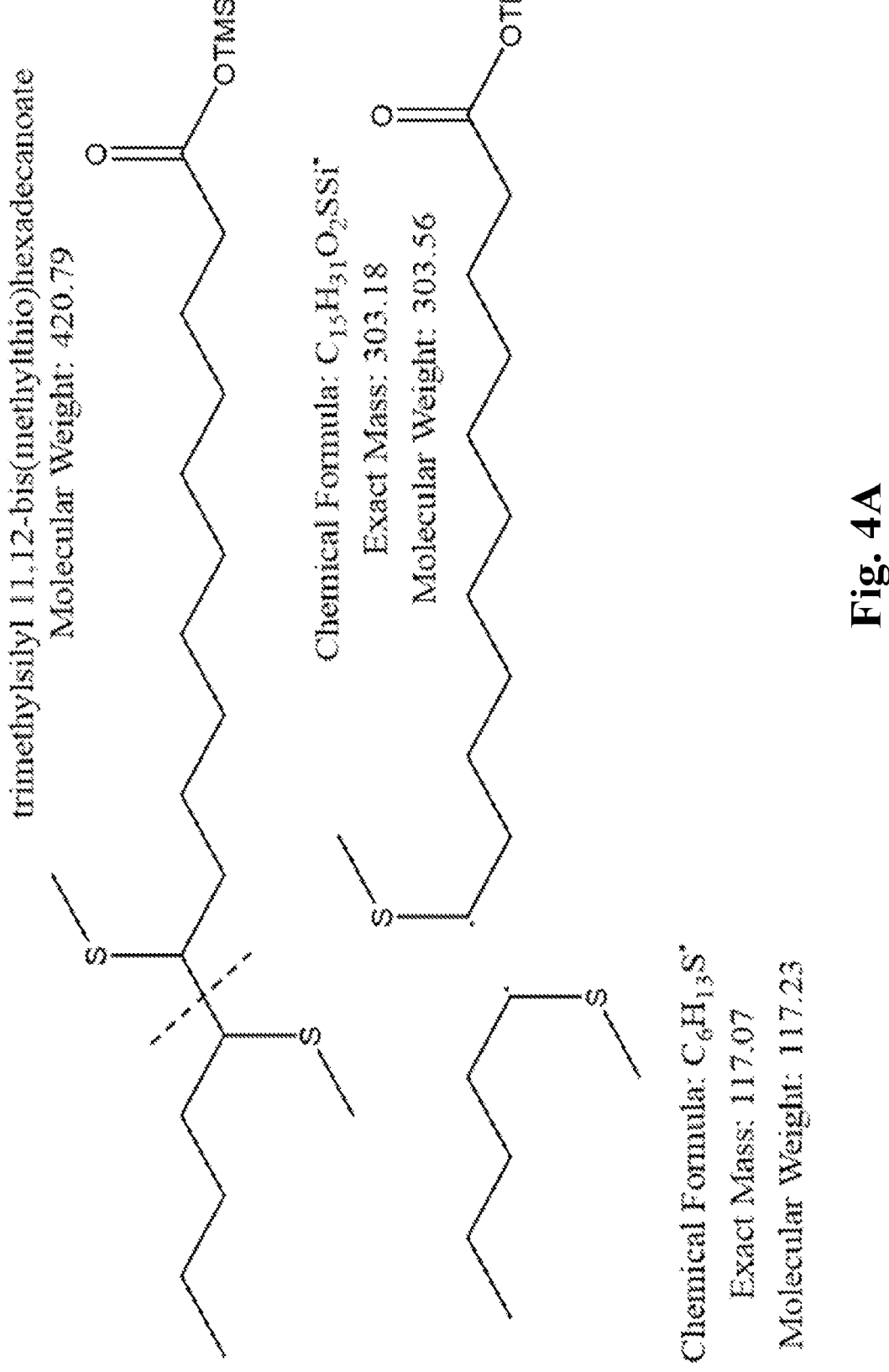
FIG. 4A depicts a fragmentation of ω-5 Δ11-hexadecenoic acid after derivatization by DMDS.
Figure 4B:
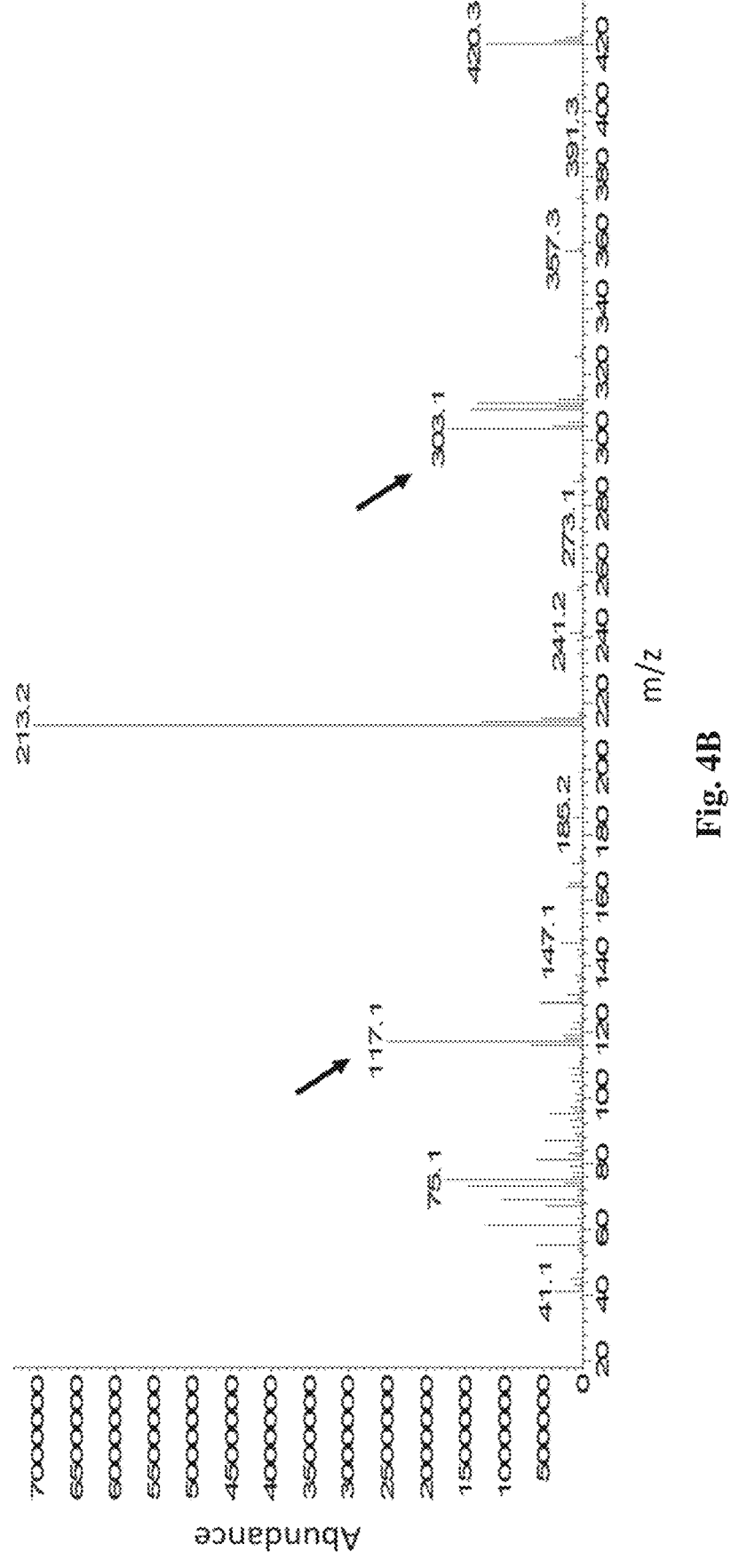

FIG. 4B depicts the mass spectrum and ion fragmentation pattern of ω-5 Δ11-hexadecenoic acid after derivatization DMDS.

Figure 5A:
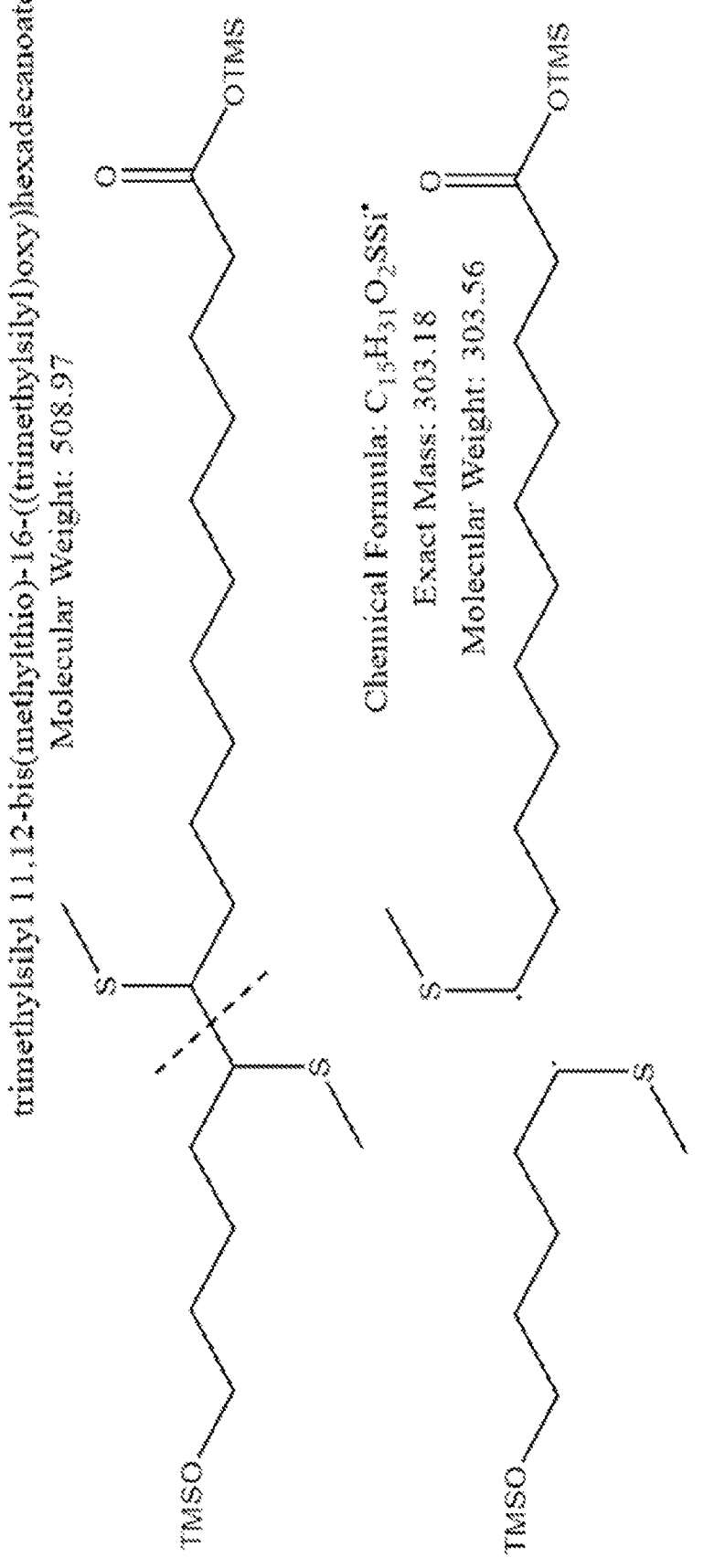

FIG. 5A depicts a fragmentation of ω-5 (z11)16-hydroxy-hexadecenoic acid after by derivatization DMDS.

Figure 5B:
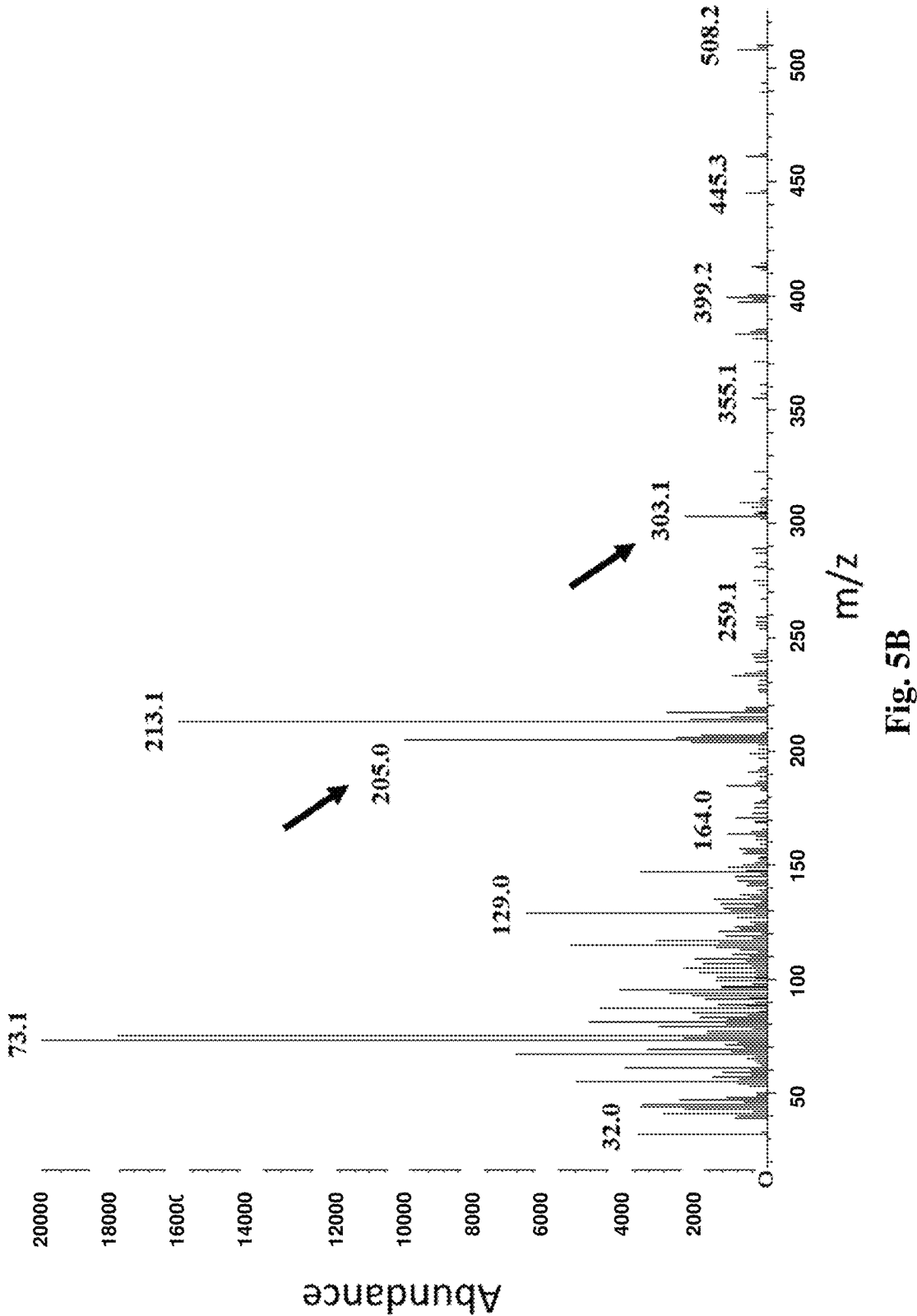

FIG. 5B depicts the mass spectrum and ion fragmentation pattern of ω-5 z11-16-hydroxy-hexadecenoic acid after derivatization DMDS.

DETAILED DESCRIPTION

I. Definitions

The following definitions refer to the various terms used above and throughout the disclosure.

As used herein, singular articles such as "a" and "an" and "the" and similar referents in the context of describing the elements are to be construed to cover both the singular and the plural, unless otherwise indicated herein or clearly contradicted by context.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

As will be understood by one skilled in the art, for any and all purposes, all ranges disclosed herein also encompass any and all possible subranges and combinations of subranges thereof. Furthermore, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Unless defined otherwise, technical and scientific terms used herein have the same meaning as commonly understood by a person of ordinary skill in the art. In particular, this disclosure utilizes routine techniques in the field of recombinant genetics, organic chemistry, fermentation and biochemistry.

The term "fatty acid" as used herein, refers to an aliphatic carboxylic acid having the formula RCOOH wherein R is an aliphatic group having at least 4 carbons, typically between about 4 and about 28 carbon atoms. The aliphatic R group can be saturated or unsaturated, branched or unbranched. Branched aliphatic R groups may include branches comprising lower alkyl branches, such as a C1-C4 alkyl, preferably in the ω-1 or ω-2 position. In some embodiments, the branched aliphatic R group may be methyl in the ω-1 or ω-2 position. Unsaturated fatty acids may be monounsaturated or polyunsaturated.

The fatty acid or fatty acids, as used herein, can be produced within a cell through the process of fatty acid biosynthesis, through the reverse of fatty acid degradation or beta-oxidation (β-oxidation), or they can be fed to a cell. As is well known in the art, fatty acid biosynthesis is generally a malonyl-CoA dependent synthesis of acyl-ACPs or acyl CoAs, while the reverse of beta-oxidation results is acetyl-CoA dependent and results in the synthesis of acyl-CoAs. Fatty acids fed to cell are converted to acyl-CoAs and can be converted to acyl-ACPs. Fatty acids can be synthesized in a cell by natural fatty acid biosynthetic pathways or can be synthesized from heterologous fatty acid biosynthetic pathways that comprise a combination of fatty acid biosynthetic and/or degradation enzymes that result in the synthesis of acyl-CoAs and/or Acyl-ACPs.

The term "fatty acid derivative" as used herein, refers to a product derived from a fatty acid. Thus, a fatty acid derivative is a compound that includes a fatty acid as defined above with a modification. In general, fatty acid derivatives include malonyl-CoA derived compounds including acyl-ACP or acyl-ACP derivatives. Thus, a fatty acid derivative includes alkyl-thioesters and acyl-thioesters. Further, a fatty acid derivative includes a molecule/compound that is derived from a metabolic pathway that includes a fatty acid derivative enzyme. Exemplary fatty acid derivatives include fatty acids, fatty acid esters (e.g., waxes), fatty acid methyl esters (FAME), fatty acid ethyl esters (FAEE)), fatty alcohol acetate esters (FACE), fatty amines, fatty aldehydes, fatty alcohols, hydrocarbons (e.g., alkanes, alkenes, etc.), ketones, terminal olefins, internal olefins, 3-hydroxy fatty acid derivatives, bifunctional fatty acid derivatives (e.g., ω-hydroxy fatty acids, (ω-1)-hydroxy fatty acids, (ω-2)-hydroxy fatty acids, (ω-3)-hydroxy fatty acids, 10-hydroxy fatty acids, 1,3 fatty-diols, α,ω-diols, α,ω-3-hydroxy triols, ω-hydroxy FAME, ω-OH FAEE, etc.), and unsaturated fatty acid derivatives, including unsaturated compounds of each of the above mentioned fatty acid derivatives.

The expression "fatty acid composition" as used herein, refers to a composition of mUFAs or derivatives thereof, for example a fatty acid composition produced by recombinant proteobacterium described herein, such as a recombinant proteobacterium comprising an acyl-ACP desaturase and an acyl-ACP thioesterase, wherein the native dual 3-hydroxy acyl-ACP dehydratase/isomerase is deleted. A fatty acid derivative composition may comprise a single fatty acid derivative species or may comprise a mixture of fatty acid derivative species. In some exemplary embodiments, the mixture of fatty acid derivatives includes more than one type of fatty acid derivative product (e.g., fatty acids, fatty acid esters, fatty alcohols, fatty alcohol acetates, fatty aldehydes, fatty amine, bifunctional fatty acid derivatives, and non-native monounsaturated fatty acid derivatives, etc.). In other exemplary embodiments, the mixture of fatty acid derivatives includes a mixture of non-native monounsaturated fatty acid esters (or another fatty acid derivatives) with different chain lengths, saturation and/or branching characteristics. In other exemplary embodiments, the mixture of fatty acid derivatives comprises predominantly one type of fatty acid derivative e.g., an ω-3-monounsaturated fatty acid or fatty acid derivative composition, an ω-5-monounsaturated fatty acid or fatty acid derivative composition, an ω-11-monounsaturated fatty acid or fatty acid derivative composition, etc. In still other exemplary embodiments, a fatty acid derivative composition comprises a mixture of more than one type of fatty acid derivative product e.g., fatty acid derivatives with different chain lengths, saturation and/or branching characteristics. In still other exemplary embodiments, a "fatty acid derivative composition" comprises a mixture of fatty esters and 3-hydroxy esters. In still other exemplary embodiments, a fatty acid derivative composition comprises a mixture of fatty alcohols and fatty aldehydes, for example a mixture of non-native monounsaturated fatty alcohols or fatty aldehydes. In other exemplary embodiments, the mixture of fatty acid derivatives includes a mixture of non-native monounsaturated fatty acid derivatives with different chain lengths, saturation and/or functional group characteristics.

The term "attenuated," as used herein, refers to the expression of a protein or enzyme, such as dual 3-hydroxy acyl-ACP dehydratase/isomerase (FabA), which is reduced as compared to wild-type or conventional expression levels of the protein or enzyme in a wild-type proteobacteria. The degree of attenuation is not particularly limited and encompasses a reduction in expression of, for example, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, and at least about 95%. Where expression of the protein or enzyme is completely abolished, the protein or enzyme is considered "deleted," rather than "attenuated."

The term "non-native monounsaturated fatty acid derivative" as used herein, refers to any mUFA derivative derived from a mUFA acyl-thioester where the double bond position is non-native to the producing cell (e.g., proteobacterium). For example, in *E. coli* the native double-bond position in monounsaturated fatty acid acyl-thioesters is omega-7 (ω-7). Therefore, for example in *E. coli*, a mUFA derivative derived from a mUFA acyl-thioester with a double bond in a position other than ω-7 is defined as a non-native mUFA derivative for this bacterium. Examples of non-native mUFA and derivatives thereof have double bonds at ω-3, ω-5, ω-6, ω-8, ω-9, ω-11, and/or ω-12.

Fatty acid compositions may comprise non-native mUFAs or derivatives thereof. Compositions comprising non-native mUFA or derivatives thereof produced by the recombinant proteobacteria disclosed herein typically comprise compositions wherein the non-native mUFA or derivative thereof is at least about 10% of the total mUFA (including native and non-native mUFAs) produced. In some embodiments, compositions comprising non-native mUFA or derivatives thereof produced by the recombinant proteobacteria disclosed herein comprise compositions wherein the non-native mUFA or derivative thereof is at least about 20% of the total mUFA or derivatives thereof. In other embodiments, compositions comprising non-native mUFA or derivatives thereof produced by the recombinant proteobacteria disclosed herein comprise compositions wherein the non-native mUFA or derivatives thereof is at least about 30%, at least about 40%, at least about 50%, at least about 60%, at least about 70%, at least about 75%, at least about 80%, at least about 85%, at least about 90%, at least about 95%, at least about 96%, at least about 97%, at least about 98%, at least about 99%, of the total mUFA or derivatives thereof.

Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers" or alternatively a simply "Accession Numbers"), and from the UniProt Knowledgebase (UniProtKB) and Swiss-Prot databases provided by the Swiss Institute of Bioinformatics (which are identified herein as "UniProtKB Accession Numbers").

The term "enzyme classification (EC) number" refers to a number that denotes a specific polypeptide sequence or enzyme. EC numbers classify enzymes according to the reaction they catalyze. EC numbers are established by the nomenclature committee of the international union of biochemistry and molecular biology (IUBMB), a description of which is available on the IUBMB enzyme nomenclature website on the world wide web.

As used herein, the term "isolated," with respect to products (such as mUFA derivatives disclosed herein) refers to products that are separated from cellular components, cell culture media, or chemical or synthetic precursors. The mUFA derivatives disclosed herein produced by the methods disclosed herein can be relatively immiscible in the fermentation broth, as well as in the cytoplasm. Therefore, in exemplary embodiments, the non-native mUFA derivatives disclosed herein collect in an organic phase extracellularly and are thereby "isolated".

As used herein, the terms "polypeptide" and "protein" are used interchangeably to refer to a polymer of amino acid residues that is typically 12 or more amino acids in length. Polypeptides less than 12 amino acids in length are referred to herein as "peptides." The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide. In some exemplary embodiments, DNA or RNA encoding an expressed peptide, polypeptide or protein is inserted into the host chromosome via homologous recombination or other means well known in the art, and is so used to transform a host cell to produce the peptide or polypeptide. Similarly, the terms "recombinant polynucleotide" or "recombinant nucleic acid" or "recombinant DNA" are produced by recombinant techniques that are known to those of skill in the art (see e.g., methods described in Sambrook et al. (Sambrook et al., Molecular Cloning—A Laboratory Manual, Cold Spring Harbor Press 4$^{th}$ Edition (Cold Spring Harbor, N.Y. 2012) and/or Current Protocols in Molecular Biology (Volumes 1-3, John Wiley & Sons, Inc. (1994-1998) and Supplements 1-115 (1987-2016)).

When referring to two nucleotide or polypeptide sequences, the "percentage of sequence identity" between the two sequences is determined by comparing the two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The "percentage of sequence identity" is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Thus, the expression "percent identity," or equivalently "percent sequence identity," "homology, or "homologous" in the context of two or more nucleic acid sequences or peptides or polypeptides, refers to two or more sequences or subsequences that are the same or have a specified percentage of nucleotides or amino acids that are the same (e.g., about 50% identity, preferably 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured e.g., using a BLAST or BLAST 2.0 sequence comparison algorithm with default parameters (see e.g., Altschul et al. (1990) *J. Mol. Biol.* 215(3):403-410) and/or the NCBI web site atncbi.nlm.nih.gov/BLAST/) or by manual alignment and visual inspection. Percent sequence identity between two nucleic acid or amino acid sequences also can be determined using e.g., the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) *J. Mol. Biol.* 48:444-453). The percent sequence identity between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial sequence identity calculations and adjust the algorithm parameters accordingly. A set of parameters that may be used if a practitioner is uncertain about which parameters should be applied to determine if a molecule is within a sequence identity limitation of the claims, are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) *BMC Bioinformatics* 6:278; Altschul et al. (2005) *FEBS J.* 272(20):5101-5109).

Two or more nucleic acid or amino acid sequences are said to be "substantially identical," when they are aligned and analyzed as discussed above and are found to share about 50% identity, preferably 55%, 60%, 65%, 70%, 75%, 80%, 85%, 90%, 91%, 92%, 93%, 94%, 95%, 96%, 97%, 98%, 99%, or higher identity over a specified region. Two nucleic acid sequences or polypeptide sequences are said to be "identical" if the sequence of nucleotides or amino acid residues, respectively, in the two sequences are the same when aligned for maximum correspondence as described above. This definition also refers to, or may be applied to, the compliment of a test sequence. Identity is typically calculated over a region that is at least about 25 amino acids or nucleotides in length, or more preferably over a region that is 50-100 amino acids or nucleotides in length, or over the entire length of a given sequence.

The term "endogenous" as used herein refers to a substance e.g., a nucleic acid, protein, etc. that is produced from within a cell. Thus, an endogenous polynucleotide or polypeptide refers to a polynucleotide or polypeptide produced by the cell. In some exemplary embodiments an endogenous polypeptide or polynucleotide is encoded by the genome of the parental cell (or host cell). In other exemplary embodiments, an endogenous polypeptide or polynucleotide is encoded by an autonomously replicating plasmid carried by the parental cell (or host cell). In some exemplary embodiments, an endogenous gene is a gene that was present in the cell when the cell was originally isolated from nature i.e., the gene is native to the cell. In other exemplary embodiments, an "endogenous" gene has been altered through recombinant techniques e.g., by altering the relationship of control and/or coding sequences. Thus, a heterologous gene may, in some exemplary embodiments, be endogenous to a host cell. Additionally, a variant (i.e., mutant) polypeptide may be produced from with the and would be considered endogenous polypeptide.

In contrast, an "exogenous" polynucleotide or polypeptide, or other substance (e.g., fatty acid derivative, small molecule compound, etc.) refers to a polynucleotide or polypeptide or other substance that is not encoded or produced by the cell and which is therefore added to a cell, a cell culture, or assay from outside of the cell. A variant (i.e., mutant) polypeptide added to the cell, cell culture, or assay is one example of an exogenous polypeptide.

As used herein the term "native" refers to the form of a nucleic acid, protein, polypeptide, or a fragment thereof that is isolated from nature or a nucleic acid, protein, polypeptide, or a fragment thereof that is in its natural state without intentionally introduced mutations in the structural sequence and/or without any engineered changes in expression such as e.g., changing a developmentally regulated gene to a constitutively expressed gene. As used herein, "native" also refers to "wildtype" or "wild-type," in which the nucleic acid, protein, polypeptide, or a fragment thereof is present in both sequence, quantity, and relative quantity as typically found in the organism as naturally found. Wild-type organisms may serve as a control and/or reference for determination of cellular functions, such as identity and/or quantity of mUFA(s) produced or relative binding of heterologous regulatory elements (e.g., FadR) to cognate DNA sequences.

The term "non-native" is used herein to refer to nucleic acid sequences, amino acid sequences, fatty acids, and derivatives thereof, and/or small molecules that do not occur naturally in the host. Heterologous genes are considered "non-native." A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous and/or native to the host microorganism but operably linked to one or more heterologous regulatory sequences that have been recombined into the host genome. A naturally occurring gene under the control of a heterologous regulatory sequence is considered "non-native."

The term "gene" as used herein, refers to nucleic acid sequences e.g., DNA sequences, which encode either an RNA product or a protein product, as well as operably-linked nucleic acid sequences that affect expression of the RNA or protein product (e.g., expression control sequences such as e.g., promoters, enhancers, ribosome binding sites, translational control sequences, etc.). The term "gene product" refers to either the RNA (e.g., tRNA, mRNA) and/or protein expressed from a particular gene.

The term "expression" or "expressed" as used herein in reference to a gene, refers to the production of one or more transcriptional and/or translational product(s) of a gene. In exemplary embodiments, the level of expression of a DNA molecule in a cell is determined on the basis of either the amount of corresponding mRNA that is present within the cell or the amount of protein encoded by that DNA produced by the cell. The term "expressed genes" refers to genes that are transcribed into messenger RNA (mRNA) and then translated into protein, as well as genes that are transcribed into other types of RNA, such as e.g., transfer RNA (tRNA), ribosomal RNA (rRNA), and regulatory RNA, which are not translated into protein.

The level of expression of a nucleic acid molecule in a cell or cell free system is influenced by "expression control sequences" or equivalently "regulatory sequences" or "regulatory elements." Expression control sequences, regulatory sequences, or regulatory elements are known in the art and include, for example, promoters, enhancers, polyadenylation signals, transcription terminators, nucleotide sequences that affect RNA stability, internal ribosome entry sites (IRES), and the like, that provide for the expression of the polynucleotide sequence in a host cell. In exemplary embodiments, "expression control sequences" interact specifically with cellular proteins involved in transcription (see e.g., Maniatis et al., Science, 236: 1237-1245 (1987); Goeddel, Gene Expression Technology: Methods in Enzymology, Vol. 185, Academic Press, San Diego, Calif. (1990)). In exemplary methods, an expression control sequence, regulatory sequence, or regulatory element is operably linked to a polynucleotide sequence. By "operably linked" is meant that a polynucleotide sequence and an expression control sequence(s) or regulatory element(s) are functionally connected so as to permit expression of the polynucleotide sequence when the appropriate molecules (e.g., transcriptional activator proteins) contact the expression control sequence(s). In exemplary embodiments, operably linked promoters are located upstream of the selected polynucleotide sequence in terms of the direction of transcription and translation. In some exemplary embodiments, operably linked enhancers can be located upstream, within, or downstream of the selected polynucleotide.

As used herein, the phrase "expression of said nucleotide sequence is modified relative to the wild-type nucleotide sequence," refers to a change e.g., an increase or decrease in the level of expression of a native nucleotide sequence or a change e.g., an increase or decrease in the level of the expression of a heterologous or non-native polypeptide-encoding nucleotide sequence as compared to a control nucleotide sequence e.g., wild-type control. In some exemplary embodiments, the phrase "the expression of said nucleotide sequence is modified relative to the wild type nucleotide sequence," refers to a change in the pattern of expression of a nucleotide sequence as compared to a control pattern of expression e.g., constitutive expression as compared to developmentally timed expression.

A "control" sample (e.g., a control nucleotide sequence, a control polypeptide sequence, a control cell, etc., or value) refers to a sample that serves as a reference, usually a known reference, for comparison to a test sample. For example, in an exemplary embodiment, a test sample comprises a non-native monounsaturated fatty acid derivative composition made by a recombinant proteobacterium that comprises a heterologous acyl-ACP desaturase and a heterologous acyl-ACP thioesterase, wherein the native dual 3-hydroxy acyl-ACP dehydratase/isomerase (Fad A) is deleted, as disclosed herein, while the control sample comprises a non-native monounsaturated fatty acid derivative composition made by the corresponding or designated bacterium that does not comprise a heterologous acyl-ACP desaturase and a heterologous acyl-ACP thioesterase and does not have its native dual 3-hydroxy acyl-ACP dehydratase/isomerase (Fad A) deleted. Additionally, a control cell or microorganism may be referred to as a corresponding wild type or host cell. One of skill will recognize that controls can be designed for assessment of any number of parameters. Furthermore, one of skill in the art will understand which controls are valuable in a given situation and will be able to analyze data based on comparisons to control values.

The terms "overexpressed" or "up-regulated" as used herein, refer to a gene whose expression is elevated in comparison to a control level of expression. In exemplary embodiments, overexpression of a gene is caused by an elevated rate of transcription as compared to the native transcription rate for that gene. In other exemplary embodiments, overexpression is caused by an elevated rate of translation of the gene compared to the native translation rate for that gene. Methods of testing for overexpression are well known in the art, for example transcribed RNA levels can be assessed using rtPCR and protein levels can be assessed using SDS page gel analysis.

In other embodiments, the polypeptide, polynucleotide, or hydrocarbon having an altered level of expression is "attenuated" or has a "decreased level of expression" or is "down-regulated." As used herein, these terms mean to express or cause to be expressed a polynucleotide, polypeptide, or hydrocarbon in a cell at a lesser concentration than is normally expressed in a corresponding control cell (e.g., wild type cell) under the same conditions. In other words, the term "attenuate" means to weaken, reduce, or diminish. For example, a polypeptide can be attenuated by modifying the polypeptide to reduce its activity (e.g., by modifying a nucleotide sequence that encodes the polypeptide).

A polynucleotide or polypeptide can be attenuated using any method known in the art. For example, in some exemplary embodiments, the expression of a gene or polypeptide encoded by the gene is attenuated by mutating the regulatory polynucleotide sequences which control expression of the gene. In other exemplary embodiments, the expression of a gene or polypeptide encoded by the gene is attenuated by overexpressing a repressor protein, or by providing an exogenous regulatory element that activates a repressor protein. In still other exemplary embodiments, DNA- or RNA-based gene silencing methods are used to attenuate the expression of a gene or polynucleotide. In some embodiments, the expression of a gene or polypeptide is completely attenuated, e.g., by deleting all or a portion of the polynucleotide sequence of a gene.

The degree of overexpression or attenuation can be 1.5-fold or more, e.g., 2-fold or more, 3-fold or more, 5-fold or more, 10-fold or more, or 15-fold or more. Alternatively, or in addition, the degree of overexpression or attenuation can be 500-fold or less, e.g., 100-fold or less, 50-fold or less, 25-fold or less, or 20-fold or less. Thus, the degree of overexpression or attenuation can be bounded by any two of the above endpoints. For example, the degree of overexpression or attenuation can be 1.5-500-fold, 2-50-fold, 10-25-fold, or 15-20-fold.

As used herein, "modified activity" or an "altered level of activity" of a protein/polypeptide in a recombinant host cell refers to a difference in one or more characteristics in the activity the protein/polypeptide as compared to the characteristics of an appropriate control protein e.g., the corresponding parent protein or corresponding wild type protein. Thus, in exemplary embodiments, a difference in activity of a protein having "modified activity" as compared to a corresponding control protein is determined by measuring the activity of the modified protein in a recombinant host cell and comparing that to a measure of the same activity of a corresponding control protein in an otherwise isogenic host cell. Modified activities can be the result of, for example, changes in the structure of the protein (e.g., changes to the primary structure, such as e.g., changes to the protein's nucleotide coding sequence that result in changes in substrate specificity, changes in observed kinetic parameters, changes in solubility, etc.); changes in protein stability (e.g., increased or decreased degradation of the protein) etc.

The term "heterologous" as used herein refers to a polypeptide or polynucleotide which is in a non-native state. Thus, a polynucleotide or a polypeptide is "heterologous" to a cell when the polynucleotide and/or the polypeptide and the cell are not found in the same relationship to each other in nature. Therefore, a polynucleotide or polypeptide sequence is "heterologous" to an organism or a second sequence if it originates from a different organism, different cell type, or different species, or, if from the same species, it is modified from its original form. Thus, in an exemplary embodiment, a polynucleotide or polypeptide is "heterologous" when it is not naturally present in a given organism. For example, a polynucleotide sequence that is native to cyanobacteria can be introduced into a host cell of *E. coli* by recombinant methods, and the polynucleotide from cyanobacteria is then heterologous to the *E. coli* cell (i.e., the now recombinant *E. coli* cell).

Similarly, a polynucleotide or polypeptide is heterologous when it is modified from its native form or from its relationship with other polynucleotide sequences or is present in a recombinant host cell in a non-native state. Thus, in an exemplary embodiment, a heterologous polynucleotide or polypeptide comprises two or more subsequences that are not found in the same relationship to each other in nature. For example, a promoter operably linked to a nucleotide coding sequence derived from a species different from that from which the promoter was derived. Alternatively, in another example, if a promoter is operably linked to a nucleotide coding sequence derived from a species that is the same as that from which the promoter was derived, then the operably-linked promoter and coding sequence are "heterologous" if the coding sequence is not naturally associated with the promoter (e.g., a constitutive promoter operably linked to a developmentally regulated coding sequence that is derived from the same species as the promoter). In other exemplary embodiments, a heterologous polynucleotide or polypeptide is modified relative to the wild type sequence naturally present in the corresponding wild type host cell, e.g., an intentional modification e.g., an intentional mutation in the sequence of a polynucleotide or polypeptide or a modification in the level of expression of the polynucleotide or polypeptide. Typically, a heterologous nucleic acid or polynucleotide is recombinantly produced.

The term "recombinant" as used herein, refers to a genetically modified polynucleotide, polypeptide, cell, tissue, or organism. When used with reference to a cell, the term "recombinant" indicates that the cell has been modified by the introduction of a heterologous nucleic acid or protein or has been modified by alteration of a native nucleic acid or protein, or that the cell is derived from a cell so modified and that the derived cell comprises the modification. Thus, for example, "recombinant cells" or equivalently "recombinant host cells" may be modified to express genes that are not found within the native (non-recombinant) form of the cell or may be modified to abnormally express native genes e.g., native genes may be overexpressed, underexpressed or not expressed at all. In exemplary embodiments, a "recombinant cell" or "recombinant host cell" is engineered to express a heterologous enzyme pathway capable of producing a bifunctional fatty acid derivative molecule. A recombinant cell can be derived from a microorganism such as a bacterium, proteobacterium, archaea, a virus or a fungus. In addition, a recombinant cell can be derived from a plant or an animal cell. In exemplary embodiments, a "recombinant host cell" or "recombinant cell" is used to produce one or more non-native monounsaturated fatty acid derivatives including, but not limited to, non-native monounsaturated fatty acids, non-native monounsaturated fatty esters (e.g., waxes), fatty acid esters, fatty esters, fatty acid methyl esters (FAME), fatty acid ethyl esters (FAEE)), non-native monounsaturated fatty acyl acetate esters (FACE), non-native monounsaturated fatty alcohols (e.g., polyols), non-native monounsaturated fatty aldehydes, non-native monounsaturated fatty amines, non-native monounsaturated terminal olefins, non-native monounsaturated ketones, etc. Therefore, in some exemplary embodiments a "recombinant host cell" is a "production host" or equivalently, a "production host cell". In some exemplary embodiments, the recombinant cell includes one or more polynucleotides, each polynucleotide encoding a polypeptide having fatty acid biosynthetic enzyme activity, wherein the recombinant cell produces a non-native monounsaturated fatty acid derivative composition when cultured in the presence of a (simple) carbon source under conditions effective to express the polynucleotides.

When used with reference to a polynucleotide, the term "recombinant" indicates that the polynucleotide has been modified by comparison to the native or naturally occurring form of the polynucleotide or has been modified by comparison to a naturally occurring variant of the polynucleotide. In an exemplary embodiment, a recombinant polynucleotide (or a copy or complement of a recombinant polynucleotide) is one that has been manipulated by the hand of man to be different from its naturally occurring form. Thus, in an exemplary embodiment, a recombinant polynucleotide is a mutant form of a native gene or a mutant form of a naturally occurring variant of a native gene wherein the mutation is made by intentional human manipulation e.g., made by saturation mutagenesis using mutagenic oligonucleotides, through the use of UV radiation, mutagenic chemicals, chemical synthesis, etc. Such a recombinant polynucleotide might comprise one or more point mutations, deletions and/or insertions relative to the native or naturally occurring variant form of the gene. Similarly, a polynucleotide comprising a promoter operably linked to a second polynucleotide (e.g., a coding sequence) is a "recombinant" polynucleotide. Thus, a recombinant polynucleotide comprises polynucleotide combinations that are not found in nature. A recombinant protein (discussed supra) is typically one that is expressed from a recombinant polynucleotide, and recombinant cells, tissues, and organisms are those that comprise recombinant sequences (polynucleotide and/or polypeptide).

The term "vector," as used herein, refers to a polynucleotide sequence that contains a gene of interest (e.g., encodes one or more proteins or enzymes described herein) and a promoter operably linked to the fatty acid biosynthetic polynucleotide sequence of interest. Once a polynucleotide sequence(s) encoding a fatty acid biosynthetic pathway polypeptide has been prepared and isolated, various methods may be used to construct expression cassettes, vectors, and other DNA constructs. The skilled artisan is well aware of the genetic elements that must be present on an expression construct/vector in order to successfully transform, select and propagate the expression construct in host cells. Techniques for manipulation of nucleic acids such as subcloning nucleic acid sequences into expression vectors, labeling probes, DNA hybridization are well known in the art.

As used herein, the term "microorganism" refers generally to a microscopic organism. Microorganisms can be prokaryotic or eukaryotic. Exemplary prokaryotic microorganisms include e.g., bacteria (including γ-proteobacteria), archaea, cyanobacteria, etc. An exemplary proteobacterium is *Escherichia coli*. Exemplary eukaryotic microorganisms include e.g., yeast, protozoa, algae, etc. In exemplary embodiments, a "recombinant microorganism" is a microorganism that has been genetically altered and thereby expresses or encompasses a heterologous nucleic acid sequence and/or a heterologous protein.

The expression "viable bacterium" or "viable bacteria" or "viable microorganism" as used herein, refers to a bacterium (including proteobacterium) that grows on a carbon source e.g., a simple carbon source, wherein the media used for culturing the microorganism does not contain any exogenous fatty acid or fatty acid derivative, nor any compound(s) that is/are an inhibitor of fatty acid biosynthesis, e.g., triclosan, which inhibits the fabI-type trans-2-enoyl-ACP reductase. Typically, as used herein, a viable recombinant bacterium, including a recombinant proteobacterium, comprises at least one heterologous acyl-ACP desaturase and at least one heterologous acyl-ACP thioesterase, and wherein 3-hydroxy acyl-ACP the native dual 3-hydroxy acyl-ACP dehydratase/isomerase (FabA) is deleted or attenuated. In some embodiments, the recombinant proteobacterium is a gamma proteobacterium (also known as a γ-proteobacterium). In some embodiments, the recombinant proteobacterium may be *Escherichia coli*, *Salmonella* spp., *Vibrio natriegens*, *Pseudomonas aeruginosa*, *Pseudomonas putida*, *Pseudomonas fluorescens*, *Xanthomonas axonopodis*, *Pseudomonas syringae*, *Xyella fastidiosa*, *Marinobacter aquaeolei*, *Yersinia pestis*, or *Vibrio cholerae*.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen.

"Culturing" or "cultivation" refers to growing a population of recombinant host cells under suitable conditions in a liquid or solid medium. In particular embodiments, culturing refers to the fermentative bioconversion of a substrate to an end-product. Culturing media are well known, and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium.

Typically, a "recombinant proteobacterium" as disclosed herein will comprise within its cellular fatty acids/membrane phospholipids the non-native monounsaturated fatty acid (or fatty acid derivative) produced by the cell that has the characteristic double bond structure. In some embodiments, the non-native monounsaturated fatty acid derivative comprises at least 5% of the membrane phospholipids. In other embodiments, the non-native monounsaturated fatty acid derivative comprises at least 10% of the membrane phospholipids. In still other embodiments, the non-native monounsaturated fatty acid derivative comprises at least 11%, at least 12%, at least 15%, at least 20%, at least 25%, at least 30%, at least 35%, at least 40%, of the membrane phospholipids. In another embodiment, the recombinant proteobacterium will comprise a free fatty acid composition of at least 11%, at least 12%, at least 15%, at least 20%, at least 25%, at least 30%, at least 35%, at least 40%, at least 50%, at least 60%, or at least 70%, non-native monounsaturated fatty acid.

A "production host" or equivalently a "production host cell" is a cell used to produce products. As disclosed herein, a production host is typically modified to express or overexpress selected genes, or to have attenuated expression of selected genes. Thus, a production host or a production host cell is a recombinant host or equivalently a recombinant host cell. Non-limiting examples of production hosts include e.g., recombinant proteobacteria as disclosed above. An exemplary production host is a recombinant proteobacterium comprising a heterologous acyl-ACP desaturase and a heterologous acyl-ACP thioesterase, wherein the native dual 3-hydroxy acyl-ACP dehydratase/isomerase (FabA) is deleted or attenuated.

As used herein, the terms "purify," "purified," or "purification" mean the removal or isolation of a molecule from its environment by, for example, isolation or separation. "Substantially purified" molecules are at least about 60% free (e.g., at least about 65% free, at least about 70% free, at least about 75% free, at least about 80% free, at least about 85% free, at least about 90% free, at least about 95% free, at least about 96% free, at least about 97% free, at least about 98% free, at least about 99% free) from other components with which they are associated. As used herein, these terms also refer to the removal of contaminants from a sample.

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; succinate, lactate, and acetate; alcohols, such as ethanol, methanol, and glycerol, or mixtures thereof. The carbon source can also be a product of photosynthesis, such as glucose. In certain embodiments, the carbon source is biomass. In other embodiments, the carbon source is glucose. In other embodiments the carbon source is sucrose. In other embodiments the carbon source is glycerol. In other embodiments, the carbon source is a simple carbon source such as e.g., glucose. In other embodiments, the carbon source is a renewable carbon source. In other embodiment, the carbon source is natural gas. In other embodiments the carbon source comprises one or more components of natural gas, such as methane, ethane, or propane. In other embodiments, the carbon source is flu gas or synthesis gas. In still other embodiments, the carbon source comprises one or more components of flu or synthesis gas such as carbon monoxide, carbon dioxide, hydrogen, etc. As used herein, the term "carbon source" or "simple carbon source" specifically excludes oleochemicals such as e.g., saturated or unsaturated fatty acids.

Enzymes

As used herein, the term "acyl-ACP desaturase" refers to an enzyme that belongs in the oxidoreductase family of enzymes and catalyzes the reaction of saturated acyl-ACP to cis-monounsaturated acyl-ACP. For example, the saturated acyl-ACP may be stearoyl-ACP and the cis-monounsaturated acyl-ACP may be oleoyl-ACP. The acyl-ACP desaturase may be native to the cell (e.g., present in the cell in its natural state without any intentionally induced mutations or changes to its expression) or may be heterologous (e.g., present in cell in an unnatural state, for example the enzyme is intentionally mutated or has an intentionally altered expression). In some embodiments, wherein the acyl-ACP desaturase is heterologous, it may be endogenous, wherein the enzyme, or a polynucleotide encoding the enzyme (e.g., RNA) is produced by the cell. In another embodiment, wherein the acyl-ACP desaturase is heterologous, it may be exogenous, wherein the enzyme or a polynucleotide encoding the enzyme is not produced by the cell, but instead is added to the cell from outside the cell. In some embodiments, the acyl-ACP desaturases described herein may belong to EC 1.14.19.2. The particular acyl-ACP desaturase determines where the cis double bond in the mUFA or derivative is located. In a particular embodiment, the acyl-ACP desaturase is Δ9-tetradecanoyl-acyl-ACP desaturase. In a further embodiment, the acyl-ACP desaturase has about an 85% sequence identity to SEQ ID NO: 2. In still further embodiments, the acyl-ACP desaturase has about a 90% sequence identity to SEQ ID NO: 2, about a 95% sequence identity to SEQ ID NO: 2, about a 99% sequence identity to SEQ ID NO: 2, or is SEQ ID NO: 2 (e.g., 100% sequence homology). In another embodiment, the acyl-ACP desaturase has about an 85% sequence identity to SEQ ID NO: 12. In still further embodiments, heterologous acyl-ACP desaturase has about a 90% sequence identity to SEQ ID NO: 12, about a 95% sequence identity to SEQ ID NO: 12, about a 99% sequence identity to SEQ ID NO: 12, or is SEQ ID NO: 12 (e.g., 100% sequence homology).

As used herein, the term "acyl-ACP thioesterase" refers to an enzyme that catalyzes the hydrolysis of thioester bonds to terminate fatty acyl extension. The acyl-ACP thioesterase may be native to the recombinant proteobacterium or may be heterologous. In some embodiments, the heterologous acyl-ACP thioesterase may be endogenous, wherein the enzyme, or a polynucleotide encoding the enzyme (e.g., RNA) is produced by the cell. In another embodiment, the heterologous acyl-ACP thioesterase may be exogenous, wherein the enzyme or a polynucleotide encoding the enzyme is not produced by the cell, but instead is added to the cell from outside the cell. In some embodiments, the acyl-ACP thioesterases described herein may belong to EC 3.1.2.14. The particular acyl-ACP thioesterase determines the chain length of the mUFA or derivative thereof. In a particular embodiment, the acyl-ACP thioesterase is a plant FatA-type thioesterase (which is specific for acyl-ACPs with C16 and C18 chain lengths), a plant FatB-type thioesterase (which is specific for acyl-ACPs with a C14 chain length), or a bacterial acyl-ACP thioesterase (for example, the thioesterase from C. thermocellum that hydrolyzes acyl-ACPs of various chain lengths, including z9-tetradecanol). In a further embodiment, the acyl-ACP thioesterase has about an 85% sequence identity to SEQ ID NO: 8. In still further embodiments, the acyl-ACP thioesterase has about a 90% sequence identity to SEQ ID NO: 8, about a 95% sequence identity to SEQ ID NO: 8, about a 99% sequence identity to SEQ ID NO: 8, or is SEQ ID NO: 8 (e.g., 100% sequence homology).

E. coli has two 3-hydroxy-acyl-ACP dehydratases, FabZ and FabA [EC 4.2.1.59]. A key enzyme for mUFA synthesis is one of these enzymes, FabA, which is a dual function dehydratase/isomerase. FabA isomerizes trans-2-decenoyl-ACP to cis-3-decenoyl-ACP. The latter cannot be reduced by trans-2-enoyl-ACP reductase, FabI, but can be elongated by R-keto-acyl-ACP synthase I, FabB, thereby fixating the double bond position in the ω-7 position (i.e., native position, counted from the reduced end of the acyl chain) of mUFAs with chain length C10, C12, C14, C16 and C18. It should be noted that the common chemical nomenclature designates the double bond position in fatty acids counting from the carboxyl group and not from the reducing end, and it uses (z) for cis- and (e) for trans-configuration, accordingly the native mUFAs in E. coli are z3-C10:1 (=ω7-C10: 1), z5-C12:1 (=ω7-C12:1), C14:1 (=ω7-C14:1), z9-C16:1 (=ω7-C16:1) and z11-C18:1 (=ω7-C18:1). Thus, the expression "dual 3-hydroxy acyl-ACP dehydratase/isomerase" as used herein, refers to an enzyme having (3-hydroxyacyl-[acyl-carrier-protein] dehydratase) activity described by EC number: EC 4.2.1.59 and enoyl-acyl-carrier protein isomerase activity described by EC number: EC 5.3.3.14 (see e.g., Heath R J, Rock C O (1996) Roles of the FabA and FabZ beta-hydroxyacyl-acyl carrier protein dehydratases in Escherichia coli fatty acid biosynthesis. J Biol Chem 271: 27795-801). The dual 3-hydroxy acyl-ACP dehydratase/isomerase may be native to the recombinant proteobacterium or may be heterologous. In some embodiments, the heterologous 3-hydroxy acyl-ACP dehydratase may be endogenous, wherein the enzyme, or a polynucleotide encoding the enzyme (e.g., RNA), is produced by the cell. In another embodiment, the dual 3-hydroxy acyl-ACP dehydratase/isomerase may be exogenous, wherein the enzyme or a polynucleotide encoding the enzyme is not produced by the cell, but instead is added to the cell from outside the cell. In some embodiments, the 3-hydroxy acyl-ACP dehydratase described herein may belong to EC 4.2.1.59.

As used herein, the term "carboxylic acid reductase" refers to an enzyme that converts a fatty acid to its corresponding aldehyde. The carboxylic acid reductase may be native to the recombinant proteobacterium or may be heterologous. In some embodiments, the heterologous carboxylic acid reductase may be endogenous, wherein the enzyme, or a polynucleotide encoding the enzyme (e.g., RNA), is produced by the cell. In another embodiment, the heterologous carboxylic acid reductase may be exogenous, wherein the enzyme or a polynucleotide encoding the enzyme is not produced by the cell, but instead is added to the cell from outside the cell. In some embodiments, the carboxylic acid reductase described herein may belong to EC 1.2.1.30. In a further embodiment, the carboxylic acid reductase has about an 85% sequence identity to SEQ ID NO: 18. In still further embodiments, the carboxylic acid reductase has about a 90% sequence identity to SEQ ID NO: 18, about a 95% sequence identity to SEQ ID NO: 18, about a 99% sequence identity to SEQ ID NO: 18, or is SEQ ID NO: 18 (e.g., 100% sequence homology).

As used herein, the term "ferredoxin" refers to an iron-sulfur protein that mediates the transfer of electrons in metabolic reactions. The ferredoxin may be native to the recombinant proteobacterium or may be heterologous. In some embodiments, the heterologous ferredoxin may be endogenous, wherein the enzyme, or a polynucleotide encoding the enzyme (e.g., RNA), is produced by the cell. In another embodiment, the heterologous ferredoxin may be exogenous, wherein the enzyme or a polynucleotide encoding the enzyme is not produced by the cell, but instead is added to the cell from outside the cell. In some embodiments ferredoxin refers to PetF, ferredoxin reductase (PetH), and flavodoxin/ferredoxin-NADP$^+$ reductase (Fpr). In some embodiments, the ferredoxin described herein may belong to EC 1.18.1.2.

As used herein, the term "alcohol dehydrogenase" refers to an enzyme that catalyzes the interconversion between aliphatic alcohols (e.g., aliphatic medium-chain alcohols) and their corresponding aldehydes. The alcohol dehydrogenase may be native to the recombinant proteobacterium or may be heterologous. In some embodiments, and under some conditions, the alcohol dehydrogenase converts an alcohol into an aldehyde. In some embodiments and under some conditions, the alcohol dehydrogenase converts an aldehyde into an alcohol. In some embodiments, the heterologous alcohol dehydrogenase may be endogenous, wherein the enzyme, or a polynucleotide encoding the enzyme (e.g., RNA), is produced by the cell. In another embodiment, the heterologous alcohol dehydrogenase may be exogenous, wherein the enzyme or a polynucleotide encoding the enzyme is not produced by the cell, but instead is added to the cell from outside the cell. In some embodiments, the alcohol dehydrogenase may belong to EC 1.1.1.1. In a further embodiment, the alcohol dehydrogenase has about an 85% sequence identity to SEQ ID NO: 20. In still further embodiments, the alcohol dehydrogenase has about a 90% sequence identity to SEQ ID NO: 20, about a 95% sequence identity to SEQ ID NO: 20, about a 99% sequence identity to SEQ ID NO: 20, or is SEQ ID NO: 20 (e.g., 100% sequence homology).

As used herein, the term "ω-hydroxylase" refers to an enzyme that hydrolyzes a fatty acid derivative in the ω-position. The ω-hydroxylase may be native to the recombinant proteobacterium or may be heterologous. In some embodiments, the heterologous ω-hydroxylase may be endogenous, wherein the enzyme, or a polynucleotide encoding the enzyme (e.g., RNA) is produced by the cell. In another embodiment, the heterologous ω-hydroxylase may be exogenous, wherein the enzyme or a polynucleotide encoding the enzyme is not produced by the cell, but instead is added to the cell from outside the cell. In some embodiments, the ω-hydroxylase may belong to EC 1.14.15.3 or 1.14.14.80. In a further embodiment, the ω-hydroxylase may be a hybrid-fusion P450 enzyme or variant thereof such as one disclosed in WO 2014/201474 or WO 2017/106205, which are incorporated herein by reference in their entirety. In a particular embodiment the ω-hydroxylase has about an 85% sequence identity to SEQ ID NO: 22. In still further embodiments, the ω-hydroxylase has about a 90% sequence identity to SEQ ID NO: 22, about a 95% sequence identity to SEQ ID NO: 22, about a 99% sequence identity to SEQ ID NO: 22, or is SEQ ID NO: 22 (e.g., 100% sequence homology).

As used herein, the term "alcohol acetyl-CoA transferase" refers to an enzyme that converts an alcohol to an acetyl ester. The alcohol acetyl-CoA transferase may be native to the recombinant proteobacterium or may be heterologous. In some embodiments, the heterologous alcohol acetyl-CoA transferase may be endogenous, wherein the enzyme, or a polynucleotide encoding the enzyme (e.g., RNA), is produced by the cell. In another embodiment, the heterologous alcohol acetyl-CoA transferase may be exogenous, wherein the enzyme or a polynucleotide encoding the enzyme is not produced by the cell, but instead is added to the cell from outside the cell. In some embodiments, the alcohol acetyl-CoA transferase may belong to EC 2.3.1.84. In a further embodiment, the alcohol acetyl-CoA transferase has about an 85% sequence identity to SEQ ID NO: 24. In still further embodiments, the alcohol acetyl-CoA transferase has about a 90% sequence identity to SEQ ID NO: 24, about a 95% sequence identity to SEQ ID NO: 24, about a 99% sequence identity to SEQ ID NO: 24, or is SEQ ID NO: 24 (e.g., 100% sequence homology).

As used herein, the term "phosphopantetheinyl transferase" refers to an enzyme that transfers the 4'-phosphopantetheine moiety from CoA to the acyl carrier protein. The phosphopantetheinyl transferase may be native to the recombinant proteobacterium or may be heterologous. For example, the entD gene codes for a phosphopantetheinyl transferase. Overexpression of native *E. coli* entD, a phosphopantetheinyl transferase, enables the activation of carboxylic acid reductase CarB from apo-CarB to holo-CarB, thereby allowing conversion of free fatty acids into fatty aldehydes, which can then be converted to fatty alcohols by a fatty aldehyde reductase. See, for example, U.S. Pat. No. 9,340,801, which is incorporated herein by reference. In some embodiments, the heterologous phosphopantetheinyl transferase may be endogenous, wherein the enzyme, or a polynucleotide encoding the enzyme (e.g., RNA), is produced by the cell. In another embodiment, the heterologous phosphopantetheinyl transferase may be exogenous, wherein the enzyme or a polynucleotide encoding the enzyme is not produced by the cell, but instead is added to the cell from outside the cell. In some embodiments, the phosphopantetheinyl transferase may belong to EC 2.7.8.7.

In a further embodiment, the phosphopantetheinyl transferase has about an 85% sequence identity to SEQ ID NO: 26. In still further embodiments, the phosphopantetheinyl transferase has about a 90% sequence identity to SEQ ID NO: 26, about a 95% sequence identity to SEQ ID NO: 26, about a 99% sequence identity to SEQ ID NO: 26, or is SEQ ID NO: 26 (e.g., 100% sequence homology).

As used herein, the term "aldehyde dehydrogenase" refers to enzymes that converts aldehydes to carboxylic acids. The aldehyde dehydrogenasee may be native to the recombinant proteobacterium or may be heterologous. In some embodiments, the heterologous aldehyde dehydrogenase may be endogenous, wherein the enzyme, or a polynucleotide encoding the enzyme (e.g., RNA) is produced by the cell. In another embodiment, the heterologous aldehyde dehydrogenase may be exogenous, wherein the enzyme or a polynucleotide encoding the enzyme is not produced by the cell, but instead is added to the cell from outside the cell. Aldehyde dehydrogenase may be described by the number EC 1.2.1.3. In a further embodiment, the heterologous aldehyde dehydrogenase has about an 85% sequence identity to one of SEQ ID NOs:30-32. In still further embodiments, the aldehyde dehydrogenase has about a 90% sequence identity to one of SEQ ID NOs: 30-32, about a 95% sequence identity to one of SEQ ID NOs: 30-32, about a 99% sequence identity to one of SEQ ID NOs: 30-32, or is one of SEQ ID NOs: 30-32 (e.g., 100% sequence homology).

As used herein, the term "O-ketoacyl-ACP-synthase," which includes "FabB" or "FabF," refers to enzymes that catalyzes the condensation reaction to elongate the fatty acid chain. The β-ketoacyl-ACP synthase may be native to the recombinant proteobacterium or may be heterologous. In some embodiments, the heterologous β-ketoacyl-ACP-synthase may be endogenous, wherein the enzyme or a polynucleotide encoding the enzyme (e.g., RNA) is produced by the cell. In another embodiment, the heterologous β-ketoacyl-ACP-synthase may be exogenous, wherein the enzyme or a polynucleotide encoding the enzyme is not produced by the cell, but instead is added to the cell from outside the cell. β-ketoacyl-ACP-synthase may be described by the number EC 2.3.1.41. In a further embodiment, the β-ketoacyl-ACP-synthase has about an 85% sequence identity to SEQ ID NO:33. In still further embodiments, the β-ketoacyl-ACP-synthase has about a 90% sequence identity to SEQ ID NO: 33, about a 95% sequence identity to SEQ ID NO: 33, about a 99% sequence identity to SEQ ID NO: 33, or is SEQ ID NO: 33 (e.g., 100% sequence homology).

II. Recombinant Proteobacteria and Novel Δ9-Tetradecanoyl-Acyl-ACP Desaturase As discussed above, there is a need for new and efficient recombinant methods for producing non-native mUFAs and derivatives thereof. Thus, in one embodiment a recombinant proteobacterium is described herein which produces non-native mUFAs and derivatives thereof comprising a heterologous acyl-ACP desaturase and a heterologous acyl-ACP thioesterase, wherein the native dual 3-hydroxy acyl-ACP dehydratase/isomerase (FabA) is deleted or attenuated. In some embodiments, the recombinant proteobacterium is a gamma-proteobacterium (e.g., γ-proteobacterium). In a further embodiment, the recombinant proteobacterium may be Escherichia coli, Salmonella spp., Vibrio natriegens, Pseudomonas aeruginosa, Pseudomonas putida, Pseudomonas fluorescens, Xanthomonas axonopodis, Pseudomonas syringae, Xyella fastidiosa, Marinobacter aquaeolei, Yersinia pestis, or Vibrio cholerae. In a particular embodiment, the recombinant proteobacterium is E. coli.

The described recombinant proteobacterium can produce one or more non-native mUFAs or derivatives thereof, such as a ω-3, ω-5, ω-6, ω-8, ω-9, ω-11, ω-12, etc. mUFAs or derivatives thereof. In a particular embodiment, the recombinant proteobacterium produces an ω-5 mUFA or derivative thereof.

In another particular embodiment, the heterologous acyl-ACP desaturase is the newly discovered Δ9-tetradecanoyl-acyl-ACP desaturase from Vitis Vinifera having at least 85% sequence identity to SEQ ID NO:12, or the Δ9-tetradecanoyl-acyl-ACP desaturase from Pelargonium xhortorum having at least 85% sequence identity to SEQ ID NO:2. Some desaturases, mainly found in plants, act on acyl-ACPs. Desaturases that act on acyl-ACP substrates are both soluble and enable altering the cis double bond position in the acyl-ACP other than at the naturally occurring ω-7 position. Without being bound by theory, when an acyl-ACP desaturase is expressed in proteobacteria, the organism can produce mUFAs and derivatives with double bonds that are located at non-native positions, such as at the ω-3, ω-5, ω-6, ω-8, ω-9, ω-11, and ω-12 positions.

Additionally or alternatively, the recombinant proteobacterium further comprises one or more enzymes such as ferredoxin, ferredoxin reductase or flavodoxin reductase, 3-hydroxyacyl-ACP-dehydratase (FabZ), a thioesterase, a carboxylic acid reductase, an alcohol dehydrogenase, a phosphopantetheinyl transferase, an alcohol acetyl-CoA transferase, a ω-hydroxylase, an alcohol oxidase/dehydrogenase, a fatty acid metabolism regulator protein (fadR), an aldehyde hydrogenase, and/or a β-ketoacyl-ACP synthase. One or more of the preceding enzymes may be native to the recombinant proteobacterium or one or more of the preceding enzymes may be heterologous (e.g., non-native). For example, for additional 3-hydroxy-acyl-ACP dehydratase activity in a recombinant ΔFabA strain (e.g., where FabA has been deleted), various heterologous FabZ enzymes can be employed, preferably 3-hydroxy-acyl-ACP dehydratases having activity to dehydrate all 3-hydroxy-acyl-ACP chain lengths (C4 to C18), such as FabZ from Acinetobacter baylyi (UniProtKB-Q6FCG4; SEQ ID NO:16), FabZ from Clostridium acetobutylicum (UniProtKB-Q97DA9; SEQ ID NO:27) or FabZ from Synechococcus elongatus (UniProtKB-Q31PQ9; SEQ ID NO:28).

In another embodiment, in addition to having native dual 3-hydroxy acyl-ACP dehydratase/isomerase (FabA) deleted, the recombinant proteobacterium may be further engineered to comprise a heterologous dual 3-hydroxy acyl-ACP dehydratase/isomerase (FabA), for example by the methods reported in WO 2020/047088, which as stated above, is incorporated herein by reference in its entirety.

In some embodiments, the recombinant proteobacterium produces at least about 30%, at least about 40%, at least about 50%, at least about 60%, at least about 70%, at least about 75%, at least about 80%, at least about 85%, at least about 90%, at least about 95%, at least about 96%, at least about 97%, at least about 98%, or at least about 99% of the total mUFAs or derivatives thereof. In a further embodiment, the recombinant proteobacterium may produce greater than 90% non-native mUFA or derivatives thereof, such as ω-5 unsaturated fatty acids or derivatives thereof. In particular, the mUFA or derivative thereof may be one or more of z9-tetradecenoic acid, z11-hexadecenoic acid, and z13-octadecenoic acid. Alternatively, the mUFA or derivative thereof may be one or more of z9-tetradecenol, z11-hexadecenol, z13-octadecenol, z7-tetradecenol, z9-hexadecenol and z11-octadecenol.

In a particular embodiment, the recombinant proteobacterium comprises a heterologous acyl-ACP desaturase, a heterologous acyl-ACP thioesterase, and a heterologous ferredoxin, wherein the native dual 3-hydroxy acyl-ACP dehydratase/isomerase (FabA) is deleted. In another embodiment, the recombinant proteobacterium overexpresses endogenous flavodoxin reductase or ferredoxin reductase (e.g., with a robust constitutive promoter) or expresses heterologous ferredoxin reductase or heterologous flavodoxin reductase.

In another particular embodiment, the recombinant proteobacterium comprises a heterologous acyl-ACP desaturase, a heterologous acyl-ACP thioesterase, and a heterologous 3-hydroxy acyl-ACP-dehydratase (FabZ), and optionally a heterologous ferredoxin and flavodoxin reductase or ferredoxin reductase, wherein the native dual 3-hydroxy acyl-ACP dehydratase/isomerase (FabA) is deleted.

In another particular embodiment, the recombinant proteobacterium comprises an increased level of FadR polypeptide expression. In this embodiment, the increased FadR expression may be native FadR, heterologous FadR, endogenous FadR, or heterologous and endogenous FadR. In another embodiment, the recombinant proteobacterium comprises an increased level of DNA binding activity of FadR as compared to a corresponding wildtype proteobacterium wherein the FadR is present at levels normal under natural conditions.

In another particular embodiment, the recombinant proteobacterium comprises a heterologous acyl-ACP desaturase, a heterologous acyl-ACP thioesterase, and a heterologous carboxylic acid reductase, and optionally a heterologous ferredoxin, heterologous flavodoxin reductase or ferredoxin reductase, and/or a heterologous 3-hydroxy acyl-ACP-dehydratase (FabZ), wherein the native dual 3-hydroxy acyl-ACP dehydratase/isomerase (FabA) is deleted. In a further embodiment, this recombinant proteobacterium produces an unsaturated fatty aldehyde or an unsaturated fatty alcohol. The unsaturated fatty aldehyde or unsaturated fatty alcohol may be z9-tetradecenal, z11-hexadecenal, z13-octadececanal, z9-tetradecenol, z11-hexadecenol, z13-octadececanol, and a combination thereof.

In another particular embodiment, the recombinant proteobacterium comprises a heterologous acyl-ACP desaturase, a heterologous acyl-ACP thioesterase, a heterologous carboxylic acid reductase and a heterologous alcohol dehydrogenase, and optionally one or more of a heterologous ferredoxin, a heterologous flavodoxin reductase or ferredoxin reductase, and a heterologous 3-hydroxy acyl-ACP-dehydratase (FabZ), wherein the native dual 3-hydroxy acyl-ACP dehydratase/isomerase (FabA) is deleted.

In another particular embodiment, the recombinant proteobacterium comprises a heterologous acyl-ACP desaturase, a heterologous acyl-ACP thioesterase, a heterologous carboxylic acid reductase, and a heterologous phosphopantetheinyl transferase, and optionally one or more of a heterologous ferredoxin, a heterologous flavodoxin reductase or ferredoxin reductase, a heterologous 3-hydroxy acyl-ACP-dehydratase (FabZ), and a heterologous alcohol dehydrogenase wherein the native dual 3-hydroxy acyl-ACP dehydratase/isomerase (FabA) is deleted.

In another particular embodiment, the recombinant proteobacterium comprises a heterologous acyl-ACP desaturase, a heterologous acyl-ACP thioesterase, a heterologous carboxylic acid reductase, and a heterologous alcohol acetyl-CoA transferase, and optionally one or more of a heterologous ferredoxin, a heterologous flavodoxin reductase or ferredoxin reductase, a heterologous 3-hydroxy acyl-ACP-dehydratase (FabZ), a heterologous alcohol dehydrogenase, and a heterologous phosphopantetheinyl transferase, wherein the native dual 3-hydroxy acyl-ACP dehydratase/isomerase (FabA) is deleted. In a particular embodiment, the recombinant proteobacterium comprises a heterologous acyl-ACP desaturase, a heterologous acyl-ACP thioesterase, a carboxylic acid reductase, and a heterologous alcohol acetyl-CoA transferase. In a further embodiment, this recombinant proteobacterium produces an unsaturated fatty alcohol acetate. The unsaturated fatty alcohol acetate may be consisting of z9-tetradecenyl acetate, z11-hexadecenyl acetate, z13-octadecenyl acetate, or a combination thereof.

In another particular embodiment, the recombinant proteobacterium comprises a heterologous acyl-ACP desaturase, a heterologous acyl-ACP thioesterase, and a heterologous ω-hydroxylase, and optionally one or more of a heterologous ferredoxin, a heterologous flavodoxin reductase or ferredoxin reductase, a heterologous 3-hydroxy acyl-ACP-dehydratase (FabZ), a heterologous carboxylic acid reductase, a heterologous alcohol dehydrogenase, a heterologous phosphopantetheinyl transferase, and a heterologous alcohol acetyl-CoA transferase, wherein the native dual 3-hydroxy acyl-ACP dehydratase/isomerase (FabA) is deleted. In a further embodiment, this recombinant proteobacterium produces an unsaturated ω-hydroxy fatty acid. The unsaturated ω-hydroxy fatty acid may be (z9)14-hydroxy-tetradecenoic acid, (z11)16-hydroxy-hexadecenoic acid, (z13)18-hydroxy-octadecenoic acid, or a combination thereof.

In another particular embodiment, the recombinant proteobacterium comprises a heterologous acyl-ACP desaturase, a heterologous acyl-ACP thioesterase, and a heterologous alcohol oxidase/dehydrogenase and optionally one or more of a heterologous ferredoxin, a heterologous 3-hydroxy acyl-ACP-dehydratase (FabZ), a heterologous carboxylic acid reductase, a heterologous alcohol dehydrogenase, a heterologous phosphopantetheinyl transferase, a heterologous alcohol acetyl-CoA transferase, and a heterologous ω-hydroxylase, wherein the native dual 3-hydroxy acyl-ACP dehydratase/isomerase (FabA) is deleted.

In another particular embodiment, the recombinant proteobacterium comprises a heterologous acyl-ACP desaturase, a heterologous acyl-ACP thioesterase, and a heterologous aldehyde dehydrogenase, and optionally one or more of a heterologous ferredoxin, a heterologous 3-hydroxy acyl-ACP-dehydratase (FabZ), a heterologous carboxylic acid reductase, a heterologous alcohol dehydrogenase, a heterologous phosphopantetheinyl transferase, a heterologous alcohol acetyl-CoA transferase, a heterologous ω-hydroxylase, and a heterologous alcohol oxidase/dehydrogenase, wherein the native dual 3-hydroxy acyl-ACP dehydratase/isomerase (FabA) is deleted. In a further embodiment, this recombinant proteobacterium produces an unsaturated α/ω-dicarboxylic acid. The unsaturated α/ω-dicarboxylic acid may be (z5)1,14-tetradecenedioic acid, (z5)1,16-hexadecenedioic acid, (z5)1,18-octadecenedioic acid, or a combination thereof.

In a specific embodiment, the recombinant proteobacterium comprises a heterologous acyl-ACP desaturase, a heterologous acyl-ACP thioesterase, a heterologous 3-hydroxy acyl-ACP-dehydratase (FabZ), a heterologous ferredoxin, and a heterologous flavodoxin reductase or ferredoxin reductase, and wherein the native dual 3-hydroxy acyl-ACP dehydratase/isomerase (FabA) is deleted.

In another particular embodiment, the recombinant proteobacterium produces non-native mUFAs and a heterologous acyl-ACP desaturase, a heterologous ferredoxin, a heterologous flavodoxin reductase or a heterologous ferredoxin reductase, a heterologous carboxylic acid reductase, and a heterologous 3-hydroxy-acyl-ACP dehydratase, wherein the native dual 3-hydroxy acyl-ACP dehydratase/isomerase (FabA) is deleted or attenuated. Additionally, the recombinant proteobacterium may comprise a heterologous acetyl-CoA transferase.

In another particular embodiment, the recombinant proteobacterium produces non-native mUFAs and comprises a heterologous acyl-ACP desaturase, a heterologous ferredoxin, a heterologous flavodoxin reductase or a heterologous ferredoxin reductase, a heterologous acyl-ACP reductase and a heterologous alcohol dehydrogenase, wherein the native dual 3-hydroxy acyl-ACP dehydratase/isomerase (FabA) is deleted or attenuated.

In another particular embodiment, the recombinant proteobacterium produces non-native mUFAs and comprises a heterologous acyl-ACP desaturase, a heterologous ferredoxin, a heterologous flavodoxin reductase or a heterologous ferredoxin reductase, a heterologous $\omega$-hydroxylase, and a heterologous 3-hydroxy-acyl-ACP dehydratase, wherein the native dual 3-hydroxy acyl-ACP dehydratase/isomerase (FabA) is deleted or attenuated. Additionally, the recombinant proteobacterium may comprise a heterologous alcohol dehydrogenase and/or a heterologous aldehyde dehydrogenase.

In a specific embodiment, the recombinant proteobacterium produces non-native mUFAs and comprises a heterologous acyl-ACP desaturase, a heterologous acyl-ACP thioesterase, a heterologous ferredoxin, and a heterologous $\beta$-ketoacyl-ACP-synthase, and wherein the native dual 3-hydroxy acyl-ACP dehydratase/isomerase (FabA) is deleted. Additionally or alternatively, the recombinant proteobacterium has an increased level of expression of endogenous $\beta$-ketoacyl-ACP-synthase as compared to a corresponding wild type proteobacterium. For example, non-native $\omega$5-unsaturated fatty acid derivatives that may be produced include z9-tetradecenoic acid, z11-hexadecenoic acid and/or z13-octadecenoic acid.

In a specific embodiment, the recombinant proteobacterium produces unsaturated fatty alcohols and comprises a heterologous acyl-ACP desaturase, a heterologous acyl-ACP thioesterase, a heterologous carboxylic acid reductase, a heterologous alcohol dehydrogenase, a heterologous phosphopantetheinyl transferase, a heterologous ferredoxin, and a heterologous $\beta$-ketoacyl-ACP-synthase, and wherein the native dual 3-hydroxy acyl-ACP dehydratase/isomerase (FabA) is deleted. For example, the fatty alcohols z9-tetradecenol, z11-hexadecenol and/or z13-octadecenol may be produced.

In a specific embodiment, the recombinant proteobacterium produces $\omega$-hydroxy fatty acids and comprises a heterologous acyl-ACP desaturase, a heterologous acyl-ACP thioesterase, a heterologous ferredoxin, and a heterologous $\beta$-ketoacyl-ACP-synthase, and wherein the native dual 3-hydroxy acyl-ACP dehydratase/isomerase (FabA) is deleted. For example, the $\omega$-hydroxy fatty acids (z9)14-hydroxy-tetradecenoic acid, (z11)16-hydroxy-hexadecenoic acid and/or (z13)18-hydroxy-octadecenoic acid may be produced.

In a specific embodiment, the recombinant proteobacterium produces fatty alcohol acetate esters and comprises a heterologous acyl-ACP desaturase, a heterologous acyl- ACP thioesterase, a heterologous carboxylic acid reductase, a heterologous ferredoxin, and a heterologous acetyl-CoA transferase, and wherein the native dual 3-hydroxy acyl-ACP dehydratase/isomerase is (FabA) deleted. For example, the fatty alcohol acetates z9-tetradecenyl acetate, z11-hexadecenyl acetate and/or z13-octadecenyl acetate may be produced.

In a specific embodiment, the recombinant proteobacterium produces fatty aldehydes and comprises a heterologous acyl-ACP desaturase, a heterologous acyl-ACP thioesterase, a carboxylic acid reductase, a heterologous ferredoxin and has one more deletions in alcohol dehydrogenase and/or aldehyde reductase genes. For example, the fatty aldehydes z11-hexadecenal, z9-tetradecenal and/or z13-octadecenal) may be produced.

In a specific embodiment, the recombinant proteobacterium produces $\alpha$/$\omega$-dicarboxylic acids and comprises a heterologous acyl-ACP desaturase, a heterologous acyl-ACP thioesterase, a heterologous alcohol dehydrogenase, a heterologous $\omega$-hydroxylase, and a heterologous aldehyde dehydrogenase, and wherein the native dual 3-hydroxy acyl-ACP dehydratase/isomerase (FabA) is deleted. For example, the $\alpha$/$\omega$-dicarboxylic acids (z5)1,14-tetradecendioic acid, (z5)1,16-hexadecendioic acid and/or (z5)1,18-octadecendioic acid may be produced.

In a specific embodiment, the recombinant proteobacterium produces non-native monounsaturated free fatty acids and comprises a heterologous acyl-ACP desaturase, a heterologous ferredoxin, a heterologous flavodoxin reductase or a heterologous ferredoxin reductase, a heterologous carboxylic acid reductase, and a heterologous 3-hydroxy-acyl-ACP dehydratase, and wherein the native dual 3-hydroxy acyl-ACP dehydratase/isomerase (FabA) is deleted or attenuated.

In a specific embodiment, the recombinant proteobacterium produces non-native monounsaturated fatty aldehyde and/or fatty alcohol and comprises a heterologous acyl-ACP desaturase, a heterologous ferredoxin, a heterologous flavodoxin reductase or a heterologous ferredoxin reductase, a heterologous acyl-ACP reductase and a heterologous alcohol dehydrogenase, and wherein the native dual 3-hydroxy acyl-ACP dehydratase/isomerase (FabA) is deleted or attenuated In a specific embodiment, the recombinant proteobacterium produces $\omega$-hydroxy fatty acids and comprises a heterologous acyl-ACP desaturase, a heterologous ferredoxin, a heterologous flavodoxin reductase or a heterologous ferredoxin reductase, a heterologous $\omega$-hydroxylase, and a heterologous 3-hydroxy-acyl-ACP dehydratase, and wherein the native dual 3-hydroxy acyl-ACP dehydratase/isomerase (FabA) is deleted or attenuated.

In some exemplary embodiments, the host cell (e.g., a recombinant proteobacterium) may further comprise genetic manipulations and alterations to enhance or otherwise fine tune the production of non-native mUFAs or derivatives thereof. The optional genetic manipulations can be used interchangeably from one host cell to another, depending on what other heterologous enzymes and what native enzymatic pathways are present in the host cell. Some optional genetic manipulations include one or more of the following:

FadE (Acyl-CoA dehydrogenase) catalyzes the first step in fatty acid utilization/degradation ($\beta$-oxidation cycle) which is the oxidation of acyl-CoA to 2-enoyl-CoA (see e.g., Campbell, J. W. and Cronan, J. E. Jr (2002) *J. Bacteriol.* 184(13): 3759-3764, Lennen, R. M. and Pfleger, B. F (2012) Trends Biotechnol. 30(12):659-667). Since FadE initiates the $\beta$-oxidation cycle, when *E. coli* lacks FadE, it cannot grow on fatty acids as a carbon source (see e.g., Campbell, J. W. and Cronan supra). The same effect can be achieved by attenuating other enzymes from the β-oxidation cycle, e.g., FadA, which is a 3-ketoacyl-CoA thiolase, or FadB, which is a dual 3-hydroxyacyl-CoA-dehydrogenase/dehydratase.

However, when *E. coli* is grown on a carbon source other than fatty acids e.g., grown on sugar, acetate, etc., FadE attenuation is optional because under such conditions FadE expression is repressed by FadR. Therefore, when cells are grown on a simple carbon source such as e.g., glucose, the FadE gene product is already attenuated. Accordingly, when grown on a carbon source other than fatty acids, a FadE mutation/deletion is optional.

In some embodiments, the fatty acid biosynthetic pathway in the production host uses the precursors acetyl-CoA and malonyl-CoA. *E. coli* or other host organisms engineered to overproduce these components can serve as the starting point for subsequent genetic engineering steps to provide the specific output product (such as, fatty acids, fatty esters, hydrocarbons, fatty alcohols). Several different modifications can be made, either in combination or individually, to the host strain to obtain increased acetyl-CoA/malonyl-CoA/fatty acid and fatty acid derivative production. See, for example, U.S. Patent Application Publication 2010/0199548, which is incorporated herein by reference in its entirety.

Other exemplary modifications of a host cell include, e.g., overexpression of non-native and/or native and/or variants of genes involved in the synthesis of acyl-ACP. In general, increasing acyl-ACP synthesis increases the amount of acyl-ACP, which is the substrate of thioesterases, ester synthases and acyl-ACP reductases. Exemplary enzymes that increase acyl-ACP production include e.g., enzymes that make up the "fatty acid synthase" (FAS). As is known in the art (see e.g., U.S. 2010/0199548) FAS enzymes are a group of enzymes that catalyze the initiation and elongation of acyl chains. The acyl carrier protein (ACP) along with the enzymes in the FAS pathway control the length, degree of saturation, and branching of the fatty acids produced. FAS pathway enzymes FabA, FabB, FabZ, and FadR are discussed above. Additional enzymes that comprise FAS include e.g., AccABCD, FabD, FabH, FabG, FabI, FabK, FabL, FabM, FabQ, FabV, FabX, and FabF. Depending upon the desired product one or more of these genes can be attenuated or over-expressed.

In some embodiments, a host strain may overexpress one or more of the FAS genes. Exemplary FAS genes that may be overexpressed include e.g., FadR from *Escherichia coli* (NP_415705.1), FabB from *Escherichia coli* (P0A953) or FabZ from *Acinetobacter* baylyi (Q6FCG4). In some exemplary embodiments, the overexpression of one or more of these genes, which code for enzymes and regulators in fatty acid biosynthesis, serves to further increase the titer of fatty-acid derivative compounds under particular culture conditions.

In another embodiment, the recombinant proteobacterium is produced through adaptive evolution of a wild-type proteobacterium or a different recombinant proteobacterium. In a particular embodiment, strain sAS.561 underwent adaptive evolution to obtain sAS.571. In another embodiment, the evolved proteobacterium contains one or more mutations. In a particular embodiment, the mutation is may be a C→T mutation in the promoter region of the yibL gene, which may up or down regulate the expression of the YibL gene product; a 18 bp in-frame insertion into the ptsI gene, which may effect PtsI expression and/or activity; and an IS1 mediated 65 bp insertion into the upstream region of the uof gene, which has been implicated in the translation of Fur, the major regulator of gene expression in response to iron (fur regulon). In a still further embodiment, the evolved proteobacterium comprises each of the C→T mutation in the promoter region of the yibL gene, an 18 bp in-frame insertion into the ptsI gene, and an IS1 mediated 65 bp insertion into the upstream region of the uof gene.

III. Vectors

Also described herein are vectors comprising a nucleotide sequence that encodes one or more heterologous enzymes, including one or more of a heterologous acyl-ACP desaturase, a heterologous acyl-ACP thioesterase, a heterologous ferredoxin, a heterologous 3-hydroxyacyl-ACP-dehydratase (FabZ), a heterologous carboxylic acid reductase, a heterologous alcohol dehydrogenase, a heterologous phosphopantetheinyl transferase, a heterologous alcohol acetyl-CoA transferase, a heterologous (o-hydroxylase, a heterologous alcohol oxidase/dehydrogenase, a heterologous fatty acid metabolism regulator protein (fadR), a heterologous aldehyde hydrogenase, and a heterologous β-ketoacyl-ACP synthase. For example a vector comprising a nucleotide sequence encoding a Δ9-tetradecanoyl-acyl-ACP desaturase having at least 85%, at least 90%, at least 95% or 100% sequence identity to SEQ ID NO: 12 may be constructed by methods well known in the art.

The nucleotide sequence encoding the one or more enzymes, such as Δ9-tetradecanoyl-acyl-ACP desaturase, may be operably linked to one or more heterologous regulatory elements. Where the vector comprises a nucleotide sequence encoding more than one of the enzymes recited above, the vector may comprise a single heterologous regulatory element that directs expression of both enzymes or multiple heterologous regulatory elements that independently directs expression of each of the enzymes encoded by the vector.

As noted above, a polynucleotide or polypeptide can be overexpressed using methods well known in the art. In some embodiments, overexpression of a polypeptide is achieved by the use of an exogenous regulatory element. The term "exogenous regulatory element" generally refers to a regulatory element originating outside of the host cell. However, in certain embodiments, the term "exogenous regulatory element" can refer to a regulatory element derived from the host cell whose function is replicated or usurped for the purpose of controlling the expression of an endogenous polypeptide. For example, if the host cell is an *E. coli* cell, and the FadR polypeptide is encoded by an endogenous fadR gene, then expression of the endogenous fadR can be controlled by a promoter derived from another *E. coli* gene.

In some embodiments, the exogenous regulatory element is a chemical compound, such as a small molecule. As used herein, the term "small molecule" refers to a substance or compound having a molecular weight of less than about 1,000 g/mol.

In some embodiments, the exogenous regulatory element is an expression control sequence which is operably linked to the endogenous gene by recombinant integration into the genome of the host cell. In certain embodiments, the expression control sequence is integrated into a host cell chromosome by homologous recombination using methods well known in the art (e.g., Datsenko et al., *Proc. Natl. Acad. Sci. U.S.A.*, 97(12): 6640-6645 (2000)).

In some embodiments, a vector described herein comprises a promoter operably linked to the polynucleotide sequence. In certain embodiments, the promoter is a developmentally-regulated promoter, an organelle-specific promoter, a tissue-specific promoter, an inducible promoter, a constitutive promoter, or a cell-specific promoter.

In some embodiments, a vector described herein comprises at least one sequence which may be (a) an expression control sequence (or regulatory element) operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence.

The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

Expression of genes encoding polypeptides in prokaryotes, for example, E. coli, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech, Inc., Piscataway, NJ; Smith et al., Gene, 67: 31-40 (1988)), pMAL (New England Biolabs, Beverly, MA), and pRITS (Pharmacia Biotech, Inc., Piscataway, N.J.), which fuse glutathione S-transferase (GST), maltose E binding protein, or protein A, respectively, to the target recombinant polypeptide.

Suitable expression systems for both prokaryotic and eukaryotic cells are well known in the art; see, e.g., Sambrook et al., "Molecular Cloning: A Laboratory Manual," second edition, Cold Spring Harbor Laboratory (1989). Examples of inducible, non-fusion E. coli expression vectors include pTrc (Amann et al., Gene, 69: 301-315 (1988)) and PET 11d (Studier et al., Gene Expression Technology: Methods in Enzymology 185, Academic Press, San Diego, CA, pp. 60-89 (1990)). In certain embodiments, a polynucleotide sequence of the invention is operably linked to a promoter derived from bacteriophage T5. Examples of vectors for expression in yeast include pYepSec1 (Baldari et al., EMBO J., 6: 229-234 (1987)), pMFa (Kurjan et al., Cell, 30: 933-943 (1982)), pJRY88 (Schultz et al., Gene, 54: 113-123 (1987)), pYES2 (Invitrogen Corp., San Diego, CA), and picZ (Invitrogen Corp., San Diego, CA). Baculovirus vectors available for expression of proteins in cultured insect cells (e.g., Sf9 cells) include, for example, the pAc series (Smith et al., Mol. Cell Biol., 3: 2156-2165 (1983)) and the pVL series (Lucklow et al., Virology, 170: 31-39 (1989)). Examples of mammalian expression vectors include pCDM8 (Seed, Nature, 329: 840 (1987)) and pMT2PC (Kaufinan et al., EMBO J., 6: 187-195 (1987)).

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in, for example, Sambrook et al. (supra).

For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Similarly, for stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to an antibiotic) can be introduced into the host cells along with the gene of interest. Preferred selectable markers include those which confer resistance to drugs, such as G418, hygromycin, and methotrexate. Nucleic acids encoding a selectable marker can be introduced into a host cell on the same vector as that encoding a polypeptide described herein or can be introduced on a separate vector. Cells stably transfected with the introduced nucleic acid can be identified by growth in the presence of an appropriate selection drug.

IV. Methods of Producing Non-Native mUFAs or Derivatives Thereof, Cell Cultures and Fatty Acid Compositions Methods of producing non-native mUFAs or derivatives thereof, cell cultures and fatty acid compositions are also described herein.

The recombinant proteobacterium described herein can be used to produce mUFAs or derivatives thereof, particularly ω-5 mUFAs or derivatives thereof. Thus, in one embodiment, a method is provided herein comprising culturing a recombinant proteobacterium comprising an acyl-ACP desaturase and an acyl-ACP thioesterase, wherein a native dual 3-hydroxy acyl-ACP dehydratase/isomerase (FabA) is deleted or attenuated in or on a suitable carbon source. As described above, the recombinant proteobacterium may further comprise one or more enzymes, such as a ferredoxin, flavodoxin reductase or ferredoxin reductase, a 3-hydroxyacyl-ACP-dehydratase (FabZ), a carboxylic acid reductase, an alcohol dehydrogenase, a phosphopantetheinyl transferase, an alcohol acetyl-CoA transferase, a ω-hydroxylase, an alcohol oxidase/dehydrogenase, a fatty acid metabolism regulator protein (fadR), an aldehyde hydrogenase, and a β-ketoacyl-ACP synthase. These enzymes may be native or heterologous, endogenous or exogenous. The recombinant proteobacterium may also comprise a heterologous dual 3-hydroxy acyl-ACP dehydratase/isomerase (FabA).

In general, non-native mUFAs and/or derivatives thereof are prepared by growing and/or fermenting the recombinant proteobacteria on or in suitable a carbon source. The recombinant proteobacteria are grown and/or fermented under appropriate conditions for a sufficient period of time to produce mUFAs and/or derivatives thereof. The carbon source may be culture media that comprises carbohydrates (e.g., monosaccharides, oligosaccharides, and polysaccharides), supplements (e.g., amino acids, antibiotics, polymers, acids, alcohols, aldehydes, ketones, peptides, and gases), and mineral salts. In a particular embodiment the carbon source is LB media or nitrogen (N)-mineral media with glucose as a carbon source.

Thus, also provided herein is a cell culture comprising the recombinant proteobacteria described herein and one or more mUFAs or derivatives thereof. Additionally provided herein is a fatty acid composition produced by the recombinant proteobacterium as described herein.

In some embodiments, the mUFA or derivative thereof is placed in a composition comprising the mUFA or derivative thereof, wherein the mUFA or derivative thereof is prepared by culturing and/or fermenting the recombinant proteobacterium. In some embodiments, the composition comprises one or more than one (e.g., two, three, four, five, or more) mUFA or derivative thereof.

Additionally, a composition is provided herein comprising more ω-5 unsaturated fatty acids or derivatives thereof than ω-7 unsaturated fatty acids derivatives thereof. The composition may be produced by the recombinant proteobacterium disclosed herein, and the compositions may comprise unsaturated fatty acids or other derivatives such as fatty acids, fatty acid esters, FAME, FAEE, FACE, fatty amines, fatty aldehydes, fatty alcohols, hydrocarbons, ketones, terminal olefins, internal olefin, 3-hydoxy fatty acid derivatives, bifunctional fatty acid derivatives, and unsaturated fatty acid derivatives as disclosed herein. For example, a composition may comprise at least about 5% more, at least about 10% more, at least about 15% more, at least about 20% more, at least about 25% more, at least about 30% more, at least about 35% more, at least about 40% more, at least about 45% more, at least about 50% more, at least about 55% more, at least about 60% more, at least about 65% more, at least about 70% more, at least about 75% more, at least about 80% more, at least about 85% more, at least about 90% more, at least about 95% more, or at least about 99% more ω-5 unsaturated fatty acids or derivatives thereof than ω-7 unsaturated fatty acids or derivatives thereof based on the total weight of the composition. Alternatively, the composition comprises ω-5 unsaturated fatty acids or derivatives thereof and no or substantially no ω-7 unsaturated fatty acids or derivative thereof (e.g., only trace amounts of ω-7 unsaturated fatty acids or derivatives thereof).

In another embodiment, a composition may comprise at least about 55%, at least about 60%, at least about 65%, at least about 70%, at least about 80%, at least about 85%, at least about 90%, at least about 95%, or at least about 99% ω-5 unsaturated fatty acids or derivatives thereof based on the total weight of the composition. Additionally, a composition may comprise about 50% or less, about 45% or less, about 40% or less, about 35% or less, about 30% or less, about 25% or less, about 20% or less, about 15% or less, about 10% or less, about 5% or less, about 4% or less, about 3% or less, about 2% or less, about 1% or less, or substantially no ω-7 unsaturated fatty acids or derivatives thereof based on the total weight of the composition.

Examples of mixture ratios of ω-5 unsaturated fatty acids or derivatives to ω-7 unsaturated fatty acids or derivatives thereof for the compositions provided herein include, but are not limited to, 55%/45%, 60%/40%, 65%/35%, 70%/30%, 75%/25%, 80%/20%, 85%/15%, 90%/10%, 95%/5%, 96%/4%, 97%/3%, 98%/2%, 99%/1%, wherein the first percentage value is the % of ω-5 unsaturated fatty acids or derivatives and the second percentage value is the % ω-7 unsaturated fatty acids or derivatives in the composition. Alternatively, the composition may comprise no or only trace amounts of the ω-7 unsaturated fatty acids.

In a particular example, the composition may comprise more ω-5 unsaturated fatty alcohols than ω-7 unsaturated fatty alcohols, e.g. about 90% of ω-5 unsaturated fatty alcohols and 10% ω-7 unsaturated fatty alcohols (e.g. 80% of z11-hexadecenol and 10% of z13-octadecenol and 10% of z9-hexadecenol).

In another particular example, the composition may comprise more ω-5 unsaturated fatty acids than ω-7 unsaturated fatty acids, e.g., about 95% of ω-5 unsaturated fatty acids, and 5% ω-7 unsaturated fatty acids. In another embodiment, the composition may comprise about 99%, or greater than 99% of ω-5 unsaturated fatty acids (e.g. z11-hexadecenoic acid and z9-tetradecenoic acid) and about 1% or less than 1% ω-7 unsaturated fatty acids. In still another embodiment, the composition may comprise essentially only ω-5 unsaturated fatty acids and no or only trace amounts of ω-7 unsaturated fatty acids.

V. Uses

The recombinant proteobacterium described herein can be used for a variety of purposes. In particular, the recombinant proteobacterium may be used to produce insect pheromones or precursors thereof, and also for producing fragrances or precursors thereof.

In some embodiments, the mUFA or derivative thereof prepared by the cultured and/or fermented recombinant proteobacterium is used in a composition. In some embodiments, the mUFA or derivative thereof is a fermentation product of the recombinant proteobacterium. In other embodiments, the composition comprises one or more than one (e.g., two, three, four, five, or more) particular species of mUFA or derivative thereof. In a particular embodiment, the composition is an insect pheromone or precursor thereof, or a fragrance or a precursor thereof. In a particular embodiment, the mUFA or derivative thereof is purified.

In some embodiments, the mUFA or derivative thereof is prepared at a time and/or location that is different than when the composition is prepared. For example, the mUFA or derivative thereof may be produced by the recombinant proteobacterium in one location (e.g., a first facility, city, state, or country), transported to another location (e.g., a second facility, city, state, or country) and incorporated into the composition comprising the mUFA or derivative thereof.

In some embodiments, the mUFA or derivative thereof is purified prior to its use in the composition. The mUFA or derivative may be purified to a purity of at least about 60% free (e.g., at least about 65% free, at least about 70% free, at least about 75% free, at least about 80% free, at least about 85% free, at least about 90% free, at least about 95% free, at least about 96% free, at least about 97% free, at least about 98% free, or at least about 99% free) from other components with which they are associated.

In some embodiments, the mUFA or derivatives thereof are insoluble or highly insoluble in water. In such cases, the mUFA or derivatives thereof are in a separate phase from the environment in which the recombinant proteobacteria reside (e.g., fermentation broth). In some embodiments, the mUFA or derivatives thereof are solid at room temperature. In another embodiment, the mUFA or derivatives thereof (e.g., alcohol derivatives) are liquid.

In a particular embodiment, purification of the mUFA or derivatives thereof involve isolating and recovering long chain alcohols. The product of the fermentation may be a heterogeneous mixture of a solid phase constituted by the biomass, the water phase of the fermentation broth, and a light liquid organic phase constituted by the secreted product. The separation of these phases can be achieved by centrifugation. Either disk-stack nozzle centrifuges or disk-stack ejector centrifuges can be used efficiently in different configurations. Typically, when using ejector machines, a 2-stage centrifugation scheme is recommended to achieve high clarity in the light phase (product) while minimizing losses. A nozzle centrifuge offers better clarification of the product in a single step centrifugation, but a more careful tuning of broth conditioning and centrifugation conditions may be required. In both cases, some conditioning of the fermentation broth (pH and temperature adjustments for example) may be desired to improve the overall performance of the centrifuges.

The light phase recovered is a crude organic phase composed by a mixture of fatty alcohols with a composition defined by the performance of the microorganism in use. This crude material can be further cleaned up by water-washing to remove any water-soluble compounds that might have been carried over, followed by water separation (centrifugation or gravity settling) and drying.

Additional purification steps may be required depending on the final product applications and specifications. These steps may include saponification, bleaching, and eventually distillation if high purity of a single chain length is required. All these are standard unit operations used regularly in the industry.

In another particular embodiment, purification of the mUFA or derivatives thereof involve isolating and recovering fatty acids. Purification of fatty acids differs from the separation of alcohols in that the fatty acids mixed with the biomass are both solids.

Two different approaches can be applied:

One approach includes recovery of the solid phase of biomass plus product via decanting centrifugation, followed by solvent extraction of the product from the biomass with an appropriate solvent (i.e., methanol or ethanol). The fatty acids dissolve in the solvent and the biomass is removed either by centrifugation or filtration. The recovery of the fatty acids is then completed by evaporating the solvent. Depending on the application the product can be further used as a solution in the solvent or as a solid. Other purification steps including distillation could be applied to meet final specifications.

Another approach includes recovery of the product via whole broth extraction with a water immiscible solvent. In this approach, the fermentation broth is contacted in either batch or continuous schemes with an appropriate solvent (i.e., butyl acetate, medium chain alcohols, or esters) to allow for the complete dissolution of the product in the solvent. The light organic solvent phase can be separated from the water phase in a similar way as those described for the recovery of the long chain alcohols. Once a clear solvent phase has been obtained, the final product is again recovered by solvent evaporation.

In another embodiment, the mUFA or derivative thereof prepared by the recombinant proteobacterium, or a composition comprising the mUFA or derivative thereof prepared by the recombinant proteobacterium is incorporated into a product. This product is made by combining, mixing, or otherwise using the mUFA or derivative thereof produced by the recombinant proteobacterium in combination with other or more additional components to prepare the product. The product may comprise one or more than one (e.g., two, three, four, five, or more) mUFA or derivative thereof prepared by the recombinant proteobacterium. In a particular embodiment, the product is a pheromone or precursor thereof, a fragrance or precursor thereof, or a nutritional supplement or precursor thereof.

Insect Pheromones and Precursors Thereof in Crop Protection

Rising global demand for food combined with a growing concern about the environmental effects of overusing often toxic insecticides has magnified the need for more natural and sustainable means of crop protection such as insect pheromones, and precursors thereof, which are often mUFAs or derivatives thereof. The use of insect pheromones is a natural and non-toxic way of pest control and has gained attraction in agriculture in recent years. Insect pheromones can be used as lures in insect traps or sprayed on crops for insect mating disruption. However, so far synthetic pheromones are expensive to produce and are mostly synthesized from petroleum-derived feedstocks by sometimes complicated and/or low yielding chemical syntheses. Thus, in one embodiment, the recombinant proteobacterium described herein can be used for producing insect pheromones or pheromone precursors.

The insect pheromones or precursors thereof produced by the recombinant proteobacteria described herein may include derivatives of ω-5 unsaturated non-native fatty acids such as z9-tetradecenol, z11-hexadecenol, z13-octadecenol, z9-tetradecenal, z11-hexadecenal, z13-octadecenal, z9-tetradecenyl acetate, z11-hexadecenyl acetate, and z13-octadecenyl acetate. Specific examples of insect pheromones of important crop pests include, but are not limited to, z11-hexadecenal and/or z11-hexadecenyl acetate of the American cotton bollworm, the striped rice stem borer, and the diamondback moth (pests of cruciferous vegetables); z9-tetradecenal and/or z9-tetradecenyl acetate of the fall army worm (corn pests), the coddling moth, and the leafroller; and z13-octadecenal and/or z13-octadecenyl acetate of the Southwestern corn borer and the Asiatic rice borer. All these pheromones are derivatives of ω-5 mUFAs.

Figure 1:
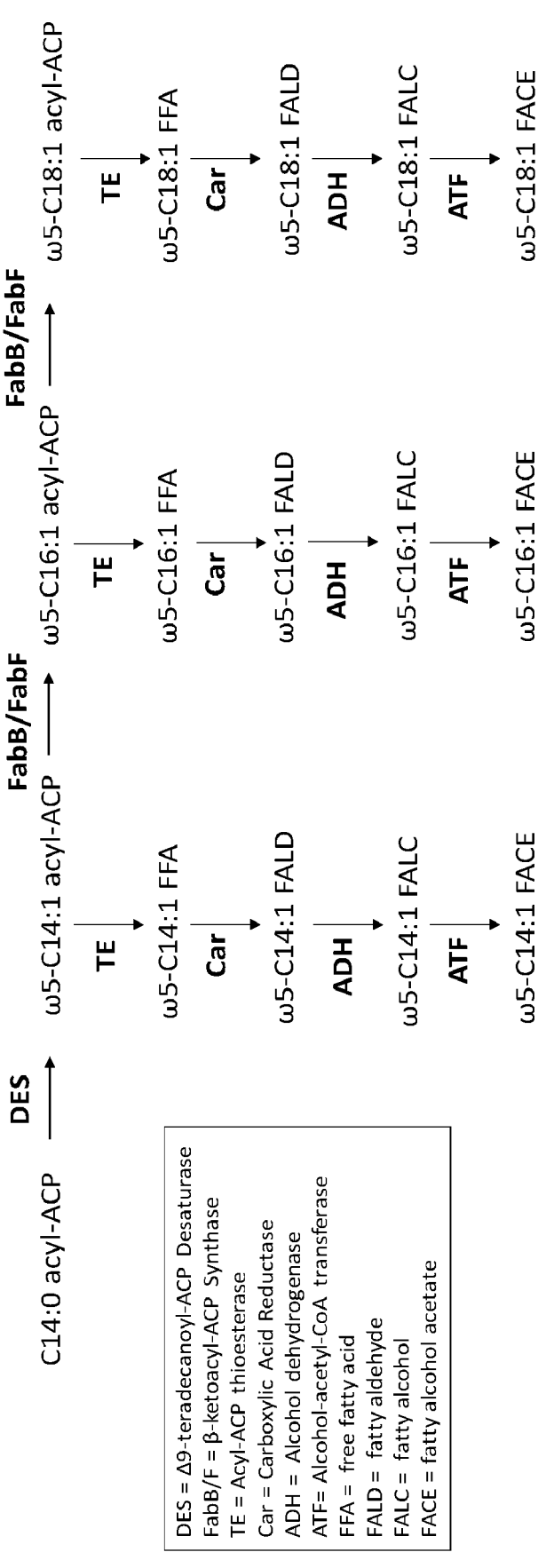
FIG. 1 depicts the bacterial biosynthetic pathway to convert acyl-ACPs to pheromones or pheromone precursors.

FIG. 1 summarizes the biochemical pathway converting bacterial acyl-ACPs to pheromones or pheromone precursors. A carboxylic acid reductase can efficiently convert the ω-5 non-native mUFA z9-tetradecenoic acid, z11-hexadecenoic acid, and z13-octadecenoic acid to the fatty aldehydes z9-tetradecenal, z11-hexadecenal, and z13-octadecenal, respectively. Particular carboxylic acid reductase or variants thereof are from *Mycobacterium smegmatis*. See WO 2010/062480 and WO 2013/152052, both of which are incorporated by reference in their entirety.

In one embodiment, the inventors have developed an efficient bacterial production system for ω-5 unsaturated pheromones or pheromone precursors that uses acyl-ACP intermediates and a novel biochemical pathway that includes a soluble Δ9-tetradecanoyl-ACP desaturase, an acyl-ACP thioesterase and a carboxylic acid reductase. The insect pheromone pathway does not contain any genes from insects and the recombinant proteobacterium has its FabA gene deleted. Therefore, only trace amounts of native ω-7 unsaturated fatty acid derivatives may be produced. For example, one recombinant strain produces ~800 mg/L of z11-hexadecenol (~80% of all fatty acid derivatives produced), but only trace amounts of z9-hexadecenol in a small-scale preparation. Thioesterase FatA from *Arabidopsis thaliana* has high specificity for acyl-ACPs with C16 chain length. Because proteobacteria (e.g., *E. coli*) have a type II fatty acid biosynthetic machinery, shorter chain acyl-ACPs are readily available in the cytoplasm for thioesterases to act upon. If FatA is replaced with e.g., an acyl-ACP thioesterase with high specificity for acyl-ACPs with C14 chain length (e.g., FatB from *Cinnamomum camphorum* or TE from *Clostridium thermocellum*), the strain may produce mainly z9-tetradecenol.

Fragrances and Precursors Thereof

Figure 2:
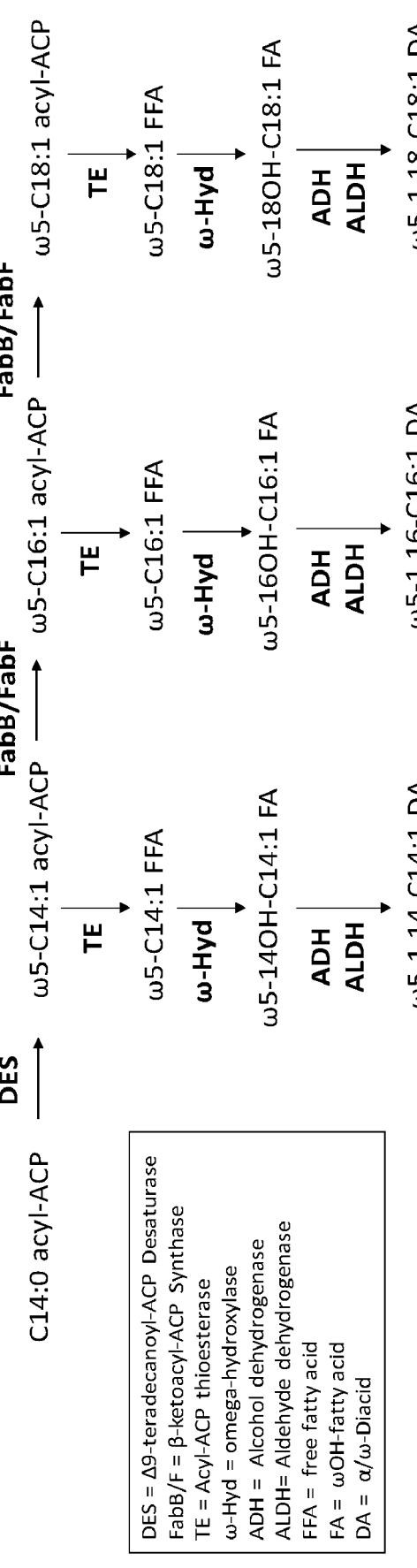
FIG. 2 depicts the bacterial biosynthetic pathway to convert acyl-ACPs to fragrances or fragrance precursors.
Figure 3B:
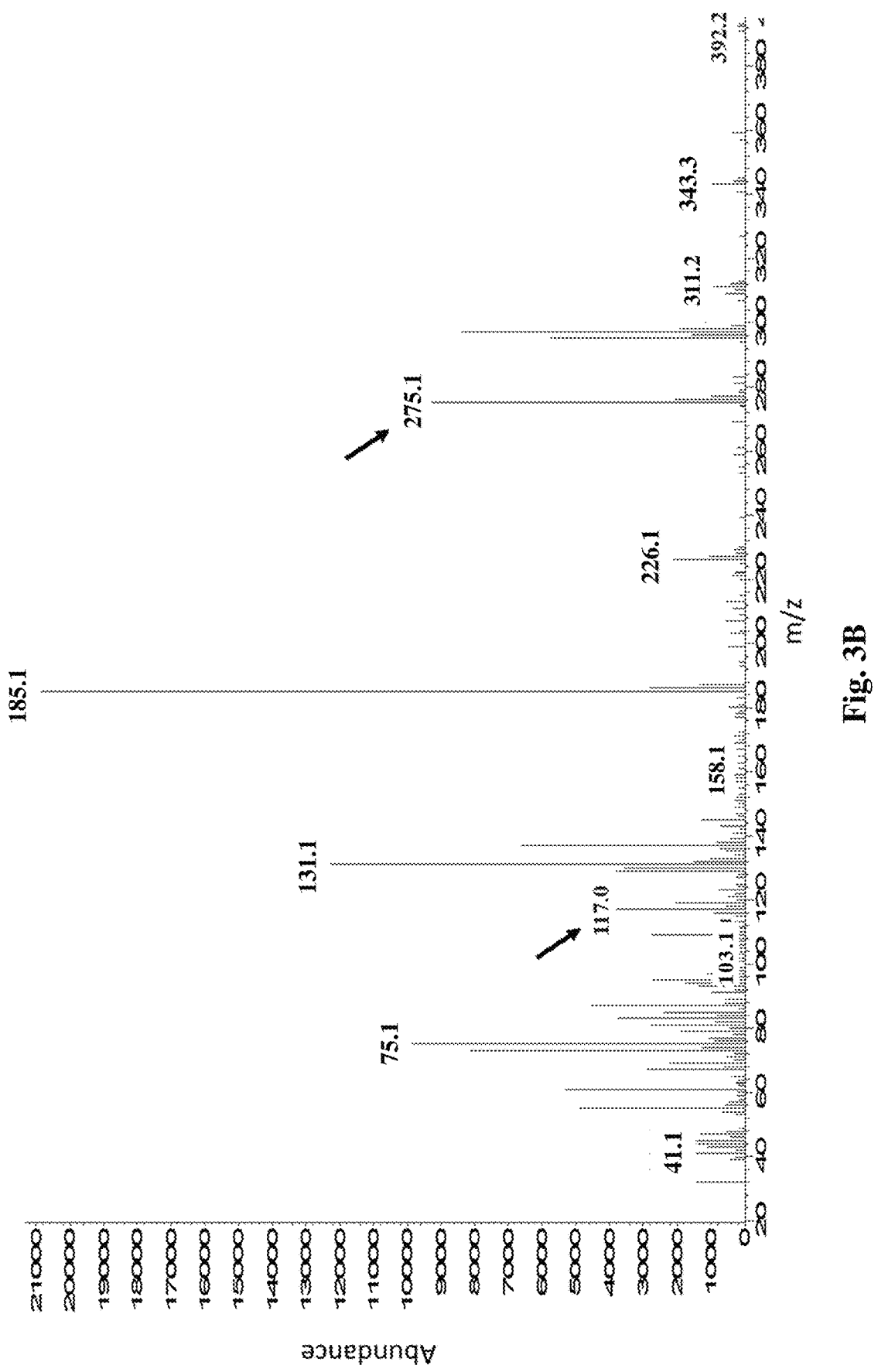
FIG. 3B depicts the mass spectrum and ion fragmentation pattern of ω-5 Δ9-tetradecenoic acid after derivatization DMDS.

Additionally or alternatively, the recombinant proteobacterium described herein may be used for producing a fragrance or fragrance precursor. FIG. 2 summarizes the biochemical pathway converting bacterial acyl-ACPs to fragrance precursors. Sometimes these may be referred to as musk fragrances.

The inventors have discovered a novel pathway that utilizes an acyl-ACP desaturase (e.g., Δ9-tetradecanoyl-ACP desaturase), an acyl-ACP thioesterase, and a ω-hydroxylase to produce musk fragrance precursors in a recombinant recombinant proteobacterium such as *E. coli*. In a particular embodiment, the ω-hydroxylase is a hybrid-fusion P450 enzyme or a variant thereof as disclosed in WO 2014/201474 and/or WO 2017/106205, which are both herein incorporated by reference in their entirety. In a further particular embodiment, the ω-hydroxylase has at least 85%, at least 90%, at least 95% or 100% sequence identity to SEQ ID NO: 22.

The fragrance precursors which may be produced by the recombinant proteobacteria described herein include derivatives of ω-5 non-native mUFAs, such as (z9)14-hydroxy-tetradecenoic acid, (z11)16-hydroxy-hexadecenoic acid (z13)18-hydroxy-octadecenoic acid, (z5)1,14-tetradecendioic acid, (z5)1,16-hexadecendioic acid, and (z5)1,18-octadecendioic acid.

In Example 6 herein the production of ω5-non-native unsaturated ω-hydroxy fatty acid is (z11)-16-hydroxy hexadecenoic acid is described. When this precursor is subjected to chemical lactonization (for methods see e.g., International Patent Application Publication WO 2015/157719 A9, which is incorporated herein by reference in its entirety), (12z)-1-Oxacycloheptadec-12-en-2-one is produced, which is structurally similar to the musk fragrances ambrettolide ((8z)-1-Oxacycloheptadec-8-en-2-one), cis-isoambrettolide ((10z)-1-Oxacycloheptadec-10-en-2-one) or isoambrettolide ((10e)-1-Oxacycloheptadec-10-en-2-one). (12z)-1-Oxacycloheptadec-12-en-2-one was reported to have a strong thibetolide-like odor similar to ambrette seeds (see U.S. Pat. No. 6,255,276), and is therefore an attractive novel musk fragrance. Hence, in one embodiment, the invention enables a cost-effective and steady supply of a natural precursor for this potential musk fragrance.

In Example 9 herein the production of the ω-5-non-native unsaturated α/ω-dicarboxylic acid (z5)1,16-hexadecene-dioic acid is described. This precursor can be chemically converted to macrocyclic ketones similar to musk ketone fragrances (for methods see e.g., International Patent Application Publication WO 2015/157719, which is incorporated herein by reference in its entirety). For example, using decarboxylative chemistry (z5)1,16-hexadecenedioic acid can be converted to the 15-membered macrocyclic ketones (5z)-cyclopentadec-5-en-1-one or (4z)-cyclopentadec-4-en-1-one. The latter is known as the musk fragrance exaltenone. Using non-decarboxylative chemistry, (z5)1,16-hexadecenedioic acid can be converted to the 16-membered macrocyclic ketones (6z)-cyclohexadec-6-en-1-one or (5Z)-cyclohexadec-5-en-1-one. The latter is known as the musk fragrance ambrettone (also know as velvione). Therefore, in another embodiment, the invention enables a cost-effective and steady supply of the natural precursor for these commercial musk fragrances.

EXAMPLES

The following examples are provided to further illustrate the invention disclosed herein but should not be construed as in any way limiting its scope.

Example 1: Small Scale Fermentation

40 μL LB culture (from an LB culture growing in a 96 well plate) was used to inoculate 360 μL LB media, which was then incubated with shaking for approximately 4 hours at 32° C. 80 μL of the LB seed was used to inoculate 320 μL N-lim media (Table 1). After growing at 32° C. for 2 hours, the cultures were induced with isopropyl β-d-1-thiogalacto-pyranoside (IPTG) (final concentration 1 mM). The cultures were then incubated at 32° C. with shaking for 20 hours (unless otherwise noted), after which they were extracted with the extraction protocol detailed below.

TABLE 1

| N-lim Media Formulation | | |
|---|---|---|
| 1 | x | 5x Salt Soln. with $NH_4Cl$ |
| 1 | x | 1000x Trace Vitamins |
| 1 | mg/L | 10 mg/mL Thiamine |
| 1 | mM | 1M $MgSO_4$ |
| 0.1 | mM | 1M $CaCl_2$ |
| 40 | g/L | 500 g/L glucose |
| 1 | x | 1000x Trace minerals |
| 10 | mg/L | 10 g/L Fe Citrate |
| 100 | μg/mL | 100 mg/ml spectinomycin |
| 100 | mM | 2M BisTris (pH7.0) |
| 0.5 | mM | Aminolevulinic acid* |

*Aminolevulinic acid is only added when ω-hydroxy fatty acids or α/ω-diacids are expected products Free Fatty Acid Species Extraction and Analytical Protocol:

To each well to be extracted 30 μL of 12M HCl, followed by 400 μL of butyl acetate containing 500 mg/L 1-undecanol as an internal standard was added when fatty alcohols were quantified or 500 mg/L undecanoic acid as an internal standard were added when fatty acids or ω-hydroxy fatty acids were quantified. The 96 well plates were then heat-sealed and shaken for 30 minutes at 2000 rpm. After shaking, the plates were centrifuged for 10 minutes at 4500 rpm at room temperature to separate the aqueous and organic layers. 50 μL of the organic layer was transferred to a 96 well plate) and derivatized with 50 μL of TMS/BSTFA. The plate was subsequently heat sealed and stored at −20° C. until evaluated by either GC-FID or GC-MS.

Fatty acids or (w-hydroxy fatty acid analytics: The GC-MS parameters used to generate chromatograms and mass spectra for compounds identification were as follows:

TABLE 2

| | |
|---|---|
| Sample volume | 1 μL |
| Column | DB-1HT, 10 m × 250 μm × 0.1 μm |
| Initial temperature | 50° C. for 5 minutes |
| Final Temperature | 300° C., held for 5.24 minutes |
| Temperature increase rate | 25° C./minute |
| Total run time | 24 minutes |
| Column flow rate | 1.2 mL/min |
| Inlet temperature | 300° C. |
| Split ratio | 20:1 |
| Analyzing software | ChemStation E.02.01.1177 |

The mass spectrometry parameters are shown in Table 3.

TABLE 3

| | |
|---|---|
| Transfer line temperature | 300° C. |
| MS source temperature | 230° C. |
| MS Quad temperature | CombiPAL (CTC analytics) |

The GC-FID parameters used to quantify each compound are shown in Table 4:

TABLE 4

| | |
|---|---|
| Sample volume | 1 μL |
| Column | UFC Rtx-1, 5M × 0.1 mm × 0.1 μM (Thermo Fisher Ultrafast TRACE GC) |
| Initial oven temperature | 100° C. (0.2 minutes) |
| Final oven temperature | 320° C. (0.5 minutes) |
| Temperature increase rate | 100° C./min |
| Total run time | 2.5 minutes |
| Column flow rate | 0.5 mL/min |
| Inlet temperature | 300° C. |
| Flame ionization detector temperature | 300° C. |

Fatty alcohols analytics: The GC-FID parameters used to quantify each compound are shown in Table 5.

TABLE 5

| | |
|---|---|
| Sample volume | 1 μL |
| Column | UFC Rtx-1, 5M × 0.1 mm × 0.1 μM (Thermo Fisher Ultrafast TRACE GC) |
| Initial oven temperature | 100° C. (0.3 minutes) |
| Final oven temperature | 300° C. (0.05 minutes) |
| Temperature increase rate | 120° C./min |
| Total run time | 2.02 minutes |
| Column flow rate | 0.5 mL/min |
| Inlet temperature | 350° C. |
| Flame ionization detector temperature | 300° C. |

The protocols detailed above represents standard conditions, which may be modified as necessary.

Cellular Fatty Acid Analysis:

Strains were grown over night in Luria-Bertani (LB) medium. The cellular fatty acids (i.e., fatty acids mainly from membrane phosholipids) were extracted and analyzed as follows: 10-20 mL of cultures were harvested and saponified at 70° C. for 1 hr using 1 mL of 15% (W/V) NaOH in 50% MeOH. The solutions were cooled down to room temperature and acidified by concentrated HCl to pH of 1-2. The acidic solution was then extracted with butyl acetate using a vortexer at 2500 rpm for 5 minutes. Extracts were centrifuged in an Eppendorf centrifuge at 15000 rpm for 5 minutes at room temperature. The organic layer (100 uL) was pipetted to a GC vial with insert, derivatized by adding 100 μL of N,O-bis(trimethylsilyl) trifluoroacetamide (BSTFA) and 1% trimethylchlorosilane (TMCS) and mixed using a vortexer for 30 seconds. The sample was then injected on GC-MS to generate chromatograms and mass spectra for compound identification. The GC-MS parameters were the same as in Table 2 and 3 above.

Example 2: Identification of a Novel Δ9-Tetradecanoyl-ACP Desaturase

This example describes the discovery of a novel Δ9-tetradecanoyl-ACP desaturase.

A chloroplastic desaturase from *Pelargonium xhortorum* (DES_Pxho) (SEQ ID NOs: 1 and 2) (GenBank: AAC49421, UniProtKB-Q40879) is a Δ9-tetradecanoyl-ACP desaturase (see above). In order to identify another Δ9-tetradecanoyl-ACP and to compare with DES_Pxho, a comprehensive bioinformatics analysis of the family of plant acyl-ACP desaturases [EC 1.14.19.2] was conducted. Although the substrate specificity and regioselectivity of acyl-ACP desaturases cannot be predicted from their primary sequence, twenty putative "non-canonical" acyl-ACP desaturases with unknown substrate specificity and unknown regioselectivity were identified. These were not predicted to be canonical Δ9-stearoyl-ACP desaturases. Canonical Δ9-stearoyl-ACP desaturases are common and essential "housekeeping" desaturase enzymes in all plants and were not considered in this analysis.

The genes for the twenty unknown plant acyl-ACP desaturases were codon optimized for *E. coli* and cloned under control of an inducible Ptrc promoter into an expression vector (p15a replicon, kanamycin resistance marker). The twenty plasmids were transformed into an *E. coli* MG1655 derivative strain that contained an IPTG-inducible operon with a ferredoxin reductase (petH) (SEQ ID NOs: 3 and 4) (UniProtKB-B2IUI2) and a ferredoxin (petF) (SEQ ID NOs: 5 and 6) (UniProtKB-B2J405) from the cyanobacterium *Nostoc punctiforme* PCC73102. In addition, the strain harbored a second plasmid (SC101 replicon, spectinomycin resistance marker) containing, under control of the inducible Ptrc promoter, either a fatA thioesterase gene from *Arabidopsis thaliana* (SEQ ID NOs: 7 and 8) (UniProtKB-Q42561) (plasmid pAS.033) or a thioesterase gene from *Clostridium thermocellum* (SEQ ID NOs: 9 and 10) (UniProtKB-A3DJY9) (plasmid pAZ026).

Depending on which thioesterase plasmid was used, the strains allow identification of mainly C16 chain-length saturated and unsaturated free fatty acids released by FatA thioesterase (from plasmid pAS.033) or a mixture of C12-C18 chain-length saturated and unsaturated free fatty acids released by the *Clostridium* thioesterase (from plasmid pAZ026). The free fatty acids are secreted to the culture broth.

All strains were analyzed for their ability to produce non-native mUFAs (e.g., z9-tetradecenoic acid and z11-hexadecenoic acid) from glucose as described in Example 1. The peak identification for non-native fatty acids was performed using authentic standards for z9-tetradecenoic acid and z11-hexadecenoic acid, and the double bond position was confirmed by GC/MS of their dimethyl disulfide (DMDS) adducts (See Nichols et al. 1986, *J. Microbiol. Methods* 5: 49-55). FIGS. 3A, 3B, 4A and 4B show the fragmentation of z9-tetradecenoic acid and z11-hexadecenoic acid, respectively, under mass spectrometry and the resulting spectrum.

When compared with an empty vector (i.e., no desaturase) control strain, expression of one of the twenty "non-canonical," unknown plant acyl-ACP desaturases gave rise to production of non-native mUFAs. Table 6 shows the composition of free fatty acids of the control strain and the strain harboring the novel desaturase F6HB23_VITV from *Vitis vinifera* (GenBank XP_002274652) (SEQ ID NOs: 11 and 12) and the Δ9-tetradecanoyl-ACP desaturase DES_Pxho.

With expression of FatA thioesterase, the only non-native unsaturated fatty acid produced in this strain was z8-hexadecenoic acid. The percentage of z11-hexadecenoic acid of the total fatty acids produced with F6HB23_VITV was 66% compared to 44% with DES_Pxho.

With expression of the thioesterase from *Clostridium*, the non-native mUFAs produced with DES_F6HB23_VITV were z9-tetradecenoic acid (22% of total fatty acids) and z11-hexadecenoic acid (16% of total fatty acids). This data indicates that z11-hexadecenoic acid is produced via elongation of Δ9-tetradecanoyl-ACP to Δ11-hexadecenoyl-ACP (by FabB and/or FabF enzymes) and that the novel desaturase acts on tetradecanoyl-ACP and not on hexadecanoyl-ACP.

This example shows that the desaturase F6HB23_VITV from *Vitis vinfera* is a novel Δ9-tetradecanoyl-ACP desaturase and when co-expressed with a thioesterase in a proteobacterium like *E. coli* gives rise to (ω-5 mUFAs such as z9-tetradecenoic acid and z11-hexadecenoic acid.

and 6), and subsequently the gene for a 3-hydroxy-acyl-ACP dehydratase (FabZ) (SEQID NOs 15 and 16) (UniProtKB-A0A0M1I0X8) from *Acinetobacter* baylyi controlled by a constitutive PT5 promoter was also integrated. Next, plasmid pIR.074 (p15a replicon, kanamycin resistance marker) containing the DES_Pxho gene under the control of an IPTG-inducible promoter, was transformed yielding strain AA.827.

The dual hydroxy-acyl-ACP dehydratase/isomerase FabA gene in AA.827 was deleted as follows: Plasmid pXC.006 (temperature sensitive SC101* replicon, ampicillin resistance marker) containing a temperature-sensitive FabA gene (FabA$^{ts}$, see Johnson and Greenberg 1975, J. Bacteriol. 122: 570-574) under the control of a constitutive promoter was transformed. Next, at the permissive temperature of 30° C., the chromosomal FabA gene was deleted, i.e., plasmid pXC.006 was maintained and FabA$^{ts}$ enzyme was functional, and subsequently plasmid pXC.006 harboring FabA$^{ts}$ was cured (i.e., removed) from the strain at an increased non-permissive temperature (42° C.), yielding strain sAS.561, which lacks FabA activity at all temperatures. Adaptive evolution was performed on strain sAS.561 and strain sAS.571 was obtained.

TABLE 6

| Composition of free fatty acids produced in strains harboring the novel desaturase F6HB23_VITV from *Vitis vinifera* | | | | | | | | |
|---|---|---|---|---|---|---|---|---|
| FAS (mg/L) | C8-C12 (%) | z7C14:1 (%) | z9C14:1 (%) | C14:0 (%) | z9C16:1 (%) | z11C16:1 (%) | C16:0 (%) | C18 (%) |
| Plasmid pAS.033 with fatA thioesterase | | | | | | | | |
| Control | 1319 | 0 | 0 | 0 | 11 | 29 | 0 | 54 | 6 |
| Desaturase F6HB23_VITV | 1223 | 0 | 0 | 0 | 12 | 12 | 66 | 10 | 0 |
| Desaturase DES_Pxho | 1455 | 0 | 0 | 0 | 5 | 34 | 44 | 15 | 2 |
| Plasmid pAZ026 with tesZ1 thioesterase | | | | | | | | |
| Control | 872 | 18 | 17 | 0 | 27 | 9 | 0 | 17 | 12 |
| Desaturase F6HB23_VITV | 977 | 24 | 9 | 22 | 5 | 5 | 16 | 7 | 12 |

Example 3: Construction of a Recombinant *E. coli* Strain for the Production of Predominantly Non-Native ω-5 Unsaturated Fatty Acid Derivatives This example describes the construction of a recombinant proteobacterium that contains predominantly non-native ω-5 unsaturated cellular fatty acids (i.e., within its cytoplasmic membrane) and only trace amounts of native ω-7 unsaturated cellular fatty acids. The strain has high flux through the fatty acid biosynthesis pathway and is suitable for high titer production of secreted ω-5 mUFAs or derivatives thereof when an acyl-ACP thioesterase or other fatty acid derivative enzymes (e.g., an ester synthase or an acyl-ACP reductase) are coexpressed.

The strain is a derivative of *E. coli* MG1655 and its genome was engineered as follows: the acyl-CoA dehydrogenase (fadE) gene was deleted and a variant of the transcriptional regulator FadR was overexpressed. Both modifications are optional. Next, an operon controlled by a constitutive PT5 promoter was integrated into the chromosome that contained the Δ9-tetradecanoyl-ACP desaturase gene (without the plastid targeting leader sequence) from *P. xhortorum* (DES_Pxho), and flavodoxin reductase (fpr) (SEQID NOs: 13 and 14) (UniProtKB-P28861) and ferredoxin (petF) from *Nostoc punctiforme* PCC73102 (SEQID NOs: 5

To determine the strain's ability to produce non-native ω-5 unsaturated mUFAs, the composition of the cellular fatty acids were determined as described in Example 1, and it was compared to a similar control strain but with intact FabA gene and without a desaturase gene (sZR.409). As shown in Table 7 the unsaturated fatty acids of strain AA.827, which contained the DES_Pxho gene but had FabA gene intact, consisted of ~40% non-native ω-5unsaturated fatty acids. The unsaturated cellular fatty acid of strain sAS.571, which contained DES_Pxho and deletion of the FabA gene, consisted predominantly (~95%) of non-native ω-5unsaturated fatty acids, and of those 86% were z11-hexadecenoic acid and 14% were z13-octadecenoic acid. Interestingly, the percent unsaturation of the cytoplasma membrane in sAS.571 was higher than for the control strain.

These results show that a Δ9-tetradecanoyl-ACP desaturase can functionally replace the 3-hydroxy-acyl-ACP dehydratase/isomerase FabA gene in a proteobacterium like *E. coli* and gives rise to predominantly ω-5 mUFAs such as z11-hexadecenoic acids and z13-octadecenoic acid when the FabA gene is deleted. As the recombinant strain described in this example has a high flux fatty acid biosynthesis pathway, it can be employed to produce and secrete non-native ω-5 mUFAs and derivatives thereof at high titer.

TABLE 7

| | Composition of cellular fatty acids (CFAs) of recombinant E. coli strains | | | |
| Strain | SFA [1] (% of total) | UFA[2] (% of total) | % ω-5 of UFA | % ω-7 of UFA[2] |
| --- | --- | --- | --- | --- |
| SZR.409 (control) | 36.1 | 63.9 | 1.5 | 98.5 |
| AA.827 | 34.2 | 64.9 | 40.5 | 59.5 |
| SAS.571 | 32.6 | 67.4 | 95.1 | 4.9 |

[1] saturated fatty acids: does not include 3-hydroxy tetradecanoic acid from outer membrane lipopolysaccharides
[2] unsaturated fatty acids: includes cyclopropane C17:0 fatty acid, which is derived from z9-hexadecenoic acid

Example 4: Production of Non-Native ω5-Unsaturated Free Fatty Acids by a Recombinant E. coli Strain This example shows that a recombinant ΔFabA E. coli strain expressing a Δ9-tetradecanoyl-ACP desaturase and a thioesterase predominantly produces non-native ω-5mUFAs and only trace amounts of native ω-7 unsaturated mUFAs.

Strain sAS.571 (prepared as in Example 3) was transformed with plasmid pKM.023 (SC101 replicon, spectinomycin resistance marker) containing an inducible Ptrc promoter and an operon with the fatA thioesterase gene from *Arabidopsis thaliana* and the native FabB β-ketoacyl-ACP synthase gene. The resulting strain was sAS.563. The control strain with intact FabA gene and without a desaturase gene was the same as the control strain in Example 3 transformed with plasmid pKM.023 (strain AA.804).

The strains were subjected to small scale fermentation and product analysis as described in Example 1. As shown in Table 8, strain sAS.563 produced over 2000 mg/L of free fatty acids at 32° C. and 37° C. with a high degree of unsaturation. All strains were evaluated for their ability to produce non-native mUFAs. The peak identification for z9-tetradecenoic acid and z11-hexadecenoic acid was performed by comparing their retention time and ion fragmentation pattern in GC/MS to that of authentic standards. The double bond position was confirmed by GC/MS of their dimethyl disulfide (DMDS) adducts as shown in FIGS. 3A-B and 4A-B. The peak identification for z13-octadecenoic acid was based on its expected retention time and ion fragmentation pattern relative to native z11-octadecenoic acid.

As shown in Table 8, ~99% of the unsaturated fatty acid produced by sAS.563 had the double bond in the non-native ω-5 position with the majority being z11-hexadecenoic acid and smaller amounts of z9-tetradecenoic acid and z13-octadecenoic acid produced.

Interestingly, the E. coli control strain produced trace amounts of z11-hexadecenoic acid, which is not observed in the E. coli MG1655 wild-type strain. This may be attributed to the high fatty acid biosynthesis flux in the control strain allowing FabA to isomerize not only trans-2-decenoyl-ACP (native substrate) to cis-3-decenoyl-ACP (precursor to native ω-7 mUFA) but also to a minor extend trans-2-octenoyl-ACP (non-native substrate) to cis-3-octenoyl-ACP (precursor to non-native ω-5 mUFA). Similarly, trace amounts of z11-hexadecenoic acid were also found in the cellular fraction of the control strain without plasmid pKM.023 (see Example 3 and Table 7).

This example demonstrates that a recombinant ΔFabA E. coli strain expressing a Δ9-tetradecanoyl-ACP desaturase posseses a high flux fatty acid biosynthesis pathway and when co-expressed with a thioesterase produces non-native ω-5 unsaturated fatty acids at high titer and with only trace amounts of native ω-7 unsaturated fatty acids. Besides lesser amounts of z9-tetradecenoic acid and z13-octadecenoic acid, z11-hexadecenoic acid was the major non-native fatty acid produced.

TABLE 8

| | Composition and titer of free fatty acids (FFA) of recombinant E. coli strains | | | | | | | | |
| strain | Total FFA (mg/L) | % UFA of FFA | % ω5 of UFA | z7-C14:1 (mg/L) | z9-C14:1 (mg/L) | z9-C16:1 (mg/L) | z11-C16:1 (mg/L) | z11-C18:1 (mg/L) | z13-C18:1 (mg/L) |
| --- | --- | --- | --- | --- | --- | --- | --- | --- | --- |
| AA.804 (control) | 3558 | 70 | 1.3 | 0 | 0 | 2292 | 32 | 15 | 0 |
| sAS.563 (32C) | 2094 | 77 | 99.2 | 0 | 133 | 12 | 1448 | 0 | 8 |
| sAS.563 (37C) | 2055 | 75 | 99.4 | 0 | 171 | 9 | 1363 | 0 | 6 |

Example 5: Production of ω-5 Unsaturated Fatty Alcohols by Recombinant E. coli Strains This example shows that a recombinant ΔFabA E. coli strain expressing a Δ9-tetradecanoyl-ACP desaturase, a thioesterase and a carboxylic acid reductase predominantly produces ω-5 unsaturated fatty alcohols (e.g., z11-hexadecenol and z9-tetradecenol) and only trace amounts of ω-7 unsaturated fatty alcohols (e.g., z9-hexadecenol).

In strain sAS.571 (prepared as in Example 3), the chromosomal entD gene was deregulated by replacing the native iron-regulated promoter of entD with a constitutive PT5 promoter. EntD is a promiscous phosphopantetheinyl transferase utilized in this strain to posttranslationally modify a carboxlic acid reductase. The resulting strain sAS.619 was transformed with plasmids pSVEN.250 and pSVEN.251, respectively, yielding strains sven.1236 and sven.1237. Both plasmids (SC101 replicon, spectinomycin resistance marker) contain two operons: the first operon contains under control of an inducible Ptrc promoter the fatA thioesterase gene from *Arabidopsis thaliana* and the FabB β-ketoacyl-ACP synthase gene; the second operon contains, under control of an inducible PT5 promoter, a carB carboxylic acid reductase gene from *Mycobacterium smegmatis* (SEQ ID NOs: 17 and 18) (UniProtKB-A0A653FCI4) and the alrA alcohol dehydrogenase gene from *Acinetobacter* baylyi (SEQ ID NOs: 19 and 20) (UniProtKB-Q6F6R9). The expression of the first operon was higher in plasmid pSVEN.250 than in pSVEN.251. A similar control strain with the intact FabA gene and without a desaturase (strain sOW.006) was used for this experiment.

The strains were subjected to small scale fermentation and product analysis as described in Example 1. Authentic standards for the non-native ω-5 unsaturated fatty alcohols were not available. Peak identification was based on their expected retention times and ion fragmentation patterns relative to native ω-7 unsaturated fatty alcohols. As shown in Table 9, both strains sven.1236 and sven.1237 produced a large amount of z11-hexadecenol and (~800 mg/L) as well as z9-tetradecenol (41-123 mg/L), and both strains produced only trace amounts of the corresponding unsaturated fatty alcohols with the native ω-7 double bond (z9-hexadecenol). In contrast, the control strain produced a large amount of z9-hexadecenol (~1400 mg/l) and only little z11-hexadecenol.

This example demonstrates that a recombinant ΔFabA E. coli strain expressing a Δ9-tetradecanoyl-ACP desaturase possesses a high flux fatty acid biosynthesis pathway and when co-expressed with a thioesterase and a carboxylic acid reductase produces ω5-unsaturated fatty alcohols at high titer and with only trace amounts of ω7-unsaturated fatty alcohols. Besides lesser amounts of z9-tetradecenol, z11-hexadecenol was the major fatty alcohol produced.

acids consisted of 12 mg/L (z9)-14-hydroxy tetradecenoic acid, 41 mg/L 14-hydroxy tetradecanoic acid, 211 mg/L (z11)-16-hydroxy hexadecenoic acid and 126 mg/L 16-hydroxy hexadecanoic acid. The strain produced only trace amounts of (z9)-16-hydroxy hexadecenoic acid.

This example demonstrates that a recombinant ΔFabA E. coli strain expressing a Δ9-tetradecanoyl-ACP desaturase possesses a high flux fatty acid biosynthesis pathway and when co-expressed with a thioesterase and a ω-hydroxylase produces non-native ω-5 unsaturated ω-hydroxy fatty acids with only trace amounts of native ω-7 unsaturated ω-hydroxy fatty acids. Besides lesser amounts of (z9)-14-hydroxy tetradecenoic acid, (z11)-16-hydroxy hexadecenoic acid was the major ω-hydroxy fatty acid produced.

When (z11)-16-hydroxy hexadecenoic acid is subjected to chemical lactonization, (12z)-1-oxacycloheptadec-12-en-2-one is produced, which is structurally similar to musk fragrances such as ambrettolide ((8z)-1-oxacycloheptadec-8-en-2-one), cis-isoambrettolide ((10z)-1-oxacycloheptadec-10-en-2-one) or isoambrettolide ((10e)-1-oxacycloheptadec-10-en-2-one) (see e.g., International Patent Application Publication WO 2015/157719 A9).

TABLE 9

Composition and titer of fatty alcohols (FALC) of recombinant E. coli strains

| strain | Total FFA (mg/L) | Total FALC (mg/L) | % FALC | % [UFA + UFALC] | % ω5 of UFALC | z7-C14:1 FALC (mg/L) | z9-C14:1 FALC (mg/L) | z9-C16:1 FALC (mg/L) | z11-C16:1 FALC (mg/L) |
|---|---|---|---|---|---|---|---|---|---|
| sOW.006 (control) | 992 | 1598 | 61 | 90 | 3.2 | 7 | 0 | 1428 | 49 |
| sven.1236 (32C) | 155 | 1123 | 88 | 79 | 99.6 | 0 | 123 | 3 | 795 |
| sven.1237 (37C) | 91 | 982 | 92 | 83 | 99.5 | 0 | 41 | 4 | 811 |

Example 6: Production of ω-5 Unsaturated w-Hydroxy Fatty Acids by a Recombinant E. coli Strain This example shows that a recombinant ΔFabA E. coli strain expressing a Δ9-tetradecanoyl-ACP desaturase, a thioesterase and a ω-hydroxylase predominantly produces ω-5 unsaturated ω-hydroxy fatty acids (e.g., (z11)-16-hydroxy hexadecenoic acid) and only trace amounts of ω-7 unsaturated ω-hydroxy fatty acids (e.g., (z9)-16-hydroxy hexadecenoic acid).

Strain sAS.571 (see Example 3) was transformed with plasmid pKM.010, which is a derivative of plasmid pKM.023 (SC101 replicon, spectinomycin resistance marker) (see Example 4) that, in addition to the fatA thioesterase and FabB β-ketoacyl-ACP synthase operon, contains under control of an inducible PT5 promoter a hybrid-fusion Cyp153-RhF ω-hydroxylase (SEQ ID NOs: 22 and 23). The resulting strain was sAS.583.

The strain was subjected to small scale fermentation and product analysis as described in Example 1. Authentic standards of ω-5 unsaturated ω-hydroxy fatty acids were not available. Peak identification was performed based on expected retention times and GC/MS fragmentation patterns relative to the native ω-7 unsaturated ω-hydroxy fatty acids. In addition, the double bond position of (z11)-16-hydroxy hexadecenoic was confirmed by GC/MS of its dimethyl disulfide (DMDS) adducts as shown in FIGS. 5A-5B.

Strain sAS.583 produced 390 mg/L of ω-hydroxy fatty acids and 40 mg/L of free fatty acids. The ω-hydroxy fatty

Example 7: Production of ω-5 Unsaturated Fatty Alcohol Acetate Esters by a Recombinant E. coli Strain Recombinant ΔFabA E. coli strains expressing a Δ9-tetradecanoyl-ACP desaturase, a thioesterase, a carboxylic acid reductase and an acetyl-CoA transferase are expected to predominantly produce non-native ω-5 unsaturated fatty alcohol acetates (z11-hexadecenyl acetate, z9-tetradecenyl acetate, and z13-octadecenyl acetate) and only trace amounts of native ω-7 unsaturated fatty alcohol acetates (e.g., z9-hexadecenyl acetate).

A gene coding for an acetyl-CoA transferase [EC 2.3.1.84], e.g., Atf1 from Saccharomyces cerevisiae (SEQ ID NOs: 23 and 24) (UniProtKB-Q6XBT3), under the control of an inducible or constitutive promoter, is integrated into the chromosome of strain sAS.619 (as prepared in Example 5). The resulting strain is transformed with plasmids pSVEN.250 and pSVEN.251 (see Example 5), respectively, or with similar plasmids.

The strains are subjected to small scale fermentation and product analysis is carried out as described in Example 1. The recombinant proteobacteria are expected to produce non-native ω-5-unsaturated fatty alcohol acetates (z11-hexadecenyl acetate, z9-tetradecenyl acetate and/or z13-octadecenyl acetate) and only trace amounts of native ω7-unsaturated fatty alcohol acetates (e.g., z9-hexadecenyl acetate).

Example 8: Production of ω-5 Unsaturated Fatty
Aldehydes by a Recombinant *E. coli* Strain with
Deleted Alcohol Dehydrogenase Genes Recombinant ΔFabA *E. coli* strains with multiple dele-
tions in alcohol dehydrogenase and/or aldehyde reductase
genes, and expressing a Δ9-tetradecanoyl-ACP desaturase, a
thioesterase and a carboxylic acid reductase are expected to
predominantly produce non-native ω-5 unsaturated fatty
aldehydes (e.g., z11-hexadecenal, z9-tetradecenal and z13-
octadecenal) and only trace amounts of native ω-7 unsatu-
rated fatty aldehydes (e.g., z9-hexadecenal).

Plasmids pSVEN.250 and pSVEN.251 (as prepared in
Example 5) or similar plasmids are modified by deleting the
AlrA gene from the second operon. Strain sAS.619 (see
example 5) is modified by deleting or attenuating one or
more of the yjgB, yahK, ybbO, YqhD, AdhP, EutG, YiaY,
BetA, FucO, DkgA, YghA, GldA or AdhE genes. The
resulting strains are transformed with the modified plasmids
and are subjected to small scale fermentation and product
analysis as described in Example 1. The recombinant pro-
teobacteria are expected to produce predominantly non-
native ω-5 unsaturated fatty aldehydes (e.g., z11-hexadece-
nal, z9-tetradecenal and/or z13-octadecenal) and only trace
amounts of native ω-7 unsaturated fatty aldehydes (e.g.,
z9-hexadecenal).

Example 9: Production of ω-5 Unsaturated
α/ω-Dicarboxylic Acids by a Recombinant *E. coli*
Strain Recombinant ΔFabA *E. coli* strain expressing a Δ9-tetra-
decanoyl-ACP desaturase, a thioesterase, a ω-hydroxylase
and one or two heterologous dehydrogenases (an alcohol
dehydrogenase and an aldehyde dehydrogenase) are
expected to produce predominantly non-native ω-5 unsatu-
rated α/ω-dicarboxylic acids (e.g., (z5)1,16-hexadecene-
dioic acid, (z5)1,14-tetradecenedioic acid and/or (z5)1,18-
octadecenedioic acid acid) and only trace amounts of native
ω-7 unsaturated α/ω-dicarboxylic acids (e.g., (z7)1,16-
hexadecenedioic acid).

Two genes, coding for an alcohol dehydrogenase (e.g.,
UniProtKB-Q00593 from *Pseudomonas oleovorans*; SEQ
ID NO:29) and an aldehyde dehydrogenase (e.g., UniPro-
tKB-Q6FAS2 from *Acinetobacter* baylyi, SEQ ID NO:30),
under the control of inducible or constitutive promoters are
integrated into the chromosome of strain sAS.619 (as pre-
pared in Example 5). The resulting strain is transformed with
plasmid pKM.010 (see Example 5) or a similar plasmid and
is subjected to small scale fermentation and product analysis
as described in Example 1. The recombinant proteobacteria
are expected to produce predominantly non-native ω-5
unsaturated α/ω-dicarboxylic acids (e.g., (z11)1,16-hexade-
cenedioic acid, (z5)1,14-tetradecenedioic acid and/or (z5)1,
18-octadecenedioic acid acid) and only trace amounts of
native ω-7 unsaturated α/ω-dicarboxylic acids (e.g., (z7)1,
16-hexadecenedioic acid).

ω-5 unsaturated α/ω-dicarboxylic acids can be chemi-
cally converted to macrocyclic ketones similar to musk
ketone fragrances (see e.g., International Patent Application
Publication WO 2015/157719 A9). For example, using
decarboxylative chemistry (z5)1,16-hexadecenedioic acid
can be converted to the 15-membered macrocyclic ketones
(5z)-cyclopentadec-5-en-1-one or (4z)-cyclopentadec-4-en-
1-one. The latter is also known as exaltenone. Using non-
decarboxylative chemistry (z5)1,16-hexadecenedioic acid
can be converted to the 16-membered macrocyclic ketones (6Z)-cyclohexadec-6-en-1-one or (5Z)-cyclohexadec-5-en-
1-one. The latter is also known as ambrettone or velvione.

Example 10: Production of ω-5 Unsaturated Fatty
Alcohols by Recombinant *E. coli* Strains
Expressing an Acyl-ACP Reductase Recombinant ΔFabA *E. coli* strain expressing a Δ9-tetra-
decanoyl-ACP desaturase, an acyl-ACP reductase and an
alcohol dehydrogenase produces predominantly non-native
ω-5 unsaturated fatty aldehydes and fatty alcohols (e.g.,
z11-hexadecenal and z11-hexadecenol) and only trace
amounts of ω-7 unsaturated fatty aldehydes and fatty alco-
hols (e.g., z9-hexadecenal and z9-hexadecenol).

Strain sAS.571 (as prepared in Example 3) is transformed
with a plasmid similar to pKM.023 (as prepared in Example
4), in which the FatA thioesterase gene is replaced by the
AAR acyl-ACP reductase gene from Synechococcus *elon-
gatus* (SEQ ID NOs: 34 and 35) (UniProtKB-Q54765) and
optionally the alrA alcohol dehydrogenase gene from *Aci-
netobacter* baylyi (SEQ ID NOs: 19 and 20) (UniProtKB-
Q6F6R9).

The resulting strain is subjected to small scale fermenta-
tion and product analysis as described in Example 1. The
recombinant proteobacterium produces predominantly non-
native ω-5 unsaturated fatty aldehydes and fatty alcohols
such as z9-tetradecenal, z11-hexadecenal, z13-tetradecenal,
z9-tetradecenol, z11-hexadecenol and z13-tetradecenol and
only trace amounts of ω-7 unsaturated fatty aldehydes and
fatty alcohols (e.g., z9-hexadecenal and z9-hexadecenol).

Example 11: Production of ω-5 Unsaturated Fatty
Alcohol Acetate Esters by Recombinant *E. coli*
Strains Expressing an Acyl-ACP Reductase Recombinant ΔFabA *E. coli* strain expressing a Δ9-tetra-
decanoyl-ACP desaturase, an acyl-ACP reductase, an alco-
hol dehydrogenase and an acetyl-CoA transferase produces
predominantly non-native ω-5 unsaturated fatty alcohol
acetates (e.g., z11-hexadecenyl acetate) and only trace
amounts of ω-7 unsaturated fatty alcohol acetates (e.g.,
z9-hexadecenyl acetate).

A gene coding for an acetyl-CoA transferase [EC
2.3.1.84], e.g., Atf1 from *Saccharomyces cerevisiae* (SEQ
ID NOs: 23 and 24) (UniProtKB-Q6XBT3), under the
control of an inducible or constitutive promoter, is integrated
into the chromosome of strain sAS.571 (as prepared in
Example 3). The resulting strain is transformed with the
AAR acyl-ACP reductase containing plasmid prepared in
Example 10.

The resulting strain is subjected to small scale fermenta-
tion and product analysis as described in Example 1. The
recombinant proteobacterium produces non-native ω-5-un-
saturated fatty alcohol acetates such as z11-hexadecenyl
acetate, z9-tetradecenyl acetate and/or z13-octadecenyl
acetate and only trace amounts of native ω7-unsaturated
fatty alcohol acetates (e.g., z9-hexadecenyl acetate).

Example 12: Production of Non-Native
ω5-Unsaturated z9-Tetradecenoic Acid by a
Recombinant *E. coli* Strain This example shows that a recombinant ΔFabA *E. coli*
strain expressing a Δ9-tetradecanoyl-ACP desaturase and a
thioesterase from *Clostridium thermocellum* (UniProtKB-
A3DJY9) predominantly produces non-native ω-5 unsaturated z9-tetradecenoic acid and only trace amounts of native ω-7 unsaturated z7-tetradecenoic acid.

The chromosomal copy of the fabB gene of strain sAS.571 (prepared as in Example 3) was replaced with a variant of fabB yielding strain ECKh-16885. The strain is transformed with plasmid pG_21306 (SC101 replicon, spectinomycin resistance marker) containing a thioesterase gene from *Clostridium thermocellum* under control of an inducible Ptrc promoter. The resulting strain was L29426.

Strain L29426 was subjected to small scale fermentation and product analysis as described in Example 1. As shown in Table 10, strain L29426 produced 285 mg/L of free fatty acids at 32° C. with a high content of C14 fatty acids (68%).

As shown in Table 10, 100% of the unsaturated fatty acid produced by L29426 had the double bond in the non-native ω-5 position with the majority being z9-tetradecenoic acid and smaller amounts of z11-hexadecenoic acid. The peak identification for z9-tetradecenoic acid and z11-hexadecenoic acid was performed by comparing their retention time and ion fragmentation pattern in GC/MS to that of authentic standards.

This example demonstrates that a recombinant ΔFabA *E. coli* strain expressing a Δ9-tetradecanoyl-ACP desaturase when co-expressed with an acyl-ACP thioesterase with high specificity for acyl-ACPs with C14 chain length such as from *Clostridium thermocellum* TE A3DJY9 produces predominantly non-native ω-5 unsaturated C14 fatty acids with only trace amounts of native ω-7 unsaturated C14 fatty acids.

Example 14: Production of ω-5 Unsaturated Fatty Alcohols by Recombinant *E. coli* Strains with Attenuated FabA This example shows that a recombinant *E. coli* strain with attenuated FabA expressing a Δ9-tetradecanoyl-ACP desaturase, a thioesterase, and a carboxylic acid reductase produces mixtures of ω-5 unsaturated fatty alcohols (e.g., z9-tetradecenol, z11-hexadecenol and z13-octadecenol) and ω-7 unsaturated fatty alcohols (e.g., z7-tetradecenol, z9-hexadecenol and z11-octadecenol).

The strain is a derivative of *E. coli* MG1655 and its genome is engineered as follows: the acyl-CoA dehydrogenase (fadE) gene is deleted and a variant of the transcriptional regulator FadR is overexpressed. Both modifications are optional. An operon controlled by a constitutive PT5 promoter is integrated into the chromosome that contained the Δ9-tetradecanoyl-ACP desaturase gene (without the plastid targeting leader sequence) from *P. xhortorum* (DES_Pxho), and flavodoxin reductase (fpr) (SEQ ID NOs: 13 and 14) (UniProtKB-P28861) and ferredoxin (petF) from *Nostoc punctiforme* PCC73102 (SEQ ID NOs: 5 and 6). Additionally, the chromosomal entD gene is deregulated by replacing the native iron-regulated promoter of entD with a constitutive PT5 promoter. Optionally, the gene for a 3-hydroxy-acyl-ACP dehydratase (FabZ) (SEQ ID NO: 15 and 16) (UniProtKB-A0A0M1I0X8) from *Acinetobacter* baylyi controlled by a constitutive PT5 promoter is also integrated.

TABLE 10

Composition and titer of free fatty acids (FFA) of recombinant *E. coli* strains

| strain | Total FFA (mg/L) | % C14 FFA | % UFA of FFA | % ω5 of UFA | z7-C14:1 (mg/L) | z9-C14:1 (mg/L) | z9-C16:1 (mg/L) | z11-C16:1 (mg/L) | z11-C18:1 (mg/L) |
|--------|------------------|-----------|--------------|-------------|------------------|------------------|------------------|-------------------|-------------------|
| L29426 | 285 | 68 | 45 | 100 | 0 | 107 | 0 | 23 | 0 |

Example 13: Production of ω-5 Unsaturated z9-Tertadecenol by Recombinant *E. coli* Strains This example shows that a recombinant ΔFabA *E. coli* strain expressing a Δ9-tetradecanoyl-ACP desaturase, a thioesterase from *Clostridium thermocellum* (UniProtKB-A3DJY9) and a carboxylic acid reductase predominantly produces ω-5 unsaturated z9-tetradecenol) and only trace amounts of ω-7 unsaturated z7-tetradecenol).

The chromosomal copy of the fabB gene of strain sAS.619 (prepared as in Example 5) is replaced with a variant of fabB. The resulting strain is transformed with a plasmid (SC101 replicon, spectinomycin resistance marker) containing a thioesterase gene from *Clostridium thermocellum* under control of an inducible Ptrc promoter and containing a second operon, under control of an inducible PT5 promoter, with the carB carboxylic acid reductase gene from *Mycobacterium smegmatis* (SEQ ID NOs: 17 and 18) (UniProtKB-A0A653FCI4) and the alrA alcohol dehydrogenase gene from *Acinetobacter* baylyi (SEQ ID NOs: 19 and 20) (UniProtKB-Q6F6R9).

The strain is subjected to small scale fermentation and product analysis as described in Example 1. The strain is expected to produce predominantly C14 fatty acid derivatives. The strain is expected to produce predominantly ω-5 unsaturated z9-tetradecenol and only trace amounts of ω-7 unsaturated z7-tetradecenol.

The dual hydroxy-acyl-ACP dehydratase/isomerase fabA gene is attenuated as follows: the native promoter or RBS controlling FabA's transcription or translation initiation are modified or replaced with a weaker synthetic promoter or RBS, or FabA's start codon is altered from ATG to GTG or TTG or the native fabA gene is replaced with a fabA gene encoding an altered FabA protein variant which is less active or less stable, for example FabA$^{ts}$ (see Johnson and Greenberg 1975, J. Bacteriol. 122: 570-574), or a combination thereof.

The resulting recombinant strain is transformed with plasmid pSVEN.250 or pSVEN.251 (see Example 5) or a similar expression plasmid containing the fatA thioesterase gene from *Arabidopsis thaliana*, the FabB β-ketoacyl-ACP synthase gene, a carB carboxylic acid reductase gene from *Mycobacterium smegmatis* (SEQ ID NOs: 17 and 18) (UniProtKB-A0A653FCI4) and the alrA alcohol dehydrogenase gene from *Acinetobacter* baylyi (SEQ ID NOs: 19 and 20) (UniProtKB-Q6F6R9)

The strain is subjected to small scale fermentation and product analysis as described in Example 1. The ω-5 and ω-7 unsaturated fatty alcohols, e.g., z9-tetradecenol, z11-hexadecenol, z13-octadecenol, z7-tetradecenol, z9-hexadecenol and z11-octadecenol are measured. Depending on the level of FabA attenuation, the strain may produce more ω-5 unsaturated than ω-7 unsaturated fatty alcohols, e.g., 90% of ω-5 unsaturated and 10% ω-7 unsaturated fatty alcohols (e.g. 80% of z11-hexadecenol and 10% of z13-octadecenol and 10% of z9-hexadecenol).

All references, including publications, patent applications, and patents, cited herein are hereby incorporated by reference to the same extent as if each reference were individually and specifically indicated to be incorporated by reference and were set forth in its entirety herein.

Particular embodiments of this invention are described herein, including the best mode known to the inventors for carrying out the invention. Variations of those particular embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Sequence Table

| SEQ ID NO: | Description | Sequence |
|---|---|---|
| 1 | myristyl-ACP desaturase [*Pelargonium* x *hortorum*], DNA sequence without plastid leader sequence | ATGGCTTCTACCTCTATCTCTAAAGTTAACCACATCCGTAA AGTTGGTGTTACCGGTGTTATGGCTCCGCAGAAAATCGAA ATCTTCAAATCTATGGAAGAATGGGGTAAACACAACATCC TGCCGCTGGCTAAACCGGTTGAAAAATCTTGGCAGCCGAC CGACTTCCTGCCGGACCCGTCTTCTGAAGGTTTCATGGAAG AATACAACGCTTTCAAAGAACGTACCCGTGAACTGCCGGA CGAATACTTCGTTGTTCTGGCTGGTGACATGATCACCGAAG AAGCTCTGCCGACCTACCAGACCCTGGTTAACCGTCCGGAC GAAGTTGCTGACGAAACCGGTCACTCTGAATCTCCGTGGG CTGTTTGGTCTCGTGCTTGGACCGCTGAAGAAAACCGTCAC GGTGACCTGCTGAACAAATACCTGTACCTGTCTGGTAAACT GGACATGCGTCAGGTTGAAAAAACCATCCAGTACCTGATC GCTCTGGGTCAGGACATCGGTACCGAAAAAAAACCCGTACC ACCTGTTCATCTACACCTCTTTCCAGGAACGTGCTACCTTC ATCTCTCACGCTAACACCGCTAAACTGGCTCAGCAGCACG GTGACAAACAGCTGGCTCAGATCTGCGGTACCATCGCTGCT GACGAAAAACGTCACGAAACCGCTTACACCCGTATCGTTG ACAAACTGTTCGAACTGGACCCGGACGAAACCATGTCTTG CCTGGCTCACATGATGAAACGTAAAATCACCATGCCGGCT CACCTGATGCGTGACGGTCGTGACCCGCACCTGTTCCAGCA CTTCTCTGTgGTTGCTTCTCGTACCGGTGTTTACACCGTTAT GGACTACATCAACATCCTGGAACACTTCGTTGAAAAATGG AACATCGAAAAAATCACCGCTGGTCTGTCTGACAAAGGTC GTGAAGCTCAGGACTACGTTTGCAAACTGGGTGAACGTCT GCGTAAAGTTGAAGAACGTGCTCACCAGCGTGTTGTTCAG GCTGACCCGATCCCGTTCTCTTGGATCTTCGACCGTAAAGT TTAA |
| 2 | myristyl-ACP desaturase [*Pelargonium* x *hortorum*], mature protein | MASTSISKVNHIRKVGVTGVMAPQKIEIFKSMEEWGKHNILPL AKPVEKSWQPTDFLPDPSSEGFMEEYNAFKERTRELPDEYFV VLAGDMITEEALPTYQTLVNRPDEVADETGHSESPWAVWSR AWTAEENRHGDLLNKYLYLSGKLDMRQVEKTIQYLIALGQDI GTEKNPYHLFIYTSFQERATFISHANTAKLAQQHGDKQLAQIC GTIAADEKRHETAYTRIVDKLFELDPDETMSCLAHMMKRKIT MPAHLMRDGRDPHLFQHFSVVASRTGVYTVMDYINILEHFVE KWNIEKITAGLSDKGREAQDYVCKLGERLRKVEERAHQRVV QADPIPFSWIFDRKV |
| 3 | Ferredoxin reductase PetH, Nostoc punctiforme PCC73102, DNA Sequence | ATGACTCAAGCGAAAGCCAAAAAAGACCACGGTGACGTTC CTGTTAACACTTACCGTCCCAATGCTCCATTTATTGGCAAG GTAATATCTAATGAACCATTAGTCAAAGAAGGTGGTATTG GTATTGTTCAACACCTTAAATTTGACCTATCTGGTGGGGAT TTGAAGTATATAGAAGGTCAAAGTATTGGCATTATTCCGCC AGGTTTAGACAAGAACGGCAAGCCTGAAAAACTCAGACTA TATTCCATCGCCTCAACTCGTCATGGTGATGATGTAGATGA TAAGACAGTATCACTGTGCGTCCGCCAGTTGGAGTACAAG CACCCAGAAACTGGCGAAACAGTCTACGGTGTTTGCTCTAC GCACCTGTGTTTCCTCAAGCCAGGGGAAGAGGTAAAAATT ACAGGGCCTGTGGGTAAGGAAATGTTGTTACCCAATGACC CTGATGCTAATGTTATCATGATGGCTACTGGAACAGGTATT GCGCCGATGCGGGCTTACTTGTGGCGTCAGTTTAAAGATGC GGAAAGAGCGGCTAACCCAGAATACCAATTTAAAGGATTC TCTTGGCTAATATTTGGCGTACCTACAACTCCAAACCTTTT ATATAAGGAAGAACTGGAAGAGATTCAACAAAAATATCCT GAGAACTTCCGCCTAACTGCTGCCATCAGCCGCGAACAGA AAAATCCCCAAGGCGGTAGAATGTATATTCAAGACCGCGT AGCAGAACATGCTGATGAATTGTGGCAGTTGATTAAAAAT GAAAAAACCCACACTTACATTTGCGGTTTGCGCGGTATGG AAGAAGGTATTGATGCAGCCTTAACTGCTGCTGCTGCTAAG GAAGGCGTAACCTGGAGTGATTACCAGAAGCAACTCAAGA AAGCCGGTCGCTGGCACGTAGAAACTTACTAA |

-continued

| Sequence Table | | |
|---|---|---|
| SEQ ID NO: | Description | Sequence |
| 4 | Ferredoxin reductase PetH, *Nostoc punctiforme* PCC73102, mature protein | MTQAKAKKDHGDVPVNTYRPNAPFIGKVISNEPLVKEGGIGI VQHLKFDLSGGDLKYIEGQSIGIIPPGLDKNGKPEKLRLYSIAS TRHGDDVDDKTVSLCVRQLEYKHPETGETVYGVCSTHLCFL KPGEEVKITGPVGKEMLLPNDPDANVIMMATGTGIAPMRAYL WRQFKDAERAANPEYQFKGFSWLIFGVPTTPNLLYKEELEEIQ QKYPENFRLTAAISREQKNPQGGRMYIQDRVAEHADELWQLI KNEKTHTYICGLRGMEEGIDAALTAAAAKEGVTWSDYQKQL KKAGRWHVETY |
| 5 | Ferredoxin PetF, *Nostoc punctiforme* PCC73102, DNA sequence | ATGCCAACTTATAAAGTGACACTAATTAACGAGGCTGAAG GGCTGAACACAACCCTTGATGTTGAGGACGATACCTATATT CTAGACGCAGCTGAAGAAGCTGGTATTGACCTGCCCTACTC TTGCCGCGCTGGTGCTTGCTCTACTTGTGCAGGTAAACTCG TATCAGGTACCGTCGATCAAGGCGATCAATCATTCTTAGAT GACGATCAAATAGAAGCTGGATATGTACTGACCTGTGTTG CTTACCCAACTTCTAATGTCACGATCGAAACTCACAAAGAA GAAGAACTCTATTAA |
| 6 | Ferredoxin PetF protein, *Nostoc punctiforme* PCC73102 | MPTYKVTLINEAEGLNTTLDVEDDTYILDAAEEAGIDLPYSCR AGACSTCAGKLVSGTVDQGDQSFLDDDQIEAGYVLTCVAYP TSNVTIETHKEEELY |
| 7 | FatA thioesterase from *Arabidopsos thaliana*, DNA sequence without plastid leader sequence | ATGGCTGTTGTATCTGCTGATCAAGGTAGTGTGGTTCAAGG TTTGGCTACTCTCGCGGATCAGCTCCGATTAGGTAGTTTGA CTGAAGATGGTTTATCTTATAAAGAGAAGTTTGTTGTTAGA TCTTACGAAGTGGGTAGTAACAAAACCGCTACTGTTGAAA CCATTGCTAATCTTTTACAGGAGGTGGGATGTAATCATGCA CAAAGTGTTGGTTTTTCGACTGATGGGTTTGCAACAACAAC TACTATGAGGAAGTTGCATCTCATTTGGGTTACTGCGAGAA TGCATATCGAGATCTATAAGTACCCTGCTTGGGGTGATGTG GTTGAGATAGAGACTTGGTGTCAGAGTGAAGGAAGGATTG GGACAAGGCGTGATTGGATTCTTAAGGATTCTGTCACTGGT GAAGTCACTGGCCGTGCTACAAGCAAGTGGGTGATGATGA ACCAAGACACGAGACGGCTTCAGAAAGTTTCTGATGATGT TCGGGACGAGTACTTGGTCTTCTGTCCTCAAGAACCGAGGT TAGCATTTCCGGAAGAGAATAACCGTAGCTTGAAGAAAAT CCCGAAACTCGAAGATCCGGCTCAGTATTCAATGATTGGG CTTAAGCCTAGACGAGCTGATCTCGACATGAACCAGCATG TCAATAATGTCACCTATATTGGATGGGTTCTGGAGAGCATA CCACAAGAAATTGTAGACACGCACGAGCTTCAGGTCATAA CTCTGGATTATAGAAGAGAATGTCAACAAGACGATGTGGT GGATTCACTCACCACCACCACCTCTGAAATTGGTGGAACCA ATGGCTCTGCCACGTCTGGCACACAGGGCCACAACGATAG CCAGTTCTTGCACCTCCTGAGGTTGTCTGGAGATGGTCAGG AGATCAACCGCGGGACAACTCTGTGGAGAAAGAAGCCTTC AAGTTAA |
| 8 | FatA thioesterase from *Arabidopsos thaliana*, UniProtKB-Q42561 (Genbank NP_189147), mature protein | MAVVSADQGSVVQGLATLADQLRLGSLTEDGLSYKEKFVVR SYEVGSNKTATVETIANLLQEVGCNHAQSVGFSTDGFATTTT MRKLHLIWVTARMHIEIYKYPAWGDVVEIETWCQSEGRIGTR RDWILKDSVTGEVTGRATSKWVMMNQDTRRLQKVSDDVRD EYLVFCPQEPRLAFPEENNRSLKKIPKLEDPAQYSMIGLKPRR ADLDMNQHVNNVTYIGWVLESIPQEIVDTHELQVITLDYRRE CQQDDVVDSLTTTTSEIGGTNGSATSGTQGHNDSQFLHLLRLS GDGQEINRGTTLWRKKPSS |
| 9 | ABN54268.1 *Clostridium thermocellum* ATCC 27405 acyl-ACP thioesterase gene | ATGCAGAAGAAAAGATTTTCAAAGAAGTATGAAGTACATT ACTACGAAATCAACTCAATGCAGGAAGCAACTCTTCTCTCC CTGCTAAACTATATGGAGGACTGCGCAATATCCCACTCAAC CTCTGCCGGATACGGTGTCAACGAGTTATTGGCTGCTGACG CAGGATGGGTATTATACCGCTGGTTAATTAAAATAGACAG ACTTCCCAAGCTCGGAGAAACAATTACTGTTCAGACATGG GCCTCTTCCTTCGAACGCTTCTACGGCAACAGGGAATTTAT CGTATTGGACGGCAGGGATAACCCCATTGTCAAAGCCTCA TCCGTATGGATATATTTCAATATTAAAAAAAGAAAACCTAT GAGAATCCCCCTCGAAATGGGAGATGCTTATGGCATAGAC GAAACAAGAGCTTTGGAAGAACCCTTTACCGACTTCGATTT TGATTTTGAACCCAAAGTTATTGAAGAATTTACTGTAAAAA GAAGTGATATAGACACAAACAGCCACGTAAACAACAAGA AATACGTTGACTGGATTATGGAAACCGTACCCAGCAAAT ATATGACAACTACAAAGTTACATCTCTTCAGATTATATACA |

-continued

| | | Sequence Table |
|---|---|---|
| SEQ ID NO: | Description | Sequence |

|  |  | AAAAGGAATCTTCTTTGGGTTCAGGCATAAAGGCCGGATG |
|---|---|---|
|  |  | TGTAATTGATGAGCAAAATACCGATAATCCGCGGCTCCTTC |
|  |  | ACAAAATATGGGACAAGAATACCGGTTTGGAGCTTGTATC |
|  |  | CGCCGAAACAATCTGGCAAAAGATTCAGTCATAA |
| 10 | A3DJY9_HUN T2 Acyl-ACP thioesterase, *Hungateiclostridium thermocellum* | MQKKRFSKKYEVHYYEINSMQEATLLSLLNYMEDCAISHSTS AGYGVNELLAADAGWVLYRWLIKIDRLPKLGETITVQTWAS SFERFYGNREFIVLDGRDNPIVKASSVWIYFNIKKRKPMRIPLE MGDAYGIDETRALEEPFTDFDFDFEPKVIEEFTVKRSDIDTNSH VNNKKYVDWIMETVPQQIYDNYKVTSLQIIYKKESSLGSGIK AGCVIDEQNTDNPRLLHKIWDKNTGLE |
| 11 | CCB49392.1 *Vitis vinifera* (wine grape) novel gene | ATGGCTTCCATGCACCGCTCTGTGTCCAGGGAGATTAAGAA TACAAAGAAGACTTCTAGCTCTCCTCGCAAGGTGCAAGTA ACCCATTCAATGCCACCACACAAGATTGAGATTTTCAAATC CATGGAGAATTGGGTTGAGGAGAACGTTTTAATTCACCTG AAGCCAGTTGAGAAATGTTGGCAACCTCAGGATTTTCTGCC TCATCCTGCTTCTGATGGATTTCATGAGCGAGTCGAGGAGC TAAAGGAGAGAGCAAAGGGGATCCCGGATGACTACTTTGT CGTTTTGGTTGGAGATATGATCACTGAAGAAGCCCTTCCAA CTTACCAAACACTGTTCAATACCACTGATGGAATCCGTGAT GAAACAGGTGCAAGCCCCACTTCTTGGGCAACTTGGACAA GGGCATGGACCGCTGAAGAGAACAGGCACGGTGACCTTCT TAATAAGTATCTCTATCTGTCTGGAAGAGTAGACATGAAAC AAATTGAGAAGACGATCCAGTATTTGATTAGGGCTGGAAT GGATTTCCAGACGGAAAACAATCCGTACCTTTTATTCATCT ATACTTCATTTCAAGAAAGGGCAACCTTCATATCCCATGGC AATACTGCCAGGCTCGCCAAGCAACATGGGACAAGAGCT TGGCTCAAATATGTGGCATAATAGCCTCAGATGAGAAGCG CCATGAAACTGCCTACACCAAGATAGTGGAAAAGCTCTTT GAGATTGATCCCAATGGGACTGTCTTGGCTTTTGCAGACAG GATGAGGAAGAAAATCACCATGCCGGCCCTCTTGATGTAT GATGGATGTGATGACGACCTTTTTGAACACTTCTCAGCAGT TGCTCAGCGGCTTGGTGTGTATACTGCCAAGGACTATGTTG ATAACTTAGAATTCTTTGTGGAAAGATGGAATGTGGAAAA GCTAACTGGGCTTTCTAGTGAGGGGCGAAAAGCTCAGGAT TATGTTTGTGGGTTAGCTAAAAGATTGAGAACACTGGAGG AGAGAGCTCAAGAAAAGGCTAAGCAAGCACCCACCATTCC TTTCAGTTGGATTTTTGATAGAGAAGTGAAGCTCTGA |
| 12 | F6HB23_VITV I Novel protein (*Vitis vinifera*) | MASMHRSVSREIKNTKKTSSSPRKVQVTHSMPPHKIEIFKSME NWVEENVLIHLKPVEKCWQPQDFLPHPASDGFHER VEELKER AKGIPDDYFVVLVGDMITEEALPTYQTLFNTTDGIRDETGASP TSWATWTRAWTAEENRHGDLLNKYLYLSGRVDMKQIEKTIQ YLIRAGMDFQTENNPYLLFIYTSFQERATFISHGNTARLAKQH GDKSLAQICGIIASDEKRHETAYTKIVEKLFEIDPNGTVLAFAD RMRKKITMPALLMYDGCDDDLFEHFSAVAQRLGVYTAKDY VDNLEFFVERWNVEKLTGLSSEGRKAQDYVCGLAKRLRTLE ERAQEKAKQAPTIPFSWIFDREV |
| 13 | Flavodoxin/ferr edoxin-NADP+ reductase, fpr, *Escherichia coli*, DNA sequence | ATGGCTGATTGGGTAACAGGCAAAGTCACTAAAGTGCAGA ACTGGACCGACGCCCTGTTTAGTCTCACCGTTCACGCCCCC GTGCTTCCGTTTACCGCCGGGCAATTTACCAAGCTTGGCCT TGAAATCGACGGCGAACGCGTCCAGCGCGCCTACTCCTAT GTAAACTCGCCCGATAATCCCGATCTGGAGTTTTACCTGGT CACCGTCCCCGATGGCAAATTAAGCCCACGACTGGCGGCA CTGAAACCAGGCGATGAAGTGCAGGTGGTTAGCGAAGCGG CAGGATTCTTTGTGCTCGATGAAGTGCCGCACTGCGAAACG CTATGGATGCTGGCAACCGGTACAGCGATTGGCCCTTATTT ATCGATTCTGCAACTAGGTAAAGATTTAGATCGCTTCAAAA ATCTGGTCCTGGTGCACGCCGCACGTTATGCCGCCGACTTA AGCTATTTGCCACTGATGCAGGAACTGGAAAAACGCTACG AAGGAAAACTGCGCATTCAGACGGTGGTCAGTCGGGAAAC GGCAGCGGGGTCGCTCACCGGACGGATACCGGCATTAATT GAAAGTGGGGAACTGGAAAGCACGATTGGCCTGCCGATGA ATAAAGAAACCAGCCATGTGATGCTGTGCGGCAATCCACA GATGGTGCGCGATACACAACAGTTGCTGAAAGAGACCCGG CAGATGACGAAACATTTACGTCGCCGACCGGGCCATATGA CAGCGGAGCATTACTGGTAA |

-continued

| Sequence Table | | |
|---|---|---|
| SEQ ID NO: | Description | Sequence |
| 14 | Flavodoxin/ferr edoxin-NADP+ reductase, Fpr, *Escherichia coli*, protein | MADWVTGKVTKVQNWTDALFSLTVHAPVLPFTAGQFTKLG LEIDGERVQRAYSYVNSPDNPDLEFYLVTVPDGKLSPRLAAL KPGDEVQVVSEAAGFFVLDEVPHCETLWMLATGTAIGPYLSI LQLGKDLDRFKNLVLVHAARYAADLSYLPLMQELEKRYEGK LRIQTVVSRETAAGSLTGRIPALIESGELESTIGLPMNKETSHV MLCGNPQMVRDTQQLLKETRQMTKHLRRRPGHMTAEHY |
| 15 | 3-hydroxy-acyl-[acyl-carrier-protein] dehydratase, FabZ, *Acinetobacter baylyi*, DNA sequence | ATGATGACTGAGTCAAACACTCCTGCGTTTACGATCCCTGA ATTGCCAATGGACATTCAAAAAATTCGTGAATATTTGCCAC ATCGCTATCCATTCCTATTGGTTGATCGTGTAGTTGAAGTT GGTGAAAATAATATTGTTGGCTATAAAAACGTTTCGATTAA CGAAGAGTTTTTTCAGGGCCATTTTCCTGATTATCCGATTA TGCCAGGTGTCTTGATTGTAGAGGCTTTGGCACAAATTTCT GGTATTTTGGGTTTTATTATGAATAATGAAACTCCTAAACC AGGTTCTTTGTTTCTGTTCGCAGGGGCTGAGAAAGTTCGTT TCAAAAAACAAGTGGTTGCTGGTGATCAGCTCGTTTTAAAA GCTGAACTTGTCATGCAAAAACGTGGTATCTACAAATACA ATTGTACTGCTACGGTTGATGGTAAAGTCGCTACAACCGCT GAAATTATAGTTTCGCATTTAAGAACAGAGCAGGCATG |
| 16 | 3-hydroxy-acyl-[acyl-carrier-protein] dehydratase, FabZ, *Acinetobacter baylyi*, protein | MMTESNTPAFTIPELPMDIQKIREYLPHRYPFLLVDRVVEVGE NNIVGYKNVSINEEFFQGHFPDYPIMPGVLIVEALAQISGILGFI MNNETPKPGSLFLFAGAEKVRFKKQVVAGDQLVLKAELVMQ KRGIYKYNCTATVDGKVATTAEIIVSHLRTEQA |
| 17 | Carboxylic Acid Reductase, CarB, *Mycobacterium smegmatis*, DNA sequence | ATGGGCACGAGCGATGTTCACGACGCGACCGACGGCGTTA CCGAGACTGCACTGGATGATGAGCAGAGCACTCGTCGTAT TGCAGAACTGTACGCAACGGACCCAGAGTTCGCAGCAGCA GCTCCTCTGCCGGCCGTTGTCGATGCGGCGCACAAACCGG GCCTGCGTCTGGCCGGAAATCCTGCAGACCCTGTTCACCGGC TACGGCGATCGTCCGGCGCTGGGCTATCGTGCACGTGAGCT GGCGACGGACGAAGGCGGTCGTACGGTCACGCGTCTGCTG CCGCGCTTCGATACCCTGACCTATGCACAGGTGTGGAGCCG TGTTCAAGCAGTGGCTGCAGCGTTGCGTCACAATTTCGCAC AACCGATTTACCCGGGCGACGCGGTCGCGACTATCGGCTTT GCGAGCCCGGACTATTTGACGCTGGATCTGGTGTGCGCGTA TCTGGGCCTGGTCAGCGTTCCTTTGCAGCATAACGCTCCGG TGTCTCGCCTGGCCCCGATTCTGGCCGAGGTGGAACCGCGT ATTCTGACGGTGAGCGCAGAATACCTGGACCTGGCGGTTG AATCCGTCCGTGATGTGAACTCCGTCAGCCAGCTGGTTGTT TTCGACCATCATCCGGAAGTGGACGATCACCGTGACGCAC TGGCTCGCGCACGCGAGCAGCTGGCCGGCAAAGGTATCGC AGTTACGACCCTGGATGCGATCGCAGACGAAGGCGCAGGT TTGCCGGCTGAGCCGATTTACACGGCGGATCACGATCAGC GTCTGGCCATGATTCTGTATACCAGCGGCTCTACGGGTGCT CCGAAAGGCGCGATGTACACCGAAGCGATGGTGGCTCGCC TGTGGACTATGAGCTTTATCACGGGCGACCCGACCCCGGTT ATCAACGTGAACTTCATGCCGCTGAACCATCTGGGCGGTCG TATCCCGATTAGCACCGCCGTGCAGAATGGCGGTACCAGC TACTTCGTTCCGGAAAGCGACATGAGCACGCTGTTTGAGG ATCTGGCCCTGGTCCGCCCTACCGAACTGGGTCTGGTGCCG CGTGTTGCGGACATGCTGTACCAGCATCATCTGGCGACCGT GGATCGCCTGGTGACCCAGGGCGCGGACGAACTGACTGCG GAAAAGCAGGCCGGTGCGGAACTGCGTGAACAGGTCTTGG GCGGTCGTGTTATCACCGGTTTTGTTTCCACCGCGCCGTTG GCGGCAGAGATGCGTGCTTTTCTGGATATCACCTTGGGTGC ACACATCGTTGACGGTTACGGTCTGACCGAAACCGGTGCG GTCACCCGTGATGGTGTGATTGTTCGTCCTCCGGTCATTGA TTACAAGCTGATCGATGTGCCGGAGCTGGGTTACTTCTCCA CCGACAAACCGTACCCGCGTGGCGAGCTGCTGGTTCGTAG CCAAACGTTGACTCCGGGTTACTACAAGCGCCCAGAAGTC ACCGCGTCCGTTTTCGATCGCGACGGCTATTACCACACCGG CGACGTGATGGCAGAAACCGCGCCAGACCACCTGGTGTAT GTGGACCGCCGCAACAATGTTCTGAAGCTGGCGCAAGGTG AATTTGTCGCCGTGGCTAACCTGGAGGCCGTTTTCAGCGGC GCTGCTCTGGTCCGCCAGATTTTCGTGTATGGTAACAGCGA GCGCAGCTTTCTGTTGGCTGTTGTTGTCCCTACCCCCGGAGG CGCTGGAGCAATACGACCCTGCCGCATTGAAAGCAGCCCT GGCGGATTCGCTGCAGCGTACGGCGCGTGATGCCGAGCTG CAGAGCTATGAAGTGCCGGCGGACTTCATTGTTGAGACTG AGCCTTTTAGCGCTGCGAACGGTCTGCTGAGCGGTGTTGGC |

| Sequence Table | | |
| --- | --- | --- |
| SEQ ID NO: | Description | Sequence |
| | | AAGTTGCTGCGTCCGAATTTGAAGGATCGCTACGGTCAGC |
| | | GTTTGGAGCAGATGTACGCGGACATCGCGGCTACGCAGGC |
| | | GAACCAATTGCGTGAACTGCGCCGTGCTGCGGCTACTCAA |
| | | CCGGTGATCGACACGCTGACGCAAGCTGCGGCGACCATCC |
| | | TGGGTACCGGCAGCGAGGTTGCAAGCGACGCACACTTTAC |
| | | TGATTTGGGCGGTGATTCTCTGAGCGCGCTGACGTTGAGCA |
| | | ACTTGCTGTCTGACTTCTTTGGCTTTGAAGTCCCGGTTGGC |
| | | ACGATTGTTAACCCAGCGACTAATCTGGCACAGCTGGCGC |
| | | AACATATCGAGGCGGCAGCGCACGGCGGGTGACCGCCGTCC |
| | | ATCCTTTACGACGGTCCACGGTGCGGATGCTACGGAAATCC |
| | | GTGCAAGCGAACTGACTCTGGACAAATTCATCGACGCTGA |
| | | GACTCTGCGCGCAGCACCTGGTTTGCCGAAGGTTACGACTG |
| | | AGCCGCGTACGGTCCTGTTGAGCGGTGCCAATGGTTGGTTG |
| | | GGCCGCTTCCTGACCCTGCAGTGGCTGGAACGTTTGGCACC |
| | | GGTTGGCGGTACCCTGATCACCATTGTGCGCGGTCGTGACG |
| | | ATGCAGCGGCACGTGCACGTTTGACTCAGGCTTACGATAC |
| | | GGACCCAGAGCTGTCCCGCCGCTTCGCTGAGTTGGCGGATC |
| | | GCCACTTGCGTGTGGTGGCAGGTGATATCGGCGATCCGAA |
| | | TCTGGGCCTGACCCCGGAGATTTGGCACCGTCTGGCAGCA |
| | | GAGGTCGATCTGGTCGTTCATCCAGCGGCCCTGGTCAACCA |
| | | CGTCCTGCCGTACCGCCAGCTGTTTGGTCCGAATGTTGTTG |
| | | GCACCGCCGAAGTTATCAAGTTGGCTCTGACCGAGCGCAT |
| | | CAAGCCTGTTACCTACCTGTCCACGGTTAGCGTCGCGATGG |
| | | GTATTCCTGATTTTGAGGAGGACGGTGACATTCGTACCGTC |
| | | AGCCCGGTTCGTCCGCTGGATGGTGGCTATGCAAATGGCTA |
| | | TGGCAACAGCAAGTGGGCTGGCGAGGTGCTGCTGCGCGAG |
| | | GCACATGACCTGTGTGGCCTGCCGGTTGCGACGTTTCGTAG |
| | | CGACATGATTCTGGCCCACCCGCGCTACCGTGGCCAAGTG |
| | | AATGTGCCGGACATGTTCACCCGTCTGCTGCTGTCCCTGCT |
| | | GATCACGGGTGTGGCACCGCGTTCCTTCTACATTGGTGATG |
| | | GCGAGCGTCCGCGTGCACACTACCCGGGCCTGACCGTCGA |
| | | TTTTGTTGCGGAAGCGGTTACTACCCTGGGTGCTCAGCAAC |
| | | GTGAGGGTTATGTCTCGTATGACGTTATGAATCCGCACGAT |
| | | GACGGTATTAGCTTGGATGTCTTTGTGGACTGGCTGATTCG |
| | | TGCGGGCCACCCAATTGACCGTGTTGACGACTATGATGACT |
| | | GGGTGCGTCGTTTTGAAACCGCGTTGACCGCCTTGCCGGAG |
| | | AAACGTCGTGCGCAGACCGTTCTGCCGCTGCTGCATGCCTT |
| | | TCGCGCGCCACAGGCGCCGTTGCGTGGCGCCCCTGAACCG |
| | | ACCGAAGTGTTTCATGCAGCGGTGCGTACCGCTAAAGTCG |
| | | GTCCGGGTGATATTCCGCACCTGGATGAAGCCCTGATCGAC |
| | | AAGTACATCCGTGACCTGCGCGAGTTCGGTCTGATTTAG |
| 18 | Carboxylic Acid Reductase, CarB, *Mycobacterium smegmatis*, protein | MGTSDVHDATDGVTETALDDEQSTRRIAELYATDPEFAAAAP LPAVVDAAHKPGLRLAEILQTLFTGYGDRPALGYRARELATD EGGRTVTRLLPRFDTLTYAQVWSRVQAVAAALRHNFAQPIYP GDAVATIGFASPDYLTLDLVCAYLGLVSVPLQHNAPVSRLAPI LAEVEPRILTVSAEYLDLAVESVRDVNSVSQLVVFDHHPEVD DHRDALARAREQLAGKGIAVTTLDAIADEGAGLPAEPIYTAD HDQRLAMILYTSGSTGAPKGAMYTEAMVARLWTMSFITGDP TPVINVNFMPLNHLGGRIPISTAVQNGGTSYFVPESDMSTLFE DLALVRPTELGLVPRVADMLYQHHLATVDRLVTQGADELTA EKQAGAELREQVLGGRVITGFVSTAPLAAEMRAFLDITLGAHI VDGYGLTETGAVTRDGVIVRPPVIDYKLIDVPELGYFSTDKPY PRGELLVRSQTLTPGYYKRPEVTASVFDRDGYYHTGDVMAE TAPDHLVYVDRRNNVLKLAQGEFVAVANLEAVESGAALVRQ IFVYGNSERSFLLAVVVPTPEALEQYDPAALKAALADSLQRT ARDAELQSYEVPADFIVETEPFSAANGLLSGVGKLLRPNLKDR YGQRLEQMYADIAATQANQLRELRRAAATQPVIDTLTQAAA TILGTGSEVASDAHFTDLGGDSLSALTLSNLLSDFFGFEVPVG TIVNPATNLAQLAQHIEAQRTAGDRRPSFTTVHGADATEIRAS ELTLDKFIDAETLRAAPGLPKVTTEPRTVLLSGANGWLGRFLT LQWLERLAPVGGTLITIVRGRDDAAARARLTQAYDTDPELSR RFAELADRHLRVVAGDIGDPNLGLTPEIWHRLAAEVDLVVHP AALVNHVLPYRQLFGPNVVGTAEVIKLALTERIKPVTYLSTVS VAMGIPDFEEDGDIRTVSPVRPLDGGYANGYGNSKWAGEVL LREAHDLCGLPVATFRSDMILAHPRYRGQVNVPDMFTRLLLS LLITGVAPRSFYIGDGERPRAHYPGLTVDFVAEAVTTLGAQQR EGYVSYDVMNPHDDGISLDVFVDWLIRAGHPIDRVDDYDDW VRRFETALTALPEKRRAQTVLPLLHAFRAPQAPLRGAPEPTEV FHAAVRTAKVGPGDIPHLDEALIDKYIRDLREFGLI* |
| 19 | Alcohol dehydrogenase, AlrA, *Acinetobacter* | ATGGCAACAACTAATGTGATTCATGCTTATGCTGCAATGCA GGCAGGTGAAGCACTCGTGCCTTATTCGTTTGATGCAGGCG AACTGCAACCACATCAGGTTGAAGTTAAAGTCGAATATTG TGGGCTGTGCCATTCCGATGTCTCGGTACTCAACAACGAAT |

| | | Sequence Table |
|---|---|---|
| SEQ ID NO: | Description | Sequence |
| | *baylyi*, DNA sequence | GGCATTCTTCGGTTTATCCAGTCGTGGCAGGTCATGAAGTG ATTGGTACGATTACCCAACTGGGAAGTGAAGCCAAAGGAC TAAAAATTGGTCAACGTGTTGGTATTGGCTGGACGGCAGA AAGCTGTCAGGCCTGTGACCAATGCATCAGTGGTCAGCAG GTATTGTGCACGGGCGAAAATACCGCAACTATTATTGGTCA TGCTGGTGGCTTTGCAGATAAGGTTCGTGCAGGCTGGCAAT GGGTCATTCCCCTGCCCGACGAACTCGATCCGACCAGTGCT GGTCCTTTGCTGTGTGGCGGAATCACAGTATTTGATCCAAT TTTAAAACATCAGATTCAGGCTATTCATCATGTTGCTGTGA TTGGTATCGGTGGTTTGGGACATATGGCCATCAAGCTACTT AAAGCATGGGGCTGTGAAATTACTGCGTTTAGTTCAAATCC AAACAAAACCGATGAGCTCAAAGCTATGGGGGCCGATCAC GTGGTCAATAGCCGTGATGATGCCGAAATTAAATCGCAAC AGGGTAAATTTGATTTACTGCTGAGTACAGTTAATGTGCCT TTAAACTGGAATGCGTATCTAAACACACTGGCACCCAATG GCACTTTCCATTTTTTGGGCGTGGTGATGGAACCAATCCCT GTACCTGTCGGTGCGCTGCTAGGAGGTGCCAAATCGCTAA CAGCCATCACCAACTGGCTCGCCTGCTGCCTTACGTAAGCTG CTCGAATTTGCGGCACGTAAGAATATCGCACCTCAAATCG AGATGTATCCTATGTCGGAGCTGAATGAGGCCATCGAACG CTTACATTCGGGTCAAGCACGTTATCGGATTGTACTTAAAG CCGATTTTTAA |
| 20 | Alcohol dehydrogenase, AlrA, *Acinetobacter baylyi*, protein | MATTNVIHAYAAMQAGEALVPYSFDAGELQPHQVEVKVEYC GLCHSDVSVLNNEWHSSVYPVVAGHEVIGTITQLGSEAKGLK IGQRVGIGWTAESCQACDQCISGQQVLCTGENTATIIGHAGGF ADKVRAGWQWVIPLPDELDPTSAGPLLCGGITVFDPILKHQIQ AIHHVAVIGIGGLGHMAIKLLKAWGCEITAFSSNPNKTDELKA MGADHVVNSRDDAEIKSQQGKFDLLLSTVNVPLNWNAYLNT LAPNGTFHFLGVVMEPIPVPVGALLGGAKSLTASPTGSPAALR KLLEFAARKNIAPQIEMYPMSELNEAIERLHSGQARYRIVLKA DF |
| 21 | Hybrid fusion cytochrome P450 Cyp153A16(G3 07A)-RedRhF Fusion Protein, DNA Sequence | ATGCCAACACTGCCCAGAACATTTGACGACATTCAGTCCCG ACTGATTAACGCCACCTCCAGGGTGGTGCCGATGCAGAGG CAAATTCAGGGACTGAAATTCTTAATGAGCGCCAAGAGGA AGACCTTCGGCCCACGCCGACCGATGCCCGAATTCGTTGA AACACCCATCCCGGACGTTAACACGCTGGCCCTTGAGGAC ATCGATGTCAGCAATCCGTTTTTATACCGGCAGGGTCAGTG GCGCGCCTATTTCAAACGGTTGCGTGATGAGGCGCCGGTCC ATTACCAGAAGAACAGCCCTTTCGGCCCCTTCTGGTCGGTA ACTCGGTTTGAAGACATCCTGTTCGTGGATAAGAGTCACGA CCTGTTTTCCGCCGAGCCGCAAATCATTCTCGGTGACCCTC CGGAGGGGCTGTCGGTGGAAATGTTCATAGCGATGGATCC GCCGAAACACGATGTGCAGCGCAGCTCGGTGCAGGGAGTA GTGGCACCGAAAAACCTGAAGGAGATGGAGGGGCTGATCC GATCACGCACCGGCGATGTGCTTGACAGCCTGCCTACAGA CAAACCCTTTAACTGGGTACCTGCTGTTTCCAAGGAACTCA CAGGCCGCATGCTGGCGACGCTTCTGGATTTTCCTTACGAG GAACGCCACAAGCTGGTTGAGTGGTCGGACAGAATGGCAG GTGCAGCATCGGCCACCGGCGGGGAGTTTGCCGATGAAAA TGCCATGTTTGACGACGCGGCAGACATGGCCCGGTCTTTCT CCAGGCTTTGGCGGGACAAGGAGGCGCGCCGCGCAGCAGG CGAGGAGCCCGGTTTCGATTTGATCAGCCTGTTGCAGAGCA ACAAAGAAACGAAAGACCTGATCAATCGGCCGATGGAGTT TATCGGTAATTTGACGCTGCTCATAGTCGcCGGCAACGATA CGACGCGCAACTCGATGAGTGGTGGCCTGGTGGCCATGAA CGAATTCCCCAGGGAATTTGAAAAATTGAAGGCAAAACCG GAGTTGATTCCGAACATGGTGTCGGAAATCATCCGCTGGC AAACGCCGCTGGCCTATATGCGCCGAATCGCCAAGCAGGA TGTCGAACTGGGCGGCCAGACCATCAAGAAGGGTGATCGA GTTGTCATGTGGTACGCGTCGGGTAACCGGGACGAGCGCA AATTTGACAACCCCGATCAGTTCATCATTGATCGCAAGGAC GCACGAAACCACATGTCGTTCGGCTATGGGGTTCACCGTTG CATGGGCAACCGTCTGGCTGAACTGCAACTGCGCATCCTCT GGGAAGAAATACTCAAGCGTTTTGACAACATCGAAGTCGT CGAAGAGCCCGAGCGGGTGCAGTCCAACTTCGTGCGGGGC TATTCCAGGTTGATGGTCAAACTGACACCGAACAGTGTACT CCATCGTCATCAACCTGTCACCATCGGCGAGCCGGCCGCTC GTGCTGTGAGCCGCACGGTGACCGTTGAGCGTCTTGATCGC ATTGCCGACGATGTCCTTCGCCTGGTCCTTCGCGATGCTGG AGGTAAAACCCTCCCGACGTGGACGCCTGGCGCTCACATC GACCTGGATCTGGGtGCTCTGAGCCGTCAGTATTCGCTCTG CGGCGCTCCGGATGCTCCGTCGTACGAAATCGCCGTGCACT TAGATCCgGAAAGCCGTGGTGGAAGCCGCTATATTCATGAA |

-continued

| | | Sequence Table |
|---|---|---|
| SEQ ID NO: | Description | Sequence |

| | | |
|---|---|---|
| | | CAGCTGGAAGTTGGAAGTCCGCTGCGTATGCGtGGCCCACG<br>CAACCATTTCGCCCTGGATCCGGGtGCGGAACATTACGTGT<br>TTGTTGCCGGGGGTATCGGCATCACGCCGGTGCTGGCAATG<br>GCGGATCATGCCCGTGCGCGTGGTTGGTCGTACGAACTGC<br>ATTATTGTGGTCGTAATCGTAGCGGTATGGCTTACCTGGAA<br>CGCGTCGCGGGACATGGTGACCGCGCtGCCTTGCACGTATC<br>TGAAGAAGGCACCCGCATTGATCTGGCGGCATTACTTGCTG<br>AACCGGCGCCGGGCGTGCAAATCTACGCCTGCGGTCCGGG<br>CCGTTTATTAGCGGGTCTTGAAGACGCGTCTCGTAATTGGC<br>CGGATGGCGCGCTTCATGTGGAGCATTTCACTTCGAGTTTA<br>GCCGCTTTGGATCCGGATGTCGAACATGCCTTTGATTTGGA<br>GCTGCGTGACTCTGGCCTTACCGTTCGCGTCGAGCCAACTC<br>AGACCGTTTTAGACGCTTTGCGTGCGAACAATATCGACGTC<br>CCGTCGGATTGCGAAGAGGGGCTGTGTGGTTCTTGCGAAG<br>TAGCCGTTCTGGATGGCGAGGTTGATCACCGTGATACCGTT<br>CTGACTAAGGCCGAGCGCGCCGCGAATCGTCAGATGATGA<br>CTTGCTGCAGTCGTGCATGCGGTGATCGTCTGGCGCTGCGC<br>CTCTAA |
| 22 | Hybrid fusion<br>cytochrome<br>P450<br>Cyp153A16(G3<br>07A)-RedRhF<br>Fusion Protein<br>Sequence | MPTLPRTFDDIQSRLINATSRVVPMQRQIQGLKFLMSAKRKTF<br>GPRRPMPEFVETPIPDVNTLALEDIDVSNPFLYRQGQWRAYFK<br>RLRDEAPVHYQKNSPFGPFWSVTRFEDILFVDKSHDLFSAEPQ<br>IILGDPPEGLSVEMFIAMDPPKHDVQRSSVQGVVAPKNLKEM<br>EGLIRSRTGDVLDSLPTDKPFNWVPAVSKELTGRMLATLLDFP<br>YEERHKLVEWSDRMAGAASATGGEFADENAMEDDAADMA<br>RSFSRLWRDKEARRAAGEEPGFDLISLLQSNKETKDLINRPME<br>FIGNLTLLIVAGNDTTRNSMSGGLVAMNEFPREFEKLKAKPEL<br>IPNMVSEIIRWQTPLAYMRRIAKQDVELGGQTIKKGDRVVMW<br>YASGNRDERKFDNPDQFIIDRKDARNHMSFGYGVHRCMGNR<br>LAELQLRILWEEILKRFDNIEVVEEPERVQSNFVRGYSRLMVK<br>LTPNSVLHRHQPVTIGEPAARAVSRTVTVERLDRIADDVLRLV<br>LRDAGGKTLPTWTPGAHIDLDLGALSRQYSLCGAPDAPSYEI<br>AVHLDPESRGGSRYIHEQLEVGSPLRMRGPRNHFALDPGAEH<br>YVFVAGGIGITPVLAMADHARARGWSYELHYCGRNRSGMA<br>YLERVAGHGDRAALHVSEEGTRIDLAALLAEPAPGVQIYACG<br>PGRLLAGLEDASRNWPDGALHVEHFTSSLAALDPDVEHAFDL<br>ELRDSGLTVRVEPTQTVLDALRANNIDVPSDCEEGLCGSCEV<br>AVLDGEVDHRDTVLTKAERAANRQMMTCCSRACGDRLALRL |
| 23 | Alcohol acetyl-<br>CoA transferase<br>Atf1,<br>*Saccharomyces<br>cerevisiae*,<br>DNA Sequence | ATGAACGAAATCGACGAAAAAAACCAGGCTCCGGTTCACC<br>AGGAATGCCTGAAAGAAATGATCCAGAACGGTCACGCTCG<br>TCGTATGGGTTCTGTTGAAGACCTGTACGTTGCTCTGAACC<br>GTCAGAACCTGTACCGTAACTTCTGCACCTACGGTGAACTG<br>TCTGACTACTGCACCCGTGACCAGCTGACCCTGGCTCTGCG<br>TGAAATCTGCCTGAAAAACCCGACCCTGCTGCACATCGTTC<br>TGCCGACCCGTTGGCCGAACCACGAAAACTACTACCGTTCT<br>TCTGAATACTACTCTCGTCCGCACCCGGTTCACGACTACAT<br>CTCTGTTCTGCAGGAACTGAAACTGTCTGGTGTTGTTCTGA<br>ACGAACAGCCGGAATACTCTGCTGTTATGAAACAGATCCT<br>GGAAGAATTCAAAAACTCTAAAGGTTCTTACACCGCTAAA<br>ATCTTCAAACTGACCACCACCCTGACCATCCCGTACTTCGG<br>TCCGACCGGTCCGTCTTGGCGTCTGATCTGCCTGCCGGAAG<br>AACACACCGAAAATGGAAAAAATTCATCTTCGTTTCTAA<br>CCACTGCATGTCTGACGGTCGTTCTTCTATCCACTTCTTCCA<br>CGACCTGCGTGACGAACTGAACAACATCAAAACCCCGCCG<br>AAAAAACTGGACTACATCTTCAAATACGAAGAAGACTACC<br>AGCTGCTGCGTAAACTGCCGGAACCGATCGAAAAAGTTAT<br>CGACTTCCGTCCGCCGTACCTGTTCATCCCGAAATCTCTGC<br>TGTCTGGTTTCATCTACAACCACCTGCGTTTCTCTTCTAAAG<br>GTGTTTGCATGCGTATGGACGACGTTGAAAAAACCGACGA<br>CGTTGTTACCGAAATCATCAACATCTCTCCGACCGAATTCC<br>AGGCTATCAAAGCTAACATCAAATCTAACATCCAGGGTAA<br>ATGCACCATCACCCCGTTCCTGCACGTTTGCTGGTTCGTTTC<br>TCTGCACAAATGGGGTAAATTCTTCAAACCGCTGAACTTCG<br>AATGGCTGACCGACATCTTCATCCCGGCTGACTGCCGTTCT<br>CAGCTGCCGGACGACGACGAAATGCGTCAGATGTACCGTT<br>ACGGTGCTAACGTTGGTTTCATCGACTTCACCCCGTGGATC<br>TCTGAATTCGACATGAACGACAACAAAGAAACTTCTGGC<br>CGCTGATCGAACACTACCACGAAGTTATCTCTGAAGCTCTG<br>CGTAACAAAAAACACCTGCACGGTCTGGGGTTTCAACATCC<br>AGGGTTTCGTTCAGAAATACGTTAACATCGACAAAGTTATG<br>TGCGACCGTGCTATCGGTAAACGTCGTGGTGGTACCCTGCT<br>GTCTAACGTTGGTCTGTTCAACCAGCTGGAAGAACCGGAC<br>GCTAAATACTCTATCTGCGACCTGGCTTTCGGTCAGTTCCA<br>GGGTTCTTGGCACCAGGCTTTCTCTCTGGGTGTTTGCTCTAC |

-continued

| | | Sequence Table | |
|---|---|---|---|

| SEQ ID NO: | Description | Sequence |
|---|---|---|
| | | CAACGTTAAAGGTATGAACATCGTTGTTGCTTCTACCAAAA<br>ACGTTGTTGGTTCTCAGGAATCTCTGGAAGAACTGTGCTCT<br>ATCTACAAAGCTCTGCTGCTGGGTCCGTAG |
| 24 | Alcohol acetyl-<br>CoA transferase<br>Atf1,<br>*Saccharomyces*<br>*cerevisiae*,<br>protein<br>sequence | MNEIDEKNQAPVHQECLKEMIQNGHARRMGSVEDLYVALNR<br>QNLYRNFCTYGELSDYCTRDQLTLALREICLKNPTLLHIVLPT<br>RWPNHENYYRSSEYYSRPHPVHDYISVLQELKLSGVVLNEQP<br>EYSAVMKQILEEFKNSKGSYTAKIFKLTTTLTIPYFGPTGPSWR<br>LICLPEEHTEKWKKFIFVSNHCMSDGRSSIHFFHDLRDELNNIK<br>TPPKKLDYIFKYEEDYQLLRKLPEPIEKVIDFRPPYLFIPKSLLS<br>GFIYNHLRFSSKGVCMRMDDVEKTDDVVTEIINISPTEFQAIK<br>ANIKSNIQGKCTITPFLHVCWFVSLHKWGKFFKPLNFEWLTDI<br>FIPADCRSQLPDDDEMRQMYRYGANVGFIDFTPWISEFDMND<br>NKENFWPLIEHYHEVISEALRNKKHLHGLGFNIQGFVQKYVNI<br>DKVMCDRAIGKRRGGTLLSNVGLFNQLEEPDAKYSICDLAFG<br>QFQGSWHQAFSLGVCSTNVKGMNIVVASTKNVVGSQESLEE<br>LCSIYKALLLGP |
| 25 | Phosphopantetheinyl<br>transferase<br>EntD, DNA<br>Sequence | ATGAAAACTACGCATACCTCCCTCCCCTTTGCCGGACATAC<br>GCTGCATTTTGTTGAGTTCGATCCGGCGAATTTTTGTGAGC<br>AGGATTTACTCTGGCTGCCGCACTACGCACAACTGCAACAC<br>GCTGGACGTAAACGTAAAACAGAGCATTTAGCCGGACGGA<br>TCGCTGCTGTTTATGCTTTGCGGGAATATGGCTATAAATGT<br>GTGCCCGCAATCGGCGAGCTACGCCAACCTGTCTGGCCTGC<br>GGAGGTATACGGCAGTATTAGCCACTGTGGGACTACGGCA<br>TTAGCCGTGGTATCTCGTCAACCGATTGGCATTGATATAGA<br>AGAAATTTTTTCTGTACAAACCGCAAGAGAATTGACAGAC<br>AACATTATTACACCAGCGGAACACGAGCGACTCGCAGACT<br>GCGGTTTAGCCTTTTCTCTGGCGCTGACACTGGCATTTTCC<br>GCCAAAGAGAGCGCATTTAAGGCAAGTGAGATCCAAACTG<br>ATGCAGGTTTTCTGGACTATCAGATAATTAGCTGGAATAAA<br>CAGCAGGTCATCATTCATCGTGAGAATGAGATGTTTGCTGT<br>GCACTGGCAGATAAAAGAAAAGATAGTCATAACGCTGTGC<br>CAACACGATTAA |
| 26 | Phosphopantetheinyl<br>transferase<br>EntD, protein | MKTTHTSLPFAGHTLHFVEFDPANFCEQDLLWLPHYAQLQH<br>AGRKRKTEHLAGRIAAVYALREYGYKCVPAIGELRQPVWPA<br>EVYGSISHCGTTALAVVSRQPIGIDIEEIFSVQTARELTDNIITPA<br>EHERLADCGLAFSLALTLAFSAKESAFKASEIQTDAGFLDYQII<br>SWNKQQVIIHRENEMFAVHWQIKEKIVITLCQHD |
| 27 | FabZ from<br>*Clostridium*<br>*acetobutylicum*,<br>protein | MSLSIEQIMEIIPHRYPMLLVDRVEEIEPGKRAVGYKNVTFNE<br>QIFQGHYPGKPIMPGVLMIEALAQLGGVAILSLDKYKGKKPIL<br>GAVKNAKFRRMVVPGDVLKLEIEIVKVKGPAGIGKGIATVNG<br>EKAVEAEITFMIV |
| 28 | FabZ from<br>*Synechococcus*<br>*elongatus*,<br>protein | MTVNPDAPALPTLPLAVETIQGLLPHRYPFALVDRIIDYVPGE<br>RAVGIKNVTFNEPQFQGHFPGRPLMPGVLIVEAMAQVGGVIV<br>TLMPDMPQGLFVFAGIDQVRFRRPVVPGDQLVLSAQLLSVKR<br>RRFCKIQGEAMVDGQLAASGELLESLVE |
| 29 | Alcohol<br>dehydrogenase<br>from<br>*Pseudomonas*<br>*oleovorans*,<br>protein | MYDYIIVGAGSAGCVLANRLSADPSKRVCLLEAGPRDTNPLI<br>HMPLGIALLSNSKKLNWAFQTAPQQNLNGRSLFWPRGKTLG<br>GSSSINAMVYIRGHEDDYHAWEQAAGRYWGWYRALELFKR<br>LECNQRFDKSEHHGVDGELAVSDLKYINPLSKAFVQAGMEA<br>NINFNGDFNGEYQDGVGFYQVTQKNGQRWSSARAFLHGVLS<br>RPNLDIITDAHASKILFEDRKAVGVSYIKKNMHHQVKTTSGGE<br>VLLSLGAVGTPHLLMLSGVGAAAELKEHGVSLVHDLPEVGK<br>NLQDHLDITLMCAANSREPIGVALSFIPRGVSGLFSYVFKREG<br>FLTSNVAESGGFVKSSPDRDRPNLQFHFLPTYLKDHGRKIAGG<br>YGYTLHICDLLPKSRGRIGLKSANPLQPPLIDPNYLSDHEDIKT<br>MIAGIKIGRAILQAPSMAKHFKHEVVPGQAVKTDDEIIEDIRRR<br>AETIYHPVGTCRMGKDPASVVDPCLKIRGLANIRVVDASIMP<br>HLVAGNTNAPTIMIAENAAEIIMRNLDVEALEASAEFAREGAE<br>LELAMIAVCM |
| 30 | Acetaldehyde<br>dehydrogenase<br>2 from<br>*Acinetobacter*<br>*baylyi*, protein | MRYIDPNQPGSKVQFKAQYENFIGGQWVPPVKGEYFGNSSPV<br>DGKVFTQIPRSSVEDIELALDAAHKAKADWNKASPTVRSNVL<br>LKIADRLEENLELLAVAETWENGKPIRETLAADIPLAIDHFRYF<br>AGCIRAQEGGISEIDEDTIAYHFHEPLGVVGQIIPWNFPILMAA<br>WKLAPALAAGNCIVLKPAEQTPSSILVLAELIQDLLPPGVLNIV<br>NGYGAEVGRPLATNPRISKIAFTGSTKVGQMIMQYATENIIPV<br>TLELGGKSPNIFFEDILDKEDDYLEKTLEGFAMFALNQGEVCT<br>CPSRALVQESIADKFLEMAVERVKRIKTGHPLDTETMIGAQAS<br>KQQFDKILGCIDTGRNEGAQLLTGGDARHDVDGGFYIEPTIFK |

-continued

| | | Sequence Table |
|---|---|---|
| SEQ ID NO: | Description | Sequence |
| | | GNNSMKIFQEEIFGPVLSVTTFKDFDDAMRIANDTIYGLGAGV WSRSAHTSYRAGRAIEAGRVWTNCYHLYPAHAAFGGYKQSG IGRENHRMMLDHYQQTKNLLVSYSTKPMGFF |
| 31 | Acetaldehyde dehydrogenase from *Marinobacter aquaeoli*, protein | MIYAQPGQEGSVVSFKSRYENYIGGEWVAPVKGQYFDNITPV TGAVFCEVPRSTAEDIDLALDAAHKAAPAWGKTSPTERSNILL KIADRIEANLEKLAVAETWDNGKAVRETLNADVPLAADHLR YFAGCIRAQEGHMSEIDHNTVAYHFHEPLGVVGQIIPWNFPLL MAAWKLGPCLASGNCTVLKPAEQTPASILVLMDIIGDLLPPG VINIVNGYGIEAGQALATSKRIAKIAFTGSTPVGSHILKCAAEN IIPSTVELGGKSPNIYFSDVMKAEPEFVDKCVEGLVLAFFNQG EICTCPSRALVQEDMFEEFMQKVVERTKSIKRGNPLDTDVQV GAQASKEQFDKIMSYMEIGRQEGAVVLTGGDREHLEGEFNN GFYIQPTLFKGDNKMRVFQEEIFGPVVGVTTFKTEEEALAIAN DTEFGLGAGVWTRDTNLAYRMGRNIQAGRVWMNCYHAYP AHAAFGGYKKSGIGRENHKMALEHYQQTKCMLTSYDTNPLG FF |
| 32 | Acetaldehyde dehydrogenase from *Pseudomonas oleovorans*, protein | MTIPISLAKLNSSADTHSALEVFNLQKVASSARRGKFGIAERIA ALNLLKETIQRREPEIIAALAADFRKPASEVKLTEIFPVLQEINH AKRNLKDWMKPRRVRAALSVAGTRAGLRYEPKGVCLIIAPW NYPFNLSFGPLVSALAAGNSVVIKPSELTPHTATLIGSIVREAF SVDLVAVVEGDAAVSQELLALPFDHIFFTGSPRVGKLVMEAA SKTLASVTLELGGKSPTIIGPTANLPKAARNIVWGKFSNNGQT CIAPDHVFVHRCIAQKFNEILVKEIVRVYGKDFAAQRRSADYC RIVNDQHFNRINKLLTDAKAKGAKILQGGQVDATERLVVPTV LSNVTAAMDINHEEIFGPLLPIIEYDDIDSVIKRVNDGDKPLAL YVFSEDKQFVNNIVARTSSGSVGVNLSVVHFLHPNLPFGGVN NSGIGSAHGVYGFRAFSHEKPVLIDKFSITHWLFPPYTKKVKQ LIGITVKYLS |
| 33 | 3-oxoacyl-[acyl carrier protein] synthase 1, FabB, *Escherichia coli*, protein | MKRAVITGLGIVSSIGNNQQEVLASLREGRSGITFSQELKDSG MRSHVWGNVKLDTTGLIDRKVVRFMSDASIYAFLSMEQAIA DAGLSPEAYQNNPRVGLIAGSGGGSPRFQVFGADAMRGPRGL KAVGPYVVTKAMASGVSACLATPFKIHGVNYSISSACATSAH CIGNAVEQIQLGKQDIVFAGGGEELCWEMACEFDAMGALST KYNDTPEKASRTYDAHRDGFVIAGGGGMVVVEELEHALARG AHIYAEIVGYGATSDGADMVAPSGEGAVRCMKMAMHGVDT PIDYLNSHGTSTPVGDVKELAAIREVFGDKSPAISATKAMTGH SLGAAGVQEAIYSLLMLEHGFIAPSINIEELDEQAAGLNIVTET TDRELTTVMSNSFGFGGTNATLVMRKLKD |
| 34 | Acyl-[acyl carrier protein] reductase, AAR, *Synechococcus elongatus*, DNA sequence | ATGTTCGGTCTTATCGGTCATCTCACCAGTTTGGAGCAGGC CCGCGACGTTTCTCGCAGGATGGGCTACGACGAATACGCC GATCAAGGATTGGAGTTTTGGAGTAGCGCTCCTCCTCAAAT CGTTGATGAAATCACAGTCACCAGTGCCACAGGCAAGGTG ATTCACGGTCGCTACATCGAATCGTGTTTCTTGCCGGAAAT GCTGGCGGCGCGCCGCTTCAAAACAGCCACGCGCAAAGTT CTCAATGCCATGTCCCATGCCCAAAAACACGGCATCGACA TCTCGGCCTTGGGGGGCTTTACCTCGATTATTTTCGAGAAT TTCGATTTGGCCAGTTTGCGGCAAGTGCGCGACACTACCTT GGAGTTTGAACGGTTCACCACCGGCAATACTCACACGGCC TACGTAATCTGTAGACAGGTGGAAGCCGCTGCTAAAACGC TGGGCATCGACATTACCCAAGCGACAGTAGCGGTTGTCGG CGCGACTGGCGATATCGGTAGCGCTGTCTGCCGCTGGCTCG ACCTCAAACTGGGTGTCGGTGATTTGATCCTGACGGCGCGC AATCAGGAGCGTTTGGATAACCTGCAGGCTGAACTCGGCC GGGGCAAGATTCTGCCCTTGGAAGCCGCTCTGCCGGAAGC TGACTTTATCGTGTGGGTCGCCAGTATGCCTCAGGGCGTAG TGATCGACCCAGCAACCCTGAAGCAACCCTGCGTCCTAATC GACGGGGGCTACCCCAAAAACTTGGGCAGCAAAGTCCAAG GTGAGGGCATCTATGTCCTCAATGGCGGGGTAGTTGAACA TTGCTTCGACATCGACTGGCAGATCATGTCCGCTGCAGAGA TGGCGCGGCCCGAGCGCCAGATGTTTGCCTGCTTTGCCGAG GCGATGCTCTTGGAATTTGAAGGCTGGCATACTAACTTCTC CTGGGGCCGCAACCAAATCACGATCGAGAAGATGGAAGCG ATCGGTGAGGCATCGGTGCGCCACGGCTTCCAACCCTTGGC ATTGGCAATTTGA |

-continued

| Sequence Table | | |
|---|---|---|
| SEQ ID NO: | Description | Sequence |
| 35 | Acyl-[acyl carrier protein] reductase, AAR, *Synechococcus elongatus*, protein | MFGLIGHLTSLEQARDVSRRMGYDEYADQGLEFWSSAPPQIV DEITVTSATGKVIHGRYIESCFLPEMLAARRFKTATRKVLNAM SHAQKHGIDISALGGFTSIIFENFDLASLRQVRDTTLEFERFTTG NTHTAYVICRQVEAAAKTLGIDITQATVAVVGATGDIGSAVC RWLDLKLGVGDLILTARNQERLDNLQAELGRGKILPLEAALP EADFIVWVASMPQGVVIDPATLKQPCVLIDGGYPKNLGSKVQ GEGIYVLNGGVVEHCFDIDWQIMSAAEMARPERQMFACFAE AMLLEFEGWHTNFSWGRNQITIEKMEAIGEASVRHGFQPLALAI |

What is claimed is:

1. A recombinant proteobacterium, comprising:
   a heterologous acyl-ACP desaturase, wherein the heterologous acyl-ACP desaturase has at least 85% sequence identity to SEQ ID NO: 2 or SEQ ID NO: 12; and
   an acyl-ACP thioesterase, wherein the acyl-ACP thioesterase i) is native to the recombinant proteobacterium or ii) is heterologous to the recombinant proteobacterium and is a plant FatA-type thioesterase, a plant FatB-type thioesterase, or a bacterial acyl-ACP thioesterase;
   wherein expression of a native dual 3-hydroxy acyl-ACP dehydratase/isomerase is deleted or attenuated; and
   wherein the recombinant proteobacterium produces a non-native monounsaturated free fatty acid or a derivative thereof.

2. The recombinant proteobacterium of claim 1, wherein the heterologous acyl-ACP desaturase is a Δ9-tetradecanoyl-acyl-ACP desaturase.

3. The recombinant proteobacterium of claim 1, wherein the non-native monounsaturated free fatty acid or derivative thereof is an ω-3, ω-5, ω-6, ω-8, ω-9, ω-11, or ω-12 monounsaturated free fatty acid or derivative thereof.

4. The recombinant proteobacterium of claim 1, further comprising
   one or more of a ferredoxin, a ferredoxin reductase, or a flavodoxin reductase, wherein:
   one or more of the ferredoxin, ferredoxin reductase, or flavodoxin reductase is heterologous to the recombinant proteobacterium; or
   the recombinant proteobacterium overexpresses endogenous flavodoxin reductase or ferredoxin reductase.

5. The recombinant proteobacterium of claim 1, further comprising a heterologous 3-hydroxy acyl-ACP dehydratase.

6. The recombinant proteobacterium of claim 1, further comprising a heterologous dual 3-hydroxy acyl-ACP dehydratase/isomerase.

7. The recombinant proteobacterium of claim 1, further comprising one or more additional heterologous polypeptides selected from a ferredoxin, a ferredoxin reductase, a flavodoxin reductase, a 3-hydroxyacyl-ACP dehydratase, a dual 3-hydroxy acyl-ACP dehydratase/isomerase, a fatty acid metabolism regulator protein, a β-ketoacyl-ACP synthase, a carboxylic acid reductase, an alcohol dehydrogenase, a phosphopantetheinyl transferase, an alcohol acetyl-CoA transferase, an ω-hydroxylase, an alcohol oxidase/dehydrogenase, and an aldehyde dehydrogenase.

8. The recombinant proteobacterium of claim 1, wherein the recombinant proteobacterium produces a non-native monounsaturated free fatty acid or a derivative thereof that is a fatty alcohol, an ω-hydroxy fatty acid, a fatty alcohol acetate ester, a fatty aldehyde, or an α/ω-dicarboxylic acid.

9. The recombinant proteobacterium of claim 1, wherein the non-native monounsaturated free fatty acid is Z9-tetradecenoic acid, Z11-hexadecenoic acid, Z13-octadecenoic acid, or a combination thereof.

10. The recombinant proteobacterium of claim 1, wherein:
   (a) the recombinant proteobacterium comprises a carboxylic acid reductase, or comprises a carboxylic acid reductase and a phosphopantetheinyl transferase, wherein the recombinant proteobacterium produces a non-native monounsaturated fatty aldehyde or a non-native monounsaturated fatty alcohol;

(b) the recombinant proteobacterium comprises a carboxylic acid reductase and an alcohol dehydrogenase, or comprises a carboxylic acid reductase, an alcohol dehydrogenase, and a phosphopantetheinyl transferase, wherein the recombinant proteobacterium produces a non-native monounsaturated fatty alcohol;
   (c) the recombinant proteobacterium comprises a carboxylic acid reductase and an alcohol acetyl-CoA transferase, or comprises a carboxylic acid, an alcohol acetyl-CoA transferase, and a phosphopantetheinyl transferase, wherein the recombinant proteobacterium produces a non-native monounsaturated fatty alcohol acetate ester (FACE);
   (d) the recombinant proteobacterium comprises an ω-hydroxylase, wherein the recombinant proteobacterium produces a non-native monounsaturated ω-hydroxy fatty acid; or
   (e) the recombinant proteobacterium comprises an ω-hydroxylase, and further comprises an alcohol oxidase/dehydrogenase and an aldehyde dehydrogenase, wherein the recombinant proteobacterium produces a non-native monounsaturated α/ω-dicarboxylic acid.

11. The recombinant proteobacterium of claim 8, wherein:
   the non-native monounsaturated fatty aldehyde is Z9-tetradecenal, Z11-hexadecenal, Z13-octadecenal, or a combination thereof;
   the non-native monounsaturated fatty alcohol is Z9-tetradecenol, Z11-hexadecenol, Z13-octadecenol, or a combination thereof;
   the non-native monounsaturated fatty alcohol acetate ester (FACE) is Z9-tetradecenyl acetate, Z11-hexadecenyl acetate, Z13-octadecenyl acetate, or a combination thereof;
   the non-native monounsaturated ω-hydroxy fatty acid is (Z9)-14-hydroxy-tetradecenoic acid, (Z11)-16-hydroxy-hexadecenoic acid, (Z13)-18-hydroxy-octadecenoic acid, or a combination thereof; or
   the non-native monounsaturated α/ω-dicarboxylic acid is (Z5)-1,14-tetradecenedioic acid, (Z5)-1,16-hexadecenedioic acid, (Z5)-1,18-octadecenedioic acid, or a combination thereof.

12. The recombinant proteobacterium of claim 1, further comprising a carboxylic acid reductase, wherein the recombinant proteobacterium has one or more deletions in endogenous alcohol dehydrogenase genes, endogenous aldehyde reductase genes, or both.

13. A cell culture, comprising the recombinant proteobacterium of claim 1 and one or more non-native monounsaturated free fatty acids or derivatives thereof.

14. A method for producing a non-native monounsaturated free fatty acid or a derivative thereof, the method comprising culturing the recombinant proteobacterium of claim 1.

15. The method of claim 14, further comprising isolating the non-native monounsaturated free fatty acid or derivative thereof.

16. The method of claim 14, wherein:
   the non-native monounsaturated free fatty acid or derivative thereof is an ω-3, ω-5, ω-6, ω-8, ω-9, ω-11, or ω-12 monounsaturated free fatty acid or derivative thereof;
   the non-native monounsaturated free fatty acid or derivative thereof is a fatty acid, a fatty alcohol, ω-hydroxy fatty acid, a fatty alcohol acetate ester, a fatty aldehyde, or an α/ω-dicarboxylic acid; and the non-native monounsaturated free fatty acid or derivative thereof is an insect pheromone, an insect pheromone precursor, a fragrance, or a fragrance precursor.

17. The method of claim 14, wherein the recombinant proteobacterium further comprises one or more additional heterologous polypeptides selected from a ferredoxin, a ferredoxin reductase, a flavodoxin reductase, a 3-hydroxyacyl-ACP dehydratase, a dual 3-hydroxy acyl-ACP dehydratase/isomerase, a fatty acid metabolism regulator protein, a β-ketoacyl-ACP synthase, a carboxylic acid reductase, an alcohol dehydrogenase, a phosphopantetheinyl transferase, an alcohol acetyl-CoA transferase, an ω-hydroxylase, an alcohol oxidase/dehydrogenase, and an aldehyde dehydrogenase.

* * * * *

SEQUENCE LISTING

<160> NUMBER OF SEQ ID NOS: 35

<210> SEQ ID NO 1
<211> LENGTH: 1056
<212> TYPE: DNA
<213> ORGANISM: Pelargonium x hortorum

<400> SEQUENCE: 1

```
atggcttcta cctctatctc taaagttaac cacatccgta aagttggtgt taccggtgtt      60
atggctccgc agaaaatcga aatcttcaaa tctatggaag aatggggtaa acacaacatc     120
ctgccgctgg ctaaaccggt tgaaaaatct tggcagccga ccgacttcct gccggacccg     180
tcttctgaag gtttcatgga agaatacaac gctttcaaag aacgtacccg tgaactgccg     240
gacgaatact tcgttgttct ggctggtgac atgatcaccg aagaagctct gccgacctac     300
cagaccctgg ttaaccgtcc ggacgaagtt gctgacgaaa ccggtcactc tgaatctccg     360
tgggctgttt ggtctcgtgc ttggaccgct gaagaaaacc gtcacggtga cctgctgaac     420
aaatacctgt acctgtctgg taaactggac atgcgtcagg ttgaaaaaac catccagtac     480
ctgatcgctc tgggtcagga catcggtacc gaaaaaaacc cgtaccacct gttcatctac     540
acctctttcc aggaacgtgc taccttcatc tctcacgcta acaccgctaa actggctcag     600
cagcacggtg acaaacagct ggctcagatc tgcggtacca tcgctgctga cgaaaaacgt     660
cacgaaaccg cttacacccg tatcgttgac aaactgttcg aactggaccc ggacgaaacc     720
atgtcttgcc tggctcacat gatgaaacgt aaaatcacca tgccggctca cctgatgcgt     780
gacggtcgtg acccgcacct gttccagcac ttctctgtgg ttgcttctcg taccggtgtt     840
tacaccgtta tggactacat caacatcctg gaacacttcg ttgaaaaatg gaacatcgaa     900
aaaatcaccg ctggtctgtc tgacaaaggt cgtgaagctc aggactacgt tgcaaactg     960 ggtgaacgtc tgcgtaaagt tgaagaacgt gctcaccagc gtgttgttca ggctgacccg    1020
atcccgttct cttggatctt cgaccgtaaa gtttaa                              1056
```

<210> SEQ ID NO 2
<211> LENGTH: 351
<212> TYPE: PRT
<213> ORGANISM: Pelargonium x hortorum

<400> SEQUENCE: 2

```
Met Ala Ser Thr Ser Ile Ser Lys Val Asn His Ile Arg Lys Val Gly
1               5                   10                  15

Val Thr Gly Val Met Ala Pro Gln Lys Ile Glu Ile Phe Lys Ser Met
            20                  25                  30
```

```
Glu Glu Trp Gly Lys His Asn Ile Leu Pro Leu Ala Lys Pro Val Glu
        35              40              45
Lys Ser Trp Gln Pro Thr Asp Phe Leu Pro Asp Pro Ser Ser Glu Gly
        50              55              60
Phe Met Glu Glu Tyr Asn Ala Phe Lys Glu Arg Thr Arg Glu Leu Pro
65              70              75              80
Asp Glu Tyr Phe Val Val Leu Ala Gly Asp Met Ile Thr Glu Glu Ala
                85              90              95
Leu Pro Thr Tyr Gln Thr Leu Val Asn Arg Pro Asp Glu Val Ala Asp
            100             105             110
Glu Thr Gly His Ser Glu Ser Pro Trp Ala Val Trp Ser Arg Ala Trp
            115             120             125
Thr Ala Glu Glu Asn Arg His Gly Asp Leu Leu Asn Lys Tyr Leu Tyr
    130             135             140
Leu Ser Gly Lys Leu Asp Met Arg Gln Val Glu Lys Thr Ile Gln Tyr
145             150             155             160
Leu Ile Ala Leu Gly Gln Asp Ile Gly Thr Glu Lys Asn Pro Tyr His
                165             170             175
Leu Phe Ile Tyr Thr Ser Phe Gln Glu Arg Ala Thr Phe Ile Ser His
            180             185             190
Ala Asn Thr Ala Lys Leu Ala Gln Gln His Gly Asp Lys Gln Leu Ala
    195             200             205
Gln Ile Cys Gly Thr Ile Ala Ala Asp Glu Lys Arg His Glu Thr Ala
    210             215             220
Tyr Thr Arg Ile Val Asp Lys Leu Phe Glu Leu Asp Pro Asp Glu Thr
225             230             235             240
Met Ser Cys Leu Ala His Met Met Lys Arg Lys Ile Thr Met Pro Ala
                245             250             255
His Leu Met Arg Asp Gly Arg Asp Pro His Leu Phe Gln His Phe Ser
            260             265             270
Val Val Ala Ser Arg Thr Gly Val Tyr Thr Val Met Asp Tyr Ile Asn
    275             280             285
Ile Leu Glu His Phe Val Glu Lys Trp Asn Ile Glu Lys Ile Thr Ala
    290             295             300
Gly Leu Ser Asp Lys Gly Arg Glu Ala Gln Asp Tyr Val Cys Lys Leu
305             310             315             320
Gly Glu Arg Leu Arg Lys Val Glu Glu Arg Ala His Gln Arg Val Val
            325             330             335
Gln Ala Asp Pro Ile Pro Phe Ser Trp Ile Phe Asp Arg Lys Val
            340             345             350
```

<210> SEQ ID NO 3
<211> LENGTH: 921
<212> TYPE: DNA
<213> ORGANISM: Nostoc punctiforme

<400> SEQUENCE: 3

```
atgactcaag cgaaagccaa aaaagaccac ggtgacgttc ctgttaacac ttaccgtccc      60
aatgctccat ttattggcaa ggtaatatct aatgaaccat tagtcaaaga aggtggtatt     120
ggtattgttc aacaccttaa atttgaccta tctggtgggg atttgaagta tatagaaggt     180
caaagtattg cattattcc gccaggttta gacaagaacg gcaagcctga aaaactcaga     240
ctatattcca tcgcctcaac tcgtcatggt gatgatgtag atgataagac agtatcactg     300
tgcgtccgcc agttggagta caagcaccca gaaactggcg aaacagtcta cggtgtttgc     360
```

-continued

```
tctacgcacc tgtgtttcct caagccaggg gaagaggtaa aaattacagg gcctgtgggt        420
aaggaaatgt tgttacccaa tgaccctgat gctaatgtta tcatgatggc tactggaaca        480
ggtattgcgc cgatgcgggc ttacttgtgg cgtcagttta aagatgcgga aagagcggct        540
aacccagaat accaatttaa aggattctct tggctaatat tttggcgtacc tacaactcca        600 aacctttat ataaggaaga actggaagag attcaacaaa aatatcctga gaacttccgc          660
ctaactgctg ccatcagccg cgaacagaaa aatccccaag gcggtagaat gtatattcaa         720
gaccgcgtag cagaacatgc tgatgaattg tggcagttga ttaaaaatga aaaaacccac         780
acttacattt gcggttttgcg cggtatggaa gaaggtattg atgcagcctt aactgctgct        840
gctgctaagg aaggcgtaac ctggagtgat taccagaagc aactcaagaa agccggtcgc         900
tggcacgtag aaacttacta a                                                    921
```

```
<210> SEQ ID NO 4
<211> LENGTH: 306
<212> TYPE: PRT
<213> ORGANISM: Nostoc punctiforme

<400> SEQUENCE: 4

Met Thr Gln Ala Lys Ala Lys Lys Asp His Gly Asp Val Pro Val Asn
1               5                   10                  15

Thr Tyr Arg Pro Asn Ala Pro Phe Ile Gly Lys Val Ile Ser Asn Glu
                20                  25                  30

Pro Leu Val Lys Glu Gly Gly Ile Gly Ile Val Gln His Leu Lys Phe
            35                  40                  45

Asp Leu Ser Gly Gly Asp Leu Lys Tyr Ile Glu Gly Gln Ser Ile Gly
        50                  55                  60

Ile Ile Pro Pro Gly Leu Asp Lys Asn Gly Lys Pro Glu Lys Leu Arg
65                  70                  75                  80

Leu Tyr Ser Ile Ala Ser Thr Arg His Gly Asp Asp Val Asp Asp Lys
                85                  90                  95

Thr Val Ser Leu Cys Val Arg Gln Leu Glu Tyr Lys His Pro Glu Thr
            100                 105                 110

Gly Glu Thr Val Tyr Gly Val Cys Ser Thr His Leu Cys Phe Leu Lys
        115                 120                 125

Pro Gly Glu Glu Val Lys Ile Thr Gly Pro Val Gly Lys Glu Met Leu
        130                 135                 140

Leu Pro Asn Asp Pro Asp Ala Asn Val Ile Met Met Ala Thr Gly Thr
145                 150                 155                 160

Gly Ile Ala Pro Met Arg Ala Tyr Leu Trp Arg Gln Phe Lys Asp Ala
                165                 170                 175

Glu Arg Ala Ala Asn Pro Glu Tyr Gln Phe Lys Gly Phe Ser Trp Leu
            180                 185                 190

Ile Phe Gly Val Pro Thr Thr Pro Asn Leu Leu Tyr Lys Glu Glu Leu
        195                 200                 205

Glu Glu Ile Gln Gln Lys Tyr Pro Glu Asn Phe Arg Leu Thr Ala Ala
        210                 215                 220

Ile Ser Arg Glu Gln Lys Asn Pro Gln Gly Gly Arg Met Tyr Ile Gln
225                 230                 235                 240

Asp Arg Val Ala Glu His Ala Asp Glu Leu Trp Gln Leu Ile Lys Asn
                245                 250                 255

Glu Lys Thr His Thr Tyr Ile Cys Gly Leu Arg Gly Met Glu Glu Gly
            260                 265                 270
```

```
Ile Asp Ala Ala Leu Thr Ala Ala Ala Ala Lys Glu Gly Val Thr Trp
        275                 280                 285

Ser Asp Tyr Gln Lys Gln Leu Lys Lys Ala Gly Arg Trp His Val Glu
    290                 295                 300

Thr Tyr
305

<210> SEQ ID NO 5
<211> LENGTH: 300
<212> TYPE: DNA
<213> ORGANISM: Nostoc punctiforme

<400> SEQUENCE: 5
atgccaactt ataaagtgac actaattaac gaggctgaag ggctgaacac aacccttgat      60
gttgaggacg atacctatat tctagacgca gctgaagaag ctggtattga cctgccctac     120
tcttgccgcg ctggtgcttg ctctacttgt gcaggtaaac tcgtatcagg taccgtcgat     180
caaggcgatc aatcattctt agatgacgat caaatagaag ctggatatgt actgacctgt     240
gttgcttacc caacttctaa tgtcacgatc gaaactcaca agaagaaga actctattaa      300

<210> SEQ ID NO 6
<211> LENGTH: 99
<212> TYPE: PRT
<213> ORGANISM: Nostoc punctiforme

<400> SEQUENCE: 6

Met Pro Thr Tyr Lys Val Thr Leu Ile Asn Glu Ala Glu Gly Leu Asn
1               5                   10                  15

Thr Thr Leu Asp Val Glu Asp Asp Thr Tyr Ile Leu Asp Ala Ala Glu
            20                  25                  30

Glu Ala Gly Ile Asp Leu Pro Tyr Ser Cys Arg Ala Gly Ala Cys Ser
        35                  40                  45

Thr Cys Ala Gly Lys Leu Val Ser Gly Thr Val Asp Gln Gly Asp Gln
    50                  55                  60

Ser Phe Leu Asp Asp Asp Gln Ile Glu Ala Gly Tyr Val Leu Thr Cys
65                  70                  75                  80

Val Ala Tyr Pro Thr Ser Asn Val Thr Ile Glu Thr His Lys Glu Glu
                85                  90                  95

Glu Leu Tyr

<210> SEQ ID NO 7
<211> LENGTH: 939
<212> TYPE: DNA
<213> ORGANISM: Arabidopsis thaliana

<400> SEQUENCE: 7
atggctgttg tatctgctga tcaaggtagt gtggttcaag gtttggctac tctcgcggat      60
cagctccgat taggtagttt gactgaagat ggtttatctt ataaagagaa gtttgttgtt     120
agatcttacg aagtgggtag taacaaaacc gctactgttg aaaccattgc taatctttta     180
caggaggtgg gatgtaatca tgcacaaagt gttggttttt cgactgatgg gtttgcaaca     240
acaactacta tgaggaagtt gcatctcatt tgggttactg cgagaatgca tatcgagatc     300
tataagtacc ctgcttgggg tgatgtggtt gagatagaga cttggtgtca gagtgaagga     360
aggattggga caaggcgtga ttggattctt aaggattctg tcactggtga agtcactggc     420
cgtgctacaa gcaagtgggt gatgatgaac caagacacga cacggcttca gaaagtttct     480
```

-continued

```
gatgatgttc gggacgagta cttggtcttc tgtcctcaag aaccgaggtt agcatttccg      540
gaagagaata accgtagctt gaagaaaatc ccgaaactcg aagatccggc tcagtattca      600
atgattgggc ttaagcctag acgagctgat ctcgacatga accagcatgt caataatgtc      660
acctatattg gatgggttct ggagagcata ccacaagaaa ttgtagacac gcacgagctt      720
caggtcataa ctctggatta tagaagagaa tgtcaacaag acgatgtggt ggattcactc      780
accaccacca cctctgaaat tggtggaacc aatggctctg ccacgtctgg cacacagggc      840
cacaacgata gccagttctt gcacctcctg aggttgtctg agatggtca ggagatcaac       900 cgcgggacaa ctctgtggag aaagaagcct tcaagttaa                             939
```

```
<210> SEQ ID NO 8
<211> LENGTH: 312
<212> TYPE: PRT
<213> ORGANISM: Arabidopsis thaliana

<400> SEQUENCE: 8

Met Ala Val Val Ser Ala Asp Gln Gly Ser Val Val Gln Gly Leu Ala
1               5                   10                  15

Thr Leu Ala Asp Gln Leu Arg Leu Gly Ser Leu Thr Glu Asp Gly Leu
                20                  25                  30

Ser Tyr Lys Glu Lys Phe Val Val Arg Ser Tyr Glu Val Gly Ser Asn
            35                  40                  45

Lys Thr Ala Thr Val Glu Thr Ile Ala Asn Leu Leu Gln Glu Val Gly
        50                  55                  60

Cys Asn His Ala Gln Ser Val Gly Phe Ser Thr Asp Gly Phe Ala Thr
65                  70                  75                  80

Thr Thr Thr Met Arg Lys Leu His Leu Ile Trp Val Thr Ala Arg Met
                85                  90                  95

His Ile Glu Ile Tyr Lys Tyr Pro Ala Trp Gly Asp Val Val Glu Ile
                100                 105                 110

Glu Thr Trp Cys Gln Ser Glu Gly Arg Ile Gly Thr Arg Arg Asp Trp
            115                 120                 125

Ile Leu Lys Asp Ser Val Thr Gly Glu Val Thr Gly Arg Ala Thr Ser
        130                 135                 140

Lys Trp Val Met Met Asn Gln Asp Thr Arg Arg Leu Gln Lys Val Ser
145                 150                 155                 160

Asp Asp Val Arg Asp Glu Tyr Leu Val Phe Cys Pro Gln Glu Pro Arg
                165                 170                 175

Leu Ala Phe Pro Glu Glu Asn Asn Arg Ser Leu Lys Lys Ile Pro Lys
                180                 185                 190

Leu Glu Asp Pro Ala Gln Tyr Ser Met Ile Gly Leu Lys Pro Arg Arg
            195                 200                 205

Ala Asp Leu Asp Met Asn Gln His Val Asn Asn Val Thr Tyr Ile Gly
        210                 215                 220

Trp Val Leu Glu Ser Ile Pro Gln Glu Ile Val Asp Thr His Glu Leu
225                 230                 235                 240

Gln Val Ile Thr Leu Asp Tyr Arg Arg Glu Cys Gln Gln Asp Asp Val
                245                 250                 255

Val Asp Ser Leu Thr Thr Thr Thr Ser Glu Ile Gly Gly Thr Asn Gly
            260                 265                 270

Ser Ala Thr Ser Gly Thr Gln Gly His Asn Asp Ser Gln Phe Leu His
            275                 280                 285
```

```
Leu Leu Arg Leu Ser Gly Asp Gly Gln Glu Ile Asn Arg Gly Thr Thr
    290                 295                 300

Leu Trp Arg Lys Lys Pro Ser Ser
305                 310

<210> SEQ ID NO 9
<211> LENGTH: 762
<212> TYPE: DNA
<213> ORGANISM: Clostridium thermocellum

<400> SEQUENCE: 9
atgcagaaga aaagattttc aaagaagtat gaagtacatt actacgaaat caactcaatg      60
caggaagcaa ctcttctctc cctgctaaac tatatggagg actgcgcaat atcccactca     120
acctctgccg gatacggtgt caacgagtta ttggctgctg acgcaggatg ggtattatac     180
cgctggttaa ttaaaataga cagacttccc aagctcggag aaacaattac tgttcagaca     240
tgggcctctt ccttcgaacg cttctacggc aacagggaat ttatcgtatt ggacggcagg     300
gataacccca ttgtcaaagc ctcatccgta tggatatatt tcaatattaa aaaaagaaaa     360
cctatgagaa tccccctcga aatgggagat gcttatggca tagacgaaac aagagctttg     420
gaagaaccct ttaccgactt cgattttgat tttgaaccca agttattga agaatttact     480 gtaaaaagaa gtgatataga cacaaacagc cacgtaaaca acaagaaata cgttgactgg     540
attatggaaa ccgtacccca gcaaatatat gacaactaca aagttacatc tcttcagatt     600
atatacaaaa aggaatcttc tttgggttca ggcataaagg ccggatgtgt aattgatgag     660
caaaataccg ataatccgcg gctccttcac aaaatatggg acaagaatac cggtttggag     720
cttgtatccg ccgaaacaat ctggcaaaag attcagtcat aa                        762

<210> SEQ ID NO 10
<211> LENGTH: 240
<212> TYPE: PRT
<213> ORGANISM: Hungateiclostridium thermocellum

<400> SEQUENCE: 10

Met Gln Lys Lys Arg Phe Ser Lys Lys Tyr Glu Val His Tyr Tyr Glu
1               5                   10                  15

Ile Asn Ser Met Gln Glu Ala Thr Leu Leu Ser Leu Leu Asn Tyr Met
            20                  25                  30

Glu Asp Cys Ala Ile Ser His Ser Thr Ser Ala Gly Tyr Gly Val Asn
        35                  40                  45

Glu Leu Leu Ala Ala Asp Ala Gly Trp Val Leu Tyr Arg Trp Leu Ile
    50                  55                  60

Lys Ile Asp Arg Leu Pro Lys Leu Gly Glu Thr Ile Thr Val Gln Thr
65                  70                  75                  80

Trp Ala Ser Ser Phe Glu Arg Phe Tyr Gly Asn Arg Glu Phe Ile Val
                85                  90                  95

Leu Asp Gly Arg Asp Asn Pro Ile Val Lys Ala Ser Ser Val Trp Ile
            100                 105                 110

Tyr Phe Asn Ile Lys Lys Arg Lys Pro Met Arg Ile Pro Leu Glu Met
        115                 120                 125

Gly Asp Ala Tyr Gly Ile Asp Glu Thr Arg Ala Leu Glu Glu Pro Phe
        130                 135                 140

Thr Asp Phe Asp Phe Asp Phe Glu Pro Lys Val Ile Glu Glu Phe Thr
145                 150                 155                 160

Val Lys Arg Ser Asp Ile Asp Thr Asn Ser His Val Asn Asn Lys Lys
```

```
                    165              170              175
Tyr Val Asp Trp Ile Met Glu Thr Val Pro Gln Gln Ile Tyr Asp Asn
              180              185              190

Tyr Lys Val Thr Ser Leu Gln Ile Ile Tyr Lys Lys Glu Ser Ser Leu
              195              200              205

Gly Ser Gly Ile Lys Ala Gly Cys Val Ile Asp Glu Gln Asn Thr Asp
              210              215              220

Asn Pro Arg Leu Leu His Lys Ile Trp Asp Lys Asn Thr Gly Leu Glu
225              230              235              240

<210> SEQ ID NO 11
<211> LENGTH: 1089
<212> TYPE: DNA
<213> ORGANISM: Vitis vinifera

<400> SEQUENCE: 11
atggcttcca tgcaccgctc tgtgtccagg gagattaaga atacaaagaa gacttctagc      60
tctcctcgca aggtgcaagt aacccattca atgccaccac acaagattga gattttcaaa     120
tccatggaga attgggttga ggagaacgtt ttaattcacc tgaagccagt tgagaaatgt     180
tggcaacctc aggattttct gcctcatcct gcttctgatg gatttcatga gcgagtcgag     240
gagctaaagg agagagcaaa ggggatcccg gatgactact ttgtcgtttt ggttggagat     300
atgatcactg aagaagccct tccaacttac caaacactgt tcaataccac tgatggaatc     360
cgtgatgaaa caggtgcaag ccccacttct tgggcaactt ggacaagggc atggaccgct     420
gaagagaaca ggcacggtga ccttcttaat aagtatctct atctgtctgg aagagtagac     480
atgaaacaaa ttgagaagac gatccagtat ttgattaggg ctggaatgga tttccagacg     540
gaaaacaatc cgtacctttt attcatctat acttcatttc aagaaagggc aaccttcata     600
tcccatggca atactgccag gctcgccaag caacatgggg acaagagctt ggctcaaata     660
tgtggcataa tagcctcaga tgagaagcgc atgaaactg cctacaccaa gatagtggaa     720
aagctctttg agattgatcc caatgggact gtcttggctt ttgcagacag gatgaggaag     780
aaaatcacca tgccggccct cttgatgtat gatggatgtg atgacgacct ttttgaacac     840
ttctcagcag ttgctcagcg gcttggtgtg tatactgcca aggactatgt tgataactta     900
gaattctttg tggaaagatg gaatgtggaa aagctaactg gctttctag tgagggggcga     960 aaagctcagg attatgtttg tgggttagct aaaagattga gaacactgga ggagagagct    1020
caagaaaagg ctaagcaagc acccaccatt cctttcagtt ggattttttga tagagaagtg    1080 aagctctga                                                            1089

<210> SEQ ID NO 12
<211> LENGTH: 360
<212> TYPE: PRT
<213> ORGANISM: Vitis vinifera

<400> SEQUENCE: 12

Met Ala Ser Met His Arg Ser Val Ser Arg Glu Ile Lys Asn Thr Lys
1               5               10              15

Lys Thr Ser Ser Ser Pro Arg Lys Val Gln Val Thr His Ser Met Pro
              20              25              30

Pro His Lys Ile Glu Ile Phe Lys Ser Met Glu Asn Trp Val Glu Glu
         35              40              45

Asn Val Leu Ile His Leu Lys Pro Val Glu Lys Cys Trp Gln Pro Gln
    50              55              60
```

-continued

```
Asp Phe Leu Pro His Pro Ala Ser Asp Gly Phe His Glu Arg Val Glu
65                  70                  75                  80

Glu Leu Lys Glu Arg Ala Lys Gly Ile Pro Asp Asp Tyr Phe Val Val
                85                  90                  95

Leu Val Gly Asp Met Ile Thr Glu Glu Ala Leu Pro Thr Tyr Gln Thr
                100                 105                 110

Leu Phe Asn Thr Thr Asp Gly Ile Arg Asp Glu Thr Gly Ala Ser Pro
                115                 120                 125

Thr Ser Trp Ala Thr Trp Thr Arg Ala Trp Thr Ala Glu Glu Asn Arg
        130                 135                 140

His Gly Asp Leu Leu Asn Lys Tyr Leu Tyr Leu Ser Gly Arg Val Asp
145                 150                 155                 160

Met Lys Gln Ile Glu Lys Thr Ile Gln Tyr Leu Ile Arg Ala Gly Met
                165                 170                 175

Asp Phe Gln Thr Glu Asn Asn Pro Tyr Leu Leu Phe Ile Tyr Thr Ser
                180                 185                 190

Phe Gln Glu Arg Ala Thr Phe Ile Ser His Gly Asn Thr Ala Arg Leu
        195                 200                 205

Ala Lys Gln His Gly Asp Lys Ser Leu Ala Gln Ile Cys Gly Ile Ile
        210                 215                 220

Ala Ser Asp Glu Lys Arg His Glu Thr Ala Tyr Thr Lys Ile Val Glu
225                 230                 235                 240

Lys Leu Phe Glu Ile Asp Pro Asn Gly Thr Val Leu Ala Phe Ala Asp
                245                 250                 255

Arg Met Arg Lys Lys Ile Thr Met Pro Ala Leu Leu Met Tyr Asp Gly
        260                 265                 270

Cys Asp Asp Asp Leu Phe Glu His Phe Ser Ala Val Ala Gln Arg Leu
        275                 280                 285

Gly Val Tyr Thr Ala Lys Asp Tyr Val Asp Asn Leu Glu Phe Phe Val
        290                 295                 300

Glu Arg Trp Asn Val Glu Lys Leu Thr Gly Leu Ser Ser Glu Gly Arg
305                 310                 315                 320

Lys Ala Gln Asp Tyr Val Cys Gly Leu Ala Lys Arg Leu Arg Thr Leu
                325                 330                 335

Glu Glu Arg Ala Gln Glu Lys Ala Lys Gln Ala Pro Thr Ile Pro Phe
        340                 345                 350

Ser Trp Ile Phe Asp Arg Glu Val
        355                 360

<210> SEQ ID NO 13
<211> LENGTH: 747
<212> TYPE: DNA
<213> ORGANISM: Escherichia coli

<400> SEQUENCE: 13
atggctgatt gggtaacagg caaagtcact aaagtgcaga actggaccga cgccctgttt        60
agtctcaccg ttcacgcccc cgtgcttccg tttaccgccg ggcaatttac caagcttggc       120
cttgaaatcg acggcgaacg cgtccagcgc gcctactcct atgtaaactc gcccgataat       180
cccgatctgg agttttacct ggtcaccgtc cccgatggca aattaagccc acgactggcg       240
gcactgaaac aggcgatga agtgcaggtg gttagcgaag cggcaggatt ctttgtgctc        300
gatgaagtgc gcactgcga aacgctatgg atgctggcaa ccggtacagc gattggccct       360
tatttatcga ttctgcaact aggtaaagat ttagatcgct tcaaaaatct ggtcctggtg       420
```

-continued

```
cacgccgcac gttatgccgc cgacttaagc tatttgccac tgatgcagga actggaaaaa      480
cgctacgaag gaaaactgcg cattcagacg gtggtcagtc gggaaacggc agcggggtcg      540
ctcaccggac ggataccggc attaattgaa agtggggaac tggaaagcac gattggcctg      600
ccgatgaata aagaaccag ccatgtgatg ctgtgcggca atccacagat ggtgcgcgat        660
acacaacagt tgctgaaaga gacccggcag atgacgaaac atttacgtcg ccgaccgggc      720
catatgacag cggagcatta ctggtaa                                          747
```

```
<210> SEQ ID NO 14
<211> LENGTH: 247
<212> TYPE: PRT
<213> ORGANISM: Escherichia coli

<400> SEQUENCE: 14

Met Ala Asp Trp Val Thr Gly Lys Val Thr Lys Val Gln Asn Trp Thr
1                5                  10                  15

Asp Ala Leu Phe Ser Leu Thr Val His Ala Pro Val Leu Pro Phe Thr
                20                  25                  30

Ala Gly Gln Phe Thr Lys Leu Gly Leu Glu Ile Asp Gly Glu Arg Val
        35                  40                  45

Gln Arg Ala Tyr Ser Tyr Val Asn Ser Pro Asp Asn Pro Asp Leu Glu
    50                  55                  60

Phe Tyr Leu Val Thr Val Pro Asp Gly Lys Leu Ser Pro Arg Leu Ala
65                  70                  75                  80

Ala Leu Lys Pro Gly Asp Glu Val Gln Val Val Ser Glu Ala Ala Gly
                85                  90                  95

Phe Phe Val Leu Asp Glu Val Pro His Cys Glu Thr Leu Trp Met Leu
                100                 105                 110

Ala Thr Gly Thr Ala Ile Gly Pro Tyr Leu Ser Ile Leu Gln Leu Gly
        115                 120                 125

Lys Asp Leu Asp Arg Phe Lys Asn Leu Val Leu Val His Ala Ala Arg
    130                 135                 140

Tyr Ala Ala Asp Leu Ser Tyr Leu Pro Leu Met Gln Glu Leu Glu Lys
145                 150                 155                 160

Arg Tyr Glu Gly Lys Leu Arg Ile Gln Thr Val Val Ser Arg Glu Thr
                165                 170                 175

Ala Ala Gly Ser Leu Thr Gly Arg Ile Pro Ala Leu Ile Glu Ser Gly
        180                 185                 190

Glu Leu Glu Ser Thr Ile Gly Leu Pro Met Asn Lys Glu Thr Ser His
        195                 200                 205

Val Met Leu Cys Gly Asn Pro Gln Met Val Arg Asp Thr Gln Gln Leu
    210                 215                 220

Leu Lys Glu Thr Arg Gln Met Thr Lys His Leu Arg Arg Arg Pro Gly
225                 230                 235                 240

His Met Thr Ala Glu His Tyr
                245
```

```
<210> SEQ ID NO 15
<211> LENGTH: 488
<212> TYPE: DNA
<213> ORGANISM: Acinetobacter baylyi

<400> SEQUENCE: 15
atgatgactg agtcaaacac tcctgcgttt acgatccctg aattgccaat ggacattcaa      60
```

-continued

```
aaaattcgtg aatatttgcc acatcgctat ccattcctat tggttgatcg tgtagttgaa      120
gttggtgaaa ataatattgt tggctataaa aacgtttcga ttaacgaaga gtttttttcag      180 ggccatttto ctgattatco gattatgcca ggtgtcttga ttgtagaggc tttggcacaa      240
atttctggta ttttgggttt tattatgaat aatgaaactc ctaaaccagg ttctttgttt      300
ctgttcgcag gggctgagaa agttcgtttc aaaaaacaag tggttgctgg tgatcagctc      360
gttttaaaag ctgaacttgt catgcaaaaa cgtggtatct acaaatacaa ttgtactgct      420
acggttgatg gtaaagtcgc tacaaccgct gaaattatag tttcgcattt aagaacagag      480
caggcatg                                                              488
```

```
<210> SEQ ID NO 16
<211> LENGTH: 162
<212> TYPE: PRT
<213> ORGANISM: Acinetobacter baylyi

<400> SEQUENCE: 16

Met Met Thr Glu Ser Asn Thr Pro Ala Phe Thr Ile Pro Glu Leu Pro
1               5                   10                  15

Met Asp Ile Gln Lys Ile Arg Glu Tyr Leu Pro His Arg Tyr Pro Phe
            20                  25                  30

Leu Leu Val Asp Arg Val Val Glu Val Gly Glu Asn Asn Ile Val Gly
        35                  40                  45

Tyr Lys Asn Val Ser Ile Asn Glu Glu Phe Phe Gln Gly His Phe Pro
    50                  55                  60

Asp Tyr Pro Ile Met Pro Gly Val Leu Ile Val Glu Ala Leu Ala Gln
65                  70                  75                  80

Ile Ser Gly Ile Leu Gly Phe Ile Met Asn Asn Glu Thr Pro Lys Pro
                85                  90                  95

Gly Ser Leu Phe Leu Phe Ala Gly Ala Glu Lys Val Arg Phe Lys Lys
            100                 105                 110

Gln Val Val Ala Gly Asp Gln Leu Val Leu Lys Ala Glu Leu Val Met
            115                 120                 125

Gln Lys Arg Gly Ile Tyr Lys Tyr Asn Cys Thr Ala Thr Val Asp Gly
        130                 135                 140

Lys Val Ala Thr Thr Ala Glu Ile Ile Val Ser His Leu Arg Thr Glu
145                 150                 155                 160

Gln Ala
```

```
<210> SEQ ID NO 17
<211> LENGTH: 3525
<212> TYPE: DNA
<213> ORGANISM: Mycobacterium smegmatis

<400> SEQUENCE: 17
atgggcacga gcgatgttca cgacgcgacc gacggcgtta ccgagactgc actggatgat       60
gagcagagca ctcgtcgtat tgcagaactg tacgcaacgg acccagagtt cgcagcagca      120
gctcctctgc cggccgttgt cgatgcggcg cacaaaccgg gcctgcgtct ggcggaaatc      180
ctgcagaccc tgttcaccgg ctacggcgat cgtccggcgc tgggctatcg tgcacgtgag      240
ctggcgacgg acgaaggcgg tcgtacggtc acgcgtctgc tgccgcgctt cgataccctg      300
acctatgcac aggtgtggag ccgtgttcaa gcagtggctg cagcgttgcg tcacaatttc      360
gcacaaccga tttacccggg cgacgcggtc gcgactatcg ctttgcgag cccggactat      420 ttgacgctgg atctggtgtg cgcgtatctg ggcctggtca gcgttccttt gcagcataac      480
```

-continued

```
gctccggtgt ctcgcctggc cccgattctg gccgaggtgg aaccgcgtat tctgacggtg    540
agcgcagaat acctggacct ggcggttgaa tccgtccgtg atgtgaactc cgtcagccag    600
ctggttgttt tcgaccatca tccggaagtg gacgatcacc gtgacgcact ggctcgcgca    660
cgcgagcagc tggccggcaa aggtatcgca gttacgaccc tggatgcgat cgcagacgaa    720
ggcgcaggtt tgccggctga gccgatttac acggcggatc acgatcagcg tctggccatg    780
attctgtata ccagcggctc tacgggtgct ccgaaaggcg cgatgtacac cgaagcgatg    840
gtggctcgcc tgtggactat gagctttatc acgggcgacc cgaccccggt tatcaacgtg    900
aacttcatgc cgctgaacca tctgggcggt cgtatcccga ttagcaccgc cgtgcagaat    960
ggcggtacca gctacttcgt tccggaaagc gacatgagca cgctgtttga ggatctggcc    1020
ctggtccgcc ctaccgaact gggtctggtg ccgcgtgttg cggacatgct gtaccagcat    1080
catctggcga ccgtggatcg cctggtgacc cagggcgcgg acgaactgac tgcggaaaag    1140
caggccggtg cggaactgcg tgaacaggtc ttgggcggtc gtgttatcac cggttttgtt    1200
tccaccgcgc cgttggcggc agagatgcgt gcttttctgg atatcacctt gggtgcacac    1260
atcgttgacg gttacggtct gaccgaaacc ggtgcggtca cccgtgatgg tgtgattgtt    1320
cgtcctccgg tcattgatta caagctgatc gatgtgccgg agctgggtta cttctccacc    1380
gacaaaccgt acccgcgtgg cgagctgctg gttcgtagcc aaacgttgac tccgggttac    1440
tacaagcgcc cagaagtcac cgcgtccgtt ttcgatcgcg acggctatta ccacaccggc    1500
gacgtgatgg cagaaaccgc gccagaccac ctggtgtatg tggaccgccg caacaatgtt    1560
ctgaagctgg cgcaaggtga atttgtcgcc gtggctaacc tggaggccgt tttcagcggc    1620
gctgctctgg tccgccagat tttcgtgtat ggtaacagcg agcgcagctt tctgttggct    1680
gttgttgtcc ctaccccgga ggcgctggag caatacgacc ctgccgcatt gaaagcagcc    1740
ctggcggatt cgctgcagcg tacggcgcgt gatgccgagc tgcagagcta tgaagtgccg    1800
gcggacttca ttgttgagac tgagcctttt agcgctgcga acggtctgct gagcggtgtt    1860
ggcaagttgc tgcgtccgaa tttgaaggat cgctacggtc agcgtttgga gcagatgtac    1920
gcggacatcg cggctacgca ggcgaaccaa ttgcgtgaac tgcgccgtgc tgcggctact    1980
caaccggtga tcgacacgct gacgcaagct gcggcgacca tcctgggtac cggcagcgag    2040
gttgcaagcg acgcacactt tactgatttg ggcggtgatt ctctgagcgc gctgacgttg    2100
agcaacttgc tgtctgactt ctttggcttt gaagtcccgg ttggcacgat tgttaaccca    2160
gcgactaatc tggcacagct ggcgcaacat atcgaggcgc agcgcacggc gggtgaccgc    2220
cgtccatcct ttacgacggt ccacggtgcg gatgctacgg aaatccgtgc aagcgaactg    2280
actctggaca aattcatcga cgctgagact ctgcgcgcag cacctggttt gccgaaggtt    2340
acgactgagc cgcgtacggt cctgttgagc ggtgccaatg gttggttggg ccgcttcctg    2400
accctgcagt ggctggaacg tttggcaccg gttggcggta ccctgatcac cattgtgcgc    2460
ggtcgtgacg atgcagcggc acgtgcacgt ttgactcagg cttacgatac ggacccagag    2520
ctgtcccgcc gcttcgctga gttggcggat cgccacttgc gtgtggtggc aggtgatatc    2580
ggcgatccga atctgggcct gacccggag atttggcacc gtctggcagc agaggtcgat    2640
ctggtcgttc atccagcggc cctggtcaac cacgtcctgc cgtaccgcca gctgtttggt    2700
ccgaatgttg ttggcaccgc cgaagttatc aagttggctc tgaccgagcg catcaagcct    2760
gttacctacc tgtccacggt tagcgtcgcg atgggtattc ctgattttga ggaggacggt    2820
```

```
gacattcgta ccgtcagccc ggttcgtccg ctggatggtg gctatgcaaa tggctatggc      2880
aacagcaagt gggctggcga ggtgctgctg cgcgaggcac atgacctgtg tggcctgccg      2940
gttgcgacgt ttcgtagcga catgattctg gcccacccgc gctaccgtgg ccaagtgaat      3000
gtgccggaca tgttcacccg tctgctgctg tccctgctga tcacgggtgt ggcaccgcgt      3060
tccttctaca ttggtgatgg cgagcgtccg cgtgcacact acccgggcct gaccgtcgat      3120
tttgttgcgg aagcggttac taccctgggt gctcagcaac gtgagggtta tgtctcgtat      3180
gacgttatga atccgcacga tgacggtatt agcttggatg tctttgtgga ctggctgatt      3240
cgtgcgggcc acccaattga ccgtgttgac gactatgatg actgggtgcg tcgttttgaa      3300
accgcgttga ccgccttgcc ggagaaacgt cgtgcgcaga ccgttctgcc gctgctgcat      3360
gcctttcgcg cgccacaggc gccgttcgcgt ggcgcccctg aaccgaccga agtgtttcat      3420
gcagcggtgc gtaccgctaa agtcggtccg ggtgatattc cgcacctgga tgaagccctg      3480
atcgacaagt acatccgtga cctgcgcgag ttcggtctga tttag                       3525
```

<210> SEQ ID NO 18
<211> LENGTH: 1174
<212> TYPE: PRT
<213> ORGANISM: Mycobacterium smegmatis

<400> SEQUENCE: 18

```
Met Gly Thr Ser Asp Val His Asp Ala Thr Asp Gly Val Thr Glu Thr
1               5                   10                  15

Ala Leu Asp Asp Glu Gln Ser Thr Arg Arg Ile Ala Glu Leu Tyr Ala
            20                  25                  30

Thr Asp Pro Glu Phe Ala Ala Ala Ala Pro Leu Pro Ala Val Val Asp
        35                  40                  45

Ala Ala His Lys Pro Gly Leu Arg Leu Ala Glu Ile Leu Gln Thr Leu
    50                  55                  60

Phe Thr Gly Tyr Gly Asp Arg Pro Ala Leu Gly Tyr Arg Ala Arg Glu
65                  70                  75                  80

Leu Ala Thr Asp Glu Gly Gly Arg Thr Val Thr Arg Leu Leu Pro Arg
                85                  90                  95

Phe Asp Thr Leu Thr Tyr Ala Gln Val Trp Ser Arg Val Gln Ala Val
            100                 105                 110

Ala Ala Ala Leu Arg His Asn Phe Ala Gln Pro Ile Tyr Pro Gly Asp
        115                 120                 125

Ala Val Ala Thr Ile Gly Phe Ala Ser Pro Asp Tyr Leu Thr Leu Asp
    130                 135                 140

Leu Val Cys Ala Tyr Leu Gly Leu Val Ser Val Pro Leu Gln His Asn
145                 150                 155                 160

Ala Pro Val Ser Arg Leu Ala Pro Ile Leu Ala Glu Val Glu Pro Arg
                165                 170                 175

Ile Leu Thr Val Ser Ala Glu Tyr Leu Asp Leu Ala Val Glu Ser Val
            180                 185                 190

Arg Asp Val Asn Ser Val Ser Gln Leu Val Val Phe Asp His His Pro
        195                 200                 205

Glu Val Asp Asp His Arg Asp Ala Leu Ala Arg Ala Arg Glu Gln Leu
    210                 215                 220

Ala Gly Lys Gly Ile Ala Val Thr Thr Leu Asp Ala Ile Ala Asp Glu
225                 230                 235                 240

Gly Ala Gly Leu Pro Ala Glu Pro Ile Tyr Thr Ala Asp His Asp Gln
                245                 250                 255
```

-continued

```
Arg Leu Ala Met Ile Leu Tyr Thr Ser Gly Ser Thr Gly Ala Pro Lys
            260                 265                 270

Gly Ala Met Tyr Thr Glu Ala Met Val Ala Arg Leu Trp Thr Met Ser
            275                 280                 285

Phe Ile Thr Gly Asp Pro Thr Pro Val Ile Asn Val Asn Phe Met Pro
    290                 295                 300

Leu Asn His Leu Gly Gly Arg Ile Pro Ile Ser Thr Ala Val Gln Asn
305                 310                 315                 320

Gly Gly Thr Ser Tyr Phe Val Pro Glu Ser Asp Met Ser Thr Leu Phe
                325                 330                 335

Glu Asp Leu Ala Leu Val Arg Pro Thr Glu Leu Gly Leu Val Pro Arg
            340                 345                 350

Val Ala Asp Met Leu Tyr Gln His His Leu Ala Thr Val Asp Arg Leu
            355                 360                 365

Val Thr Gln Gly Ala Asp Glu Leu Thr Ala Glu Lys Gln Ala Gly Ala
    370                 375                 380

Glu Leu Arg Glu Gln Val Leu Gly Gly Arg Val Ile Thr Gly Phe Val
385                 390                 395                 400

Ser Thr Ala Pro Leu Ala Ala Glu Met Arg Ala Phe Leu Asp Ile Thr
                405                 410                 415

Leu Gly Ala His Ile Val Asp Gly Tyr Gly Leu Thr Glu Thr Gly Ala
            420                 425                 430

Val Thr Arg Asp Gly Val Ile Val Arg Pro Pro Val Ile Asp Tyr Lys
            435                 440                 445

Leu Ile Asp Val Pro Glu Leu Gly Tyr Phe Ser Thr Asp Lys Pro Tyr
    450                 455                 460

Pro Arg Gly Glu Leu Leu Val Arg Ser Gln Thr Leu Thr Pro Gly Tyr
465                 470                 475                 480

Tyr Lys Arg Pro Glu Val Thr Ala Ser Val Phe Asp Arg Asp Gly Tyr
                485                 490                 495

Tyr His Thr Gly Asp Val Met Ala Glu Thr Ala Pro Asp His Leu Val
            500                 505                 510

Tyr Val Asp Arg Arg Asn Asn Val Leu Lys Leu Ala Gln Gly Glu Phe
            515                 520                 525

Val Ala Val Ala Asn Leu Glu Ala Val Phe Ser Gly Ala Ala Leu Val
    530                 535                 540

Arg Gln Ile Phe Val Tyr Gly Asn Ser Glu Arg Ser Phe Leu Leu Ala
545                 550                 555                 560

Val Val Val Pro Thr Pro Glu Ala Leu Glu Gln Tyr Asp Pro Ala Ala
                565                 570                 575

Leu Lys Ala Ala Leu Ala Asp Ser Leu Gln Arg Thr Ala Arg Asp Ala
            580                 585                 590

Glu Leu Gln Ser Tyr Glu Val Pro Ala Asp Phe Ile Val Glu Thr Glu
            595                 600                 605

Pro Phe Ser Ala Ala Asn Gly Leu Leu Ser Gly Val Gly Lys Leu Leu
    610                 615                 620

Arg Pro Asn Leu Lys Asp Arg Tyr Gly Gln Arg Leu Glu Gln Met Tyr
625                 630                 635                 640

Ala Asp Ile Ala Ala Thr Gln Ala Asn Gln Leu Arg Glu Leu Arg Arg
                645                 650                 655

Ala Ala Ala Thr Gln Pro Val Ile Asp Thr Leu Thr Gln Ala Ala Ala
            660                 665                 670
```

-continued

```
Thr Ile Leu Gly Thr Gly Ser Glu Val Ala Ser Asp Ala His Phe Thr
        675             680             685

Asp Leu Gly Gly Asp Ser Leu Ser Ala Leu Thr Leu Ser Asn Leu Leu
        690             695             700

Ser Asp Phe Phe Gly Phe Glu Val Pro Val Gly Thr Ile Val Asn Pro
705             710             715             720

Ala Thr Asn Leu Ala Gln Leu Ala Gln His Ile Glu Ala Gln Arg Thr
            725             730             735

Ala Gly Asp Arg Arg Pro Ser Phe Thr Thr Val His Gly Ala Asp Ala
            740             745             750

Thr Glu Ile Arg Ala Ser Glu Leu Thr Leu Asp Lys Phe Ile Asp Ala
            755             760             765

Glu Thr Leu Arg Ala Ala Pro Gly Leu Pro Lys Val Thr Thr Glu Pro
        770             775             780

Arg Thr Val Leu Leu Ser Gly Ala Asn Gly Trp Leu Gly Arg Phe Leu
785             790             795             800

Thr Leu Gln Trp Leu Glu Arg Leu Ala Pro Val Gly Gly Thr Leu Ile
            805             810             815

Thr Ile Val Arg Gly Arg Asp Asp Ala Ala Ala Arg Ala Arg Leu Thr
            820             825             830

Gln Ala Tyr Asp Thr Asp Pro Glu Leu Ser Arg Arg Phe Ala Glu Leu
            835             840             845

Ala Asp Arg His Leu Arg Val Val Ala Gly Asp Ile Gly Asp Pro Asn
        850             855             860

Leu Gly Leu Thr Pro Glu Ile Trp His Arg Leu Ala Ala Glu Val Asp
865             870             875             880

Leu Val Val His Pro Ala Ala Leu Val Asn His Val Leu Pro Tyr Arg
            885             890             895

Gln Leu Phe Gly Pro Asn Val Val Gly Thr Ala Glu Val Ile Lys Leu
            900             905             910

Ala Leu Thr Glu Arg Ile Lys Pro Val Thr Tyr Leu Ser Thr Val Ser
            915             920             925

Val Ala Met Gly Ile Pro Asp Phe Glu Glu Asp Gly Asp Ile Arg Thr
        930             935             940

Val Ser Pro Val Arg Pro Leu Asp Gly Gly Tyr Ala Asn Gly Tyr Gly
945             950             955             960

Asn Ser Lys Trp Ala Gly Glu Val Leu Leu Arg Glu Ala His Asp Leu
            965             970             975

Cys Gly Leu Pro Val Ala Thr Phe Arg Ser Asp Met Ile Leu Ala His
            980             985             990

Pro Arg Tyr Arg Gly Gln Val Asn  Val Pro Asp Met Phe  Thr Arg Leu
        995             1000             1005

Leu Leu  Ser Leu Leu Ile Thr  Gly Val Ala Pro Arg  Ser Phe Tyr
    1010             1015             1020

Ile Gly  Asp Gly Glu Arg Pro  Arg Ala His Tyr Pro  Gly Leu Thr
    1025             1030             1035

Val Asp  Phe Val Ala Glu Ala  Val Thr Thr Leu Gly  Ala Gln Gln
    1040             1045             1050

Arg Glu  Gly Tyr Val Ser Tyr  Asp Val Met Asn Pro  His Asp Asp
    1055             1060             1065

Gly Ile  Ser Leu Asp Val Phe  Val Asp Trp Leu Ile  Arg Ala Gly
    1070             1075             1080

His Pro  Ile Asp Arg Val Asp  Asp Tyr Asp Asp Trp  Val Arg Arg
```

-continued

```
        1085              1090              1095

Phe Glu  Thr Ala Leu Thr Ala  Leu Pro Glu Lys Arg  Arg Ala Gln
    1100              1105              1110

Thr Val  Leu Pro Leu Leu His  Ala Phe Arg Ala Pro  Gln Ala Pro
    1115              1120              1125

Leu Arg  Gly Ala Pro Glu Pro  Thr Glu Val Phe His  Ala Ala Val
    1130              1135              1140

Arg Thr  Ala Lys Val Gly Pro  Gly Asp Ile Pro His  Leu Asp Glu
    1145              1150              1155

Ala Leu  Ile Asp Lys Tyr Ile  Arg Asp Leu Arg Glu  Phe Gly Leu
    1160              1165              1170

Ile
```

```
<210> SEQ ID NO 19
<211> LENGTH: 1026
<212> TYPE: DNA
<213> ORGANISM: Acinetobacter baylyi

<400> SEQUENCE: 19
atggcaacaa ctaatgtgat tcatgcttat gctgcaatgc aggcaggtga agcactcgtg     60
ccttattcgt ttgatgcagg cgaactgcaa ccacatcagg ttgaagttaa agtcgaatat    120
tgtgggctgt gccattccga tgtctcggta ctcaacaacg aatggcattc ttcggtttat    180
ccagtcgtgg caggtcatga agtgattggt acgattaccc aactgggaag tgaagccaaa    240
ggactaaaaa ttggtcaacg tgttggtatt ggctggacgg cagaaagctg tcaggcctgt    300
gaccaatgca tcagtggtca gcaggtattg tgcacgggcg aaaataccgc aactattatt    360
ggtcatgctg gtggctttgc agataaggtt cgtgcaggct ggcaatgggt cattcccctg    420
cccgacgaac tcgatccgac cagtgctggt cctttgctgt gtggcggaat cacagtattt    480
gatccaattt taaacatca gattcaggct attcatcatg ttgctgtgat tggtatcggt    540
ggtttgggac atatggccat caagctactt aaagcatggg gctgtgaaat tactgcgttt    600
agttcaaatc caaacaaaac cgatgagctc aaagctatgg gggccgatca cgtggtcaat    660
agccgtgatg atgccgaaat taaatcgcaa cagggtaaat ttgatttact gctgagtaca    720
gttaatgtgc ctttaaactg gaatgcgtat ctaaacacac tggcacccaa tggcactttc    780
cattttttgg gcgtggtgat ggaaccaatc cctgtacctg tcggtgcgct gctaggaggt    840
gccaaatcgc taacagcatc accaactggc tcgcctgctg ccttacgtaa gctgctcgaa    900
tttgcggcac gtaagaatat cgcacctcaa atcgagatga tcctatgtc ggagctgaat    960 gaggccatcg aacgcttaca ttcgggtcaa gcacgttatc ggattgtact taaagccgat   1020
ttttaa                                                             1026
```

```
<210> SEQ ID NO 20
<211> LENGTH: 341
<212> TYPE: PRT
<213> ORGANISM: Acinetobacter baylyi

<400> SEQUENCE: 20

Met Ala Thr Thr Asn Val Ile His Ala Tyr Ala Ala Met Gln Ala Gly
1               5                   10                  15

Glu Ala Leu Val Pro Tyr Ser Phe Asp Ala Gly Glu Leu Gln Pro His
            20                  25                  30

Gln Val Glu Val Lys Val Glu Tyr Cys Gly Leu Cys His Ser Asp Val
        35                  40                  45
```

```
Ser Val Leu Asn Asn Glu Trp His Ser Ser Val Tyr Pro Val Val Ala
    50                  55              60

Gly His Glu Val Ile Gly Thr Ile Thr Gln Leu Gly Ser Glu Ala Lys
65                  70                  75                  80

Gly Leu Lys Ile Gly Gln Arg Val Gly Ile Gly Trp Thr Ala Glu Ser
                85                  90                  95

Cys Gln Ala Cys Asp Gln Cys Ile Ser Gly Gln Gln Val Leu Cys Thr
                100                 105                 110

Gly Glu Asn Thr Ala Thr Ile Ile Gly His Ala Gly Gly Phe Ala Asp
            115                 120                 125

Lys Val Arg Ala Gly Trp Gln Trp Val Ile Pro Leu Pro Asp Glu Leu
    130                 135                 140

Asp Pro Thr Ser Ala Gly Pro Leu Leu Cys Gly Gly Ile Thr Val Phe
145                 150                 155                 160

Asp Pro Ile Leu Lys His Gln Ile Gln Ala Ile His His Val Ala Val
            165                 170                 175

Ile Gly Ile Gly Gly Leu Gly His Met Ala Ile Lys Leu Leu Lys Ala
            180                 185                 190

Trp Gly Cys Glu Ile Thr Ala Phe Ser Ser Asn Pro Asn Lys Thr Asp
    195                 200                 205

Glu Leu Lys Ala Met Gly Ala Asp His Val Val Asn Ser Arg Asp Asp
    210                 215                 220

Ala Glu Ile Lys Ser Gln Gln Gly Lys Phe Asp Leu Leu Leu Ser Thr
225                 230                 235                 240

Val Asn Val Pro Leu Asn Trp Asn Ala Tyr Leu Asn Thr Leu Ala Pro
            245                 250                 255

Asn Gly Thr Phe His Phe Leu Gly Val Val Met Glu Pro Ile Pro Val
            260                 265                 270

Pro Val Gly Ala Leu Leu Gly Gly Ala Lys Ser Leu Thr Ala Ser Pro
            275                 280                 285

Thr Gly Ser Pro Ala Ala Leu Arg Lys Leu Leu Glu Phe Ala Ala Arg
    290                 295                 300

Lys Asn Ile Ala Pro Gln Ile Glu Met Tyr Pro Met Ser Glu Leu Asn
305                 310                 315                 320

Glu Ala Ile Glu Arg Leu His Ser Gly Gln Ala Arg Tyr Arg Ile Val
            325                 330                 335

Leu Lys Ala Asp Phe
            340
```

<210> SEQ ID NO 21
<211> LENGTH: 2400
<212> TYPE: DNA
<213> ORGANISM: Artificial Sequence
<220> FEATURE:
<223> OTHER INFORMATION: Hybrid fusion cytochrome P450 Cyp153A16 (G307A)

<400> SEQUENCE: 21

```
atgccaacac tgcccagaac atttgacgac attcagtccc gactgattaa cgccacctcc      60
agggtggtgc cgatgcagag gcaaattcag ggactgaaat cttaatgag cgccaagagg      120 aagaccttcg gcccacgccg accgatgccc gaattcgttg aaacacccat cccggacgtt      180
aacacgctgg cccttgagga catcgatgtc agcaatccgt ttttataccg gcagggtcag      240
tggcgcgcct atttcaaacg gttgcgtgat gaggcgccgg tccattacca gaagaacagc      300
cctttcggcc ccttctggtc ggtaactcgg tttgaagaca tcctgttcgt ggataagagt      360
```

-continued

```
cacgacctgt tttccgccga gccgcaaatc attctcggtg accctccgga ggggctgtcg      420
gtggaaatgt tcatagcgat ggatccgccg aaacacgatg tgcagcgcag ctcggtgcag      480
ggagtagtgg caccgaaaaa cctgaaggag atggaggggc tgatccgatc acgcaccggc      540
gatgtgcttg acagcctgcc tacagacaaa ccctttaact gggtacctgc tgtttccaag      600
gaactcacag gccgcatgct ggcgacgctt ctggattttc cttacgagga acgccacaag      660
ctggttgagt ggtcggacag aatggcaggt gcagcatcgg ccaccggcgg ggagtttgcc      720
gatgaaaatg ccatgtttga cgacgcggca gacatggccc ggtctttctc caggctttgg      780
cgggacaagg aggcgcgccg cgcagcaggc gaggagcccg gtttcgattt gatcagcctg      840
ttgcagagca acaaagaaac gaaagacctg atcaatcggc cgatggagtt tatcggtaat      900
ttgacgctgc tcatagtcgc cggcaacgat acgacgcgca actcgatgag tggtggcctg      960
gtggccatga acgaattccc cagggaattt gaaaaattga aggcaaaacc ggagttgatt     1020
ccgaacatgt tgtcggaaat catccgctgg caaacgccgc tggcctatat cgcgccgaatc     1080 gccaagcagg atgtcgaact gggcggccag accatcaaga agggtgatcg agttgtcatg     1140
tggtacgcgt cgggtaaccg ggacgagcgc aaatttgaca accccgatca gttcatcatt     1200
gatcgcaagg acgcacgaaa ccacatgtcg ttcggctatg gggttcaccg ttgcatgggc     1260
aaccgtctgg ctgaactgca actgcgcatc ctctgggaag aaatactcaa gcgttttgac     1320
aacatcgaag tcgtcgaaga gcccgagcgg gtgcagtcca acttcgtgcg gggctattcc     1380
aggttgatgg tcaaactgac accgaacagt gtactccatc gtcatcaacc tgtcaccatc     1440
ggcgagccgg ccgctcgtgc tgtgagccgc acggtgaccg ttgagcgtct tgatcgcatt     1500
gccgacgatg tccttcgcct ggtccttcgc gatgctggag gtaaaaccct cccgacgtgg     1560
acgcctggcg ctcacatcga cctggatctg ggtgctctga gccgtcagta ttcgctctgc     1620
ggcgctccgg atgctccgtc gtacgaaatc gccgtgcact agatccggaa aagccgtggt     1680
ggaagccgct atattcatga acagctggaa gttggaagtc cgctgcgtat gcgtggccca     1740
cgcaaccatt tcgccctgga tccgggtgcg aacattacg tgtttgttgc cggggggtatc     1800 ggcatcacgc cggtgctggc aatggcggat catgcccgtg cgcgtggttg gtcgtacgaa     1860
ctgcattatt gtggtcgtaa tcgtagcggt atggcttacc tggaacgcgt cgcgggacat     1920
ggtgaccgcg ctgccttgca cgtatctgaa gaaggcaccc gcattgatct ggcggcatta     1980
cttgctgaac cggcgccggg cgtgcaaatc tacgcctgcg tccgggccg tttattagcg     2040 ggtcttgaag acgcgtctcg taattggccg gatggcgcgc ttcatgtgga gcatttcact     2100
tcgagtttag ccgctttgga tccggatgtc gaacatgcct ttgatttgga gctgcgtgac     2160
tctggcctta ccgttcgcgt cgagccaact cagaccgttt tagacgcttt gcgtgcgaac     2220
aatatcgacg tcccgtcgga ttgcgaagag gggctgtgtg gttcttgcga agtagccgtt     2280
ctggatggcg aggttgatca ccgtgatacc gttctgacta aggccgagcg cgccgcgaat     2340
cgtcagatga tgacttgctg cagtcgtgca tgcggtgatc gtctggcgct gcgcctctaa     2400
```

<210> SEQ ID NO 22
<211> LENGTH: 799
<212> TYPE: PRT
<213> ORGANISM: Artificial Sequence
<220> FEATURE:
<223> OTHER INFORMATION: Hybrid fusion cytochrome P450 Cyp153A16(G307A)

<400> SEQUENCE: 22

-continued

```
Met Pro Thr Leu Pro Arg Thr Phe Asp Asp Ile Gln Ser Arg Leu Ile
1               5                   10                  15

Asn Ala Thr Ser Arg Val Val Pro Met Gln Arg Gln Ile Gln Gly Leu
            20                  25                  30

Lys Phe Leu Met Ser Ala Lys Arg Lys Thr Phe Gly Pro Arg Arg Pro
        35                  40                  45

Met Pro Glu Phe Val Glu Thr Pro Ile Pro Asp Val Asn Thr Leu Ala
    50                  55                  60

Leu Glu Asp Ile Asp Val Ser Asn Pro Phe Leu Tyr Arg Gln Gly Gln
65                  70                  75                  80

Trp Arg Ala Tyr Phe Lys Arg Leu Arg Asp Glu Ala Pro Val His Tyr
                85                  90                  95

Gln Lys Asn Ser Pro Phe Gly Pro Phe Trp Ser Val Thr Arg Phe Glu
            100                 105                 110

Asp Ile Leu Phe Val Asp Lys Ser His Asp Leu Phe Ser Ala Glu Pro
        115                 120                 125

Gln Ile Ile Leu Gly Asp Pro Pro Glu Gly Leu Ser Val Glu Met Phe
        130                 135                 140

Ile Ala Met Asp Pro Pro Lys His Asp Val Gln Arg Ser Ser Val Gln
145                 150                 155                 160

Gly Val Val Ala Pro Lys Asn Leu Lys Glu Met Glu Gly Leu Ile Arg
                165                 170                 175

Ser Arg Thr Gly Asp Val Leu Asp Ser Leu Pro Thr Asp Lys Pro Phe
                180                 185                 190

Asn Trp Val Pro Ala Val Ser Lys Glu Leu Thr Gly Arg Met Leu Ala
            195                 200                 205

Thr Leu Leu Asp Phe Pro Tyr Glu Glu Arg His Lys Leu Val Glu Trp
    210                 215                 220

Ser Asp Arg Met Ala Gly Ala Ala Ser Ala Thr Gly Gly Glu Phe Ala
225                 230                 235                 240

Asp Glu Asn Ala Met Phe Asp Asp Ala Ala Asp Met Ala Arg Ser Phe
                245                 250                 255

Ser Arg Leu Trp Arg Asp Lys Glu Ala Arg Arg Ala Ala Gly Glu Glu
            260                 265                 270

Pro Gly Phe Asp Leu Ile Ser Leu Leu Gln Ser Asn Lys Glu Thr Lys
        275                 280                 285

Asp Leu Ile Asn Arg Pro Met Glu Phe Ile Gly Asn Leu Thr Leu Leu
    290                 295                 300

Ile Val Ala Gly Asn Asp Thr Thr Arg Asn Ser Met Ser Gly Gly Leu
305                 310                 315                 320

Val Ala Met Asn Glu Phe Pro Arg Glu Phe Glu Lys Leu Lys Ala Lys
                325                 330                 335

Pro Glu Leu Ile Pro Asn Met Val Ser Glu Ile Ile Arg Trp Gln Thr
            340                 345                 350

Pro Leu Ala Tyr Met Arg Arg Ile Ala Lys Gln Asp Val Glu Leu Gly
        355                 360                 365

Gly Gln Thr Ile Lys Lys Gly Asp Arg Val Val Met Trp Tyr Ala Ser
    370                 375                 380

Gly Asn Arg Asp Glu Arg Lys Phe Asp Asn Pro Asp Gln Phe Ile Ile
385                 390                 395                 400

Asp Arg Lys Asp Ala Arg Asn His Met Ser Phe Gly Tyr Gly Val His
            405                 410                 415

Arg Cys Met Gly Asn Arg Leu Ala Glu Leu Gln Leu Arg Ile Leu Trp
```

```
                420             425             430

Glu Glu Ile Leu Lys Arg Phe Asp Asn Ile Glu Val Val Glu Glu Pro
            435             440             445

Glu Arg Val Gln Ser Asn Phe Val Arg Gly Tyr Ser Arg Leu Met Val
        450             455             460

Lys Leu Thr Pro Asn Ser Val Leu His Arg His Gln Pro Val Thr Ile
465             470             475             480

Gly Glu Pro Ala Ala Arg Ala Val Ser Arg Thr Val Thr Val Glu Arg
            485             490             495

Leu Asp Arg Ile Ala Asp Asp Val Leu Arg Leu Val Leu Arg Asp Ala
            500             505             510

Gly Gly Lys Thr Leu Pro Thr Trp Thr Pro Gly Ala His Ile Asp Leu
            515             520             525

Asp Leu Gly Ala Leu Ser Arg Gln Tyr Ser Leu Cys Gly Ala Pro Asp
        530             535             540

Ala Pro Ser Tyr Glu Ile Ala Val His Leu Asp Pro Glu Ser Arg Gly
545             550             555             560

Gly Ser Arg Tyr Ile His Glu Gln Leu Glu Val Gly Ser Pro Leu Arg
            565             570             575

Met Arg Gly Pro Arg Asn His Phe Ala Leu Asp Pro Gly Ala Glu His
            580             585             590

Tyr Val Phe Val Ala Gly Gly Ile Gly Ile Thr Pro Val Leu Ala Met
            595             600             605

Ala Asp His Ala Arg Ala Arg Gly Trp Ser Tyr Glu Leu His Tyr Cys
        610             615             620

Gly Arg Asn Arg Ser Gly Met Ala Tyr Leu Glu Arg Val Ala Gly His
625             630             635             640

Gly Asp Arg Ala Ala Leu His Val Ser Glu Glu Gly Thr Arg Ile Asp
            645             650             655

Leu Ala Ala Leu Leu Ala Glu Pro Ala Pro Gly Val Gln Ile Tyr Ala
            660             665             670

Cys Gly Pro Gly Arg Leu Leu Ala Gly Leu Glu Asp Ala Ser Arg Asn
            675             680             685

Trp Pro Asp Gly Ala Leu His Val Glu His Phe Thr Ser Ser Leu Ala
        690             695             700

Ala Leu Asp Pro Asp Val Glu His Ala Phe Asp Leu Glu Leu Arg Asp
705             710             715             720

Ser Gly Leu Thr Val Arg Val Glu Pro Thr Gln Thr Val Leu Asp Ala
            725             730             735

Leu Arg Ala Asn Asn Ile Asp Val Pro Ser Asp Cys Glu Glu Gly Leu
            740             745             750

Cys Gly Ser Cys Glu Val Ala Val Leu Asp Gly Glu Val Asp His Arg
            755             760             765

Asp Thr Val Leu Thr Lys Ala Glu Arg Ala Ala Asn Arg Gln Met Met
        770             775             780

Thr Cys Cys Ser Arg Ala Cys Gly Asp Arg Leu Ala Leu Arg Leu
785             790             795
```

<210> SEQ ID NO 23
<211> LENGTH: 1578
<212> TYPE: DNA
<213> ORGANISM: Saccharomyces cerevisiae

<400> SEQUENCE: 23

-continued

```
atgaacgaaa tcgacgaaaa aaaccaggct ccggttcacc aggaatgcct gaaagaaatg          60
atccagaacg gtcacgctcg tcgtatgggt tctgttgaag acctgtacgt tgctctgaac         120
cgtcagaacc tgtaccgtaa cttctgcacc tacggtgaac tgtctgacta ctgcacccgt         180
gaccagctga ccctggctct gcgtgaaatc tgcctgaaaa acccgacccct gctgcacatc        240 gttctgccga cccgttggcc gaaccacgaa aactactacc gttcttctga atactactct         300
cgtccgcacc cggttcacga ctacatctct gttctgcagg aactgaaact gtctggtgtt         360
gttctgaacg aacagccgga atactctgct gttatgaaac agatcctgga agaattcaaa         420
aactctaaag ttcttacac cgctaaaatc ttcaaactga ccaccaccct gaccatcccg          480
tacttcggtc cgaccggtcc gtcttggcgt ctgatctgcc tgccggaaga acacaccgaa         540
aaatggaaaa aattcatctt cgtttctaac cactgcatgt ctgacggtcg ttcttctatc         600
cacttcttcc acgacctgcg tgacgaactg aacaacatca aaaccccgcc gaaaaaactg         660
gactacatct tcaaatacga agaagactac cagctgctgc gtaaactgcc ggaaccgatc         720
gaaaaagtta tcgacttccg tccgccgtac ctgttcatcc cgaaatctct gctgtctggt         780
ttcatctaca ccaccctgcg tttctcttct aaaggtgttt gcatgcgtat ggacgacgtt         840
gaaaaaaccg acgacgttgt taccgaaatc atcaacatct ctccgaccga attccaggct        900
atcaaagcta acatcaaatc taacatccag ggtaaatgca ccatcacccc gttcctgcac         960
gtttgctggt tcgtttctct gcacaaatgg ggtaaattct tcaaaccgct gaacttcgaa       1020
tggctgaccg acatcttcat cccggctgac tgccgttctc agctgccgga cgacgacgaa       1080
atgcgtcaga tgtaccgtta cggtgctaac gttggtttca tcgacttcac cccgtggatc       1140
tctgaattcg acatgaacga caacaaagaa aacttctggc cgctgatcga acactaccac       1200
gaagttatct ctgaagctct gcgtaacaaa aaacacctgc acggtctggg tttcaacatc       1260
cagggtttcg ttcagaaata cgttaacatc gacaaagtta tgtgcgaccg tgctatcggt       1320
aaacgtcgtg gtggtaccct gctgtctaac gttggtctgt tcaaccagct ggaagaaccg       1380
gacgctaaat actctatctg cgacctggct ttcggtcagt ccagggttc ttggcaccag        1440 gctttctctc tgggtgtttg ctctaccaac gttaaaggta tgaacatcgt tgttgcttct       1500
accaaaaacg ttgttggttc tcaggaatct ctggaagaac tgtgctctat ctacaaagct       1560
ctgctgctgg gtccgtag                                                     1578
```

<210> SEQ ID NO 24
<211> LENGTH: 525
<212> TYPE: PRT
<213> ORGANISM: Saccharomyces cerevisiae

<400> SEQUENCE: 24

```
Met Asn Glu Ile Asp Glu Lys Asn Gln Ala Pro Val His Gln Glu Cys
1               5                   10                  15

Leu Lys Glu Met Ile Gln Asn Gly His Ala Arg Arg Met Gly Ser Val
            20                  25                  30

Glu Asp Leu Tyr Val Ala Leu Asn Arg Gln Asn Leu Tyr Arg Asn Phe
        35                  40                  45

Cys Thr Tyr Gly Glu Leu Ser Asp Tyr Cys Thr Arg Asp Gln Leu Thr
    50                  55                  60

Leu Ala Leu Arg Glu Ile Cys Leu Lys Asn Pro Thr Leu Leu His Ile
65                  70                  75                  80

Val Leu Pro Thr Arg Trp Pro Asn His Glu Asn Tyr Tyr Arg Ser Ser
                85                  90                  95
```

-continued

```
Glu Tyr Tyr Ser Arg Pro His Pro Val His Asp Tyr Ile Ser Val Leu
            100                 105                 110

Gln Glu Leu Lys Leu Ser Gly Val Val Leu Asn Glu Gln Pro Glu Tyr
            115                 120                 125

Ser Ala Val Met Lys Gln Ile Leu Glu Glu Phe Lys Asn Ser Lys Gly
            130                 135                 140

Ser Tyr Thr Ala Lys Ile Phe Lys Leu Thr Thr Thr Leu Thr Ile Pro
145                 150                 155                 160

Tyr Phe Gly Pro Thr Gly Pro Ser Trp Arg Leu Ile Cys Leu Pro Glu
                165                 170                 175

Glu His Thr Glu Lys Trp Lys Lys Phe Ile Phe Val Ser Asn His Cys
            180                 185                 190

Met Ser Asp Gly Arg Ser Ser Ile His Phe Phe His Asp Leu Arg Asp
            195                 200                 205

Glu Leu Asn Asn Ile Lys Thr Pro Pro Lys Lys Leu Asp Tyr Ile Phe
            210                 215                 220

Lys Tyr Glu Glu Asp Tyr Gln Leu Leu Arg Lys Leu Pro Glu Pro Ile
225                 230                 235                 240

Glu Lys Val Ile Asp Phe Arg Pro Pro Tyr Leu Phe Ile Pro Lys Ser
                245                 250                 255

Leu Leu Ser Gly Phe Ile Tyr Asn His Leu Arg Phe Ser Ser Lys Gly
                260                 265                 270

Val Cys Met Arg Met Asp Asp Val Glu Lys Thr Asp Asp Val Val Thr
            275                 280                 285

Glu Ile Ile Asn Ile Ser Pro Thr Glu Phe Gln Ala Ile Lys Ala Asn
            290                 295                 300

Ile Lys Ser Asn Ile Gln Gly Lys Cys Thr Ile Thr Pro Phe Leu His
305                 310                 315                 320

Val Cys Trp Phe Val Ser Leu His Lys Trp Gly Lys Phe Phe Lys Pro
                325                 330                 335

Leu Asn Phe Glu Trp Leu Thr Asp Ile Phe Ile Pro Ala Asp Cys Arg
                340                 345                 350

Ser Gln Leu Pro Asp Asp Asp Glu Met Arg Gln Met Tyr Arg Tyr Gly
            355                 360                 365

Ala Asn Val Gly Phe Ile Asp Phe Thr Pro Trp Ile Ser Glu Phe Asp
            370                 375                 380

Met Asn Asp Asn Lys Glu Asn Phe Trp Pro Leu Ile Glu His Tyr His
385                 390                 395                 400

Glu Val Ile Ser Glu Ala Leu Arg Asn Lys Lys His Leu His Gly Leu
                405                 410                 415

Gly Phe Asn Ile Gln Gly Phe Val Gln Lys Tyr Val Asn Ile Asp Lys
                420                 425                 430

Val Met Cys Asp Arg Ala Ile Gly Lys Arg Arg Gly Gly Thr Leu Leu
            435                 440                 445

Ser Asn Val Gly Leu Phe Asn Gln Leu Glu Glu Pro Asp Ala Lys Tyr
            450                 455                 460

Ser Ile Cys Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
                485                 490                 495

Val Val Ala Ser Thr Lys Asn Val Val Gly Ser Gln Glu Ser Leu Glu
            500                 505                 510
```

-continued

```
Glu Leu Cys Ser Ile Tyr Lys Ala Leu Leu Leu Gly Pro
    515                 520                 525

<210> SEQ ID NO 25
<211> LENGTH: 621
<212> TYPE: DNA
<213> ORGANISM: Escherichia coli

<400> SEQUENCE: 25
atgaaaacta cgcatacctc cctcccettt gccggacata cgctgcattt tgttgagttc      60
gatccggcga attttttgtga gcaggattta ctctggctgc cgcactacgc acaactgcaa     120
cacgctggac gtaaacgtaa aacagagcat ttagccggac ggatcgctgc tgtttatgct     180
ttgcgggaat atggctataa atgtgtgccc gcaatcggcg agctacgcca acctgtctgg     240
cctgcggagg tatacggcag tattagccac tgtgggacta cggcattagc cgtggtatct     300
cgtcaaccga ttggcattga tatagaagaa atttttttctg tacaaaccgc aagagaattg     360
acagacaaca ttattacacc agcggaacac gagcgactcg cagactgcgg tttagccttt     420
tctctggcgc tgacactggc attttccgcc aaagagagcg catttaaggc aagtgagatc     480
caaactgatg caggtttttct ggactatcag ataattagct ggaataaaca gcaggtcatc     540
attcatcgtg agaatgagat gtttgctgtg cactggcaga taaaagaaaa gatagtcata     600
acgctgtgcc aacacgatta a                                                621

<210> SEQ ID NO 26
<211> LENGTH: 206
<212> TYPE: PRT
<213> ORGANISM: Escherichia coli

<400> SEQUENCE: 26

Met Lys Thr Thr His Thr Ser Leu Pro Phe Ala Gly His Thr Leu His
1               5                   10                  15

Phe Val Glu Phe Asp Pro Ala Asn Phe Cys Glu Gln Asp Leu Leu Trp
                20                  25                  30

Leu Pro His Tyr Ala Gln Leu Gln His Ala Gly Arg Lys Arg Lys Thr
            35                  40                  45

Glu His Leu Ala Gly Arg Ile Ala Ala Val Tyr Ala Leu Arg Glu Tyr
        50                  55                  60

Gly Tyr Lys Cys Val Pro Ala Ile Gly Glu Leu Arg Gln Pro Val Trp
65                  70                  75                  80

Pro Ala Glu Val Tyr Gly Ser Ile Ser His Cys Gly Thr Thr Ala Leu
                85                  90                  95

Ala Val Val Ser Arg Gln Pro Ile Gly Ile Asp Ile Glu Glu Ile Phe
            100                 105                 110

Ser Val Gln Thr Ala Arg Glu Leu Thr Asp Asn Ile Ile Thr Pro Ala
        115                 120                 125

Glu His Glu Arg Leu Ala Asp Cys Gly Leu Ala Phe Ser Leu Ala Leu
    130                 135                 140

Thr Leu Ala Phe Ser Ala Lys Glu Ser Ala Phe Lys Ala Ser Glu Ile
145                 150                 155                 160

Gln Thr Asp Ala Gly Phe Leu Asp Tyr Gln Ile Ile Ser Trp Asn Lys
                165                 170                 175

Gln Gln Val Ile Ile His Arg Glu Asn Glu Met Phe Ala Val His Trp
            180                 185                 190

Gln Ile Lys Glu Lys Ile Val Ile Thr Leu Cys Gln His Asp
        195                 200                 205
```

<210> SEQ ID NO 27
<211> LENGTH: 141
<212> TYPE: PRT
<213> ORGANISM: Clostridium acetobutylicum

<400> SEQUENCE: 27

Met Ser Leu Ser Ile Glu Gln Ile Met Glu Ile Ile Pro His Arg Tyr
1               5                   10                  15

Pro Met Leu Leu Val Asp Arg Val Glu Glu Ile Glu Pro Gly Lys Arg
            20                  25                  30

Ala Val Gly Tyr Lys Asn Val Thr Phe Asn Glu Gln Ile Phe Gln Gly
        35                  40                  45

His Tyr Pro Gly Lys Pro Ile Met Pro Gly Val Leu Met Ile Glu Ala
    50                  55                  60

Leu Ala Gln Leu Gly Gly Val Ala Ile Leu Ser Leu Asp Lys Tyr Lys
65                  70                  75                  80

Gly Lys Lys Pro Ile Leu Gly Ala Val Lys Asn Ala Lys Phe Arg Arg
                85                  90                  95

Met Val Val Pro Gly Asp Val Leu Lys Leu Glu Ile Glu Ile Val Lys
            100                 105                 110

Val Lys Gly Pro Ala Gly Ile Gly Lys Gly Ile Ala Thr Val Asn Gly
        115                 120                 125

Glu Lys Ala Val Glu Ala Glu Ile Thr Phe Met Ile Val
    130                 135                 140

<210> SEQ ID NO 28
<211> LENGTH: 155
<212> TYPE: PRT
<213> ORGANISM: Synechococcus elongatus

<400> SEQUENCE: 28

Met Thr Val Asn Pro Asp Ala Pro Ala Leu Pro Thr Leu Pro Leu Ala
1               5                   10                  15

Val Glu Thr Ile Gln Gly Leu Leu Pro His Arg Tyr Pro Phe Ala Leu
            20                  25                  30

Val Asp Arg Ile Ile Asp Tyr Val Pro Gly Glu Arg Ala Val Gly Ile
        35                  40                  45

Lys Asn Val Thr Phe Asn Glu Pro Gln Phe Gln Gly His Phe Pro Gly
    50                  55                  60

Arg Pro Leu Met Pro Gly Val Leu Ile Val Glu Ala Met Ala Gln Val
65                  70                  75                  80

Gly Gly Val Ile Val Thr Leu Met Pro Asp Met Pro Gln Gly Leu Phe
                85                  90                  95

Val Phe Ala Gly Ile Asp Gln Val Arg Phe Arg Arg Pro Val Val Pro
            100                 105                 110

Gly Asp Gln Leu Val Leu Ser Ala Gln Leu Leu Ser Val Lys Arg Arg
        115                 120                 125

Arg Phe Cys Lys Ile Gln Gly Glu Ala Met Val Asp Gly Gln Leu Ala
    130                 135                 140

Ala Ser Gly Glu Leu Leu Phe Ser Leu Val Glu
145                 150                 155

<210> SEQ ID NO 29
<211> LENGTH: 558
<212> TYPE: PRT
<213> ORGANISM: Pseudomonas oleovorans -continued

<400> SEQUENCE: 29

```
Met Tyr Asp Tyr Ile Ile Val Gly Ala Gly Ser Ala Gly Cys Val Leu
1               5                   10                  15

Ala Asn Arg Leu Ser Ala Asp Pro Ser Lys Arg Val Cys Leu Leu Glu
            20                  25                  30

Ala Gly Pro Arg Asp Thr Asn Pro Leu Ile His Met Pro Leu Gly Ile
        35                  40                  45

Ala Leu Leu Ser Asn Ser Lys Lys Leu Asn Trp Ala Phe Gln Thr Ala
    50                  55                  60

Pro Gln Gln Asn Leu Asn Gly Arg Ser Leu Phe Trp Pro Arg Gly Lys
65                  70                  75                  80

Thr Leu Gly Gly Ser Ser Ser Ile Asn Ala Met Val Tyr Ile Arg Gly
                85                  90                  95

His Glu Asp Asp Tyr His Ala Trp Glu Gln Ala Ala Gly Arg Tyr Trp
            100                 105                 110

Gly Trp Tyr Arg Ala Leu Glu Leu Phe Lys Arg Leu Glu Cys Asn Gln
            115                 120                 125

Arg Phe Asp Lys Ser Glu His His Gly Val Asp Gly Glu Leu Ala Val
    130                 135                 140

Ser Asp Leu Lys Tyr Ile Asn Pro Leu Ser Lys Ala Phe Val Gln Ala
145                 150                 155                 160

Gly Met Glu Ala Asn Ile Asn Phe Asn Gly Asp Phe Asn Gly Glu Tyr
                165                 170                 175

Gln Asp Gly Val Gly Phe Tyr Gln Val Thr Gln Lys Asn Gly Gln Arg
            180                 185                 190

Trp Ser Ser Ala Arg Ala Phe Leu His Gly Val Leu Ser Arg Pro Asn
            195                 200                 205

Leu Asp Ile Ile Thr Asp Ala His Ala Ser Lys Ile Leu Phe Glu Asp
    210                 215                 220

Arg Lys Ala Val Gly Val Ser Tyr Ile Lys Lys Asn Met His His Gln
225                 230                 235                 240

Val Lys Thr Thr Ser Gly Gly Glu Val Leu Leu Ser Leu Gly Ala Val
                245                 250                 255

Gly Thr Pro His Leu Leu Met Leu Ser Gly Val Gly Ala Ala Ala Glu
            260                 265                 270

Leu Lys Glu His Gly Val Ser Leu Val His Asp Leu Pro Glu Val Gly
            275                 280                 285

Lys Asn Leu Gln Asp His Leu Asp Ile Thr Leu Met Cys Ala Ala Asn
    290                 295                 300

Ser Arg Glu Pro Ile Gly Val Ala Leu Ser Phe Ile Pro Arg Gly Val
305                 310                 315                 320

Ser Gly Leu Phe Ser Tyr Val Phe Lys Arg Glu Gly Phe Leu Thr Ser
                325                 330                 335

Asn Val Ala Glu Ser Gly Gly Phe Val Lys Ser Ser Pro Asp Arg Asp
            340                 345                 350

Arg Pro Asn Leu Gln Phe His Phe Leu Pro Thr Tyr Leu Lys Asp His
            355                 360                 365

Gly Arg Lys Ile Ala Gly Gly Tyr Gly Tyr Thr Leu His Ile Cys Asp
        370                 375                 380

Leu Leu Pro Lys Ser Arg Gly Arg Ile Gly Leu Lys Ser Ala Asn Pro
385                 390                 395                 400

Leu Gln Pro Pro Leu Ile Asp Pro Asn Tyr Leu Ser Asp His Glu Asp
```

-continued

```
                     405                 410                 415

Ile Lys Thr Met Ile Ala Gly Ile Lys Ile Gly Arg Ala Ile Leu Gln
             420                 425                 430

Ala Pro Ser Met Ala Lys His Phe Lys His Glu Val Val Pro Gly Gln
             435                 440                 445

Ala Val Lys Thr Asp Asp Glu Ile Ile Glu Asp Ile Arg Arg Arg Ala
         450                 455                 460

Glu Thr Ile Tyr His Pro Val Gly Thr Cys Arg Met Gly Lys Asp Pro
465                 470                 475                 480

Ala Ser Val Val Asp Pro Cys Leu Lys Ile Arg Gly Leu Ala Asn Ile
             485                 490                 495

Arg Val Val Asp Ala Ser Ile Met Pro His Leu Val Ala Gly Asn Thr
             500                 505                 510

Asn Ala Pro Thr Ile Met Ile Ala Glu Asn Ala Ala Glu Ile Ile Met
             515                 520                 525

Arg Asn Leu Asp Val Glu Ala Leu Glu Ala Ser Ala Glu Phe Ala Arg
         530                 535                 540

Glu Gly Ala Glu Leu Glu Leu Ala Met Ile Ala Val Cys Met
545                 550                 555

<210> SEQ ID NO 30
<211> LENGTH: 503
<212> TYPE: PRT
<213> ORGANISM: Acinetobacter baylyi

<400> SEQUENCE: 30

Met Arg Tyr Ile Asp Pro Asn Gln Pro Gly Ser Lys Val Gln Phe Lys
1               5                   10                  15

Ala Gln Tyr Glu Asn Phe Ile Gly Gly Gln Trp Val Pro Pro Val Lys
             20                  25                  30

Gly Glu Tyr Phe Gly Asn Ser Ser Pro Val Asp Gly Lys Val Phe Thr
         35                  40                  45

Gln Ile Pro Arg Ser Ser Val Glu Asp Ile Glu Leu Ala Leu Asp Ala
     50                  55                  60

Ala His Lys Ala Lys Ala Asp Trp Asn Lys Ala Ser Pro Thr Val Arg
65                  70                  75                  80

Ser Asn Val Leu Leu Lys Ile Ala Asp Arg Leu Glu Glu Asn Leu Glu
             85                  90                  95

Leu Leu Ala Val Ala Glu Thr Trp Glu Asn Gly Lys Pro Ile Arg Glu
             100                 105                 110

Thr Leu Ala Ala Asp Ile Pro Leu Ala Ile Asp His Phe Arg Tyr Phe
         115                 120                 125

Ala Gly Cys Ile Arg Ala Gln Glu Gly Gly Ile Ser Glu Ile Asp Glu
         130                 135                 140

Asp Thr Ile Ala Tyr His Phe His Glu Pro Leu Gly Val Val Gly Gln
145                 150                 155                 160

Ile Ile Pro Trp Asn Phe Pro Ile Leu Met Ala Ala Trp Lys Leu Ala
             165                 170                 175

Pro Ala Leu Ala Ala Gly Asn Cys Ile Val Leu Lys Pro Ala Glu Gln
             180                 185                 190

Thr Pro Ser Ser Ile Leu Val Leu Ala Glu Leu Ile Gln Asp Leu Leu
         195                 200                 205

Pro Pro Gly Val Leu Asn Ile Val Asn Gly Tyr Gly Ala Glu Val Gly
     210                 215                 220
```

-continued

```
Arg Pro Leu Ala Thr Asn Pro Arg Ile Ser Lys Ile Ala Phe Thr Gly
225                 230                 235                 240

Ser Thr Lys Val Gly Gln Met Ile Met Gln Tyr Ala Thr Glu Asn Ile
                245                 250                 255

Ile Pro Val Thr Leu Glu Leu Gly Gly Lys Ser Pro Asn Ile Phe Phe
                260                 265                 270

Glu Asp Ile Leu Asp Lys Glu Asp Asp Tyr Leu Glu Lys Thr Leu Glu
                275                 280                 285

Gly Phe Ala Met Phe Ala Leu Asn Gln Gly Glu Val Cys Thr Cys Pro
                290                 295                 300

Ser Arg Ala Leu Val Gln Glu Ser Ile Ala Asp Lys Phe Leu Glu Met
305                 310                 315                 320

Ala Val Glu Arg Val Lys Arg Ile Lys Thr Gly His Pro Leu Asp Thr
                325                 330                 335

Glu Thr Met Ile Gly Ala Gln Ala Ser Lys Gln Gln Phe Asp Lys Ile
                340                 345                 350

Leu Gly Cys Ile Asp Thr Gly Arg Asn Glu Gly Ala Gln Leu Leu Thr
                355                 360                 365

Gly Gly Asp Ala Arg His Asp Val Asp Gly Gly Phe Tyr Ile Glu Pro
                370                 375                 380

Thr Ile Phe Lys Gly Asn Asn Ser Met Lys Ile Phe Gln Glu Glu Ile
385                 390                 395                 400

Phe Gly Pro Val Leu Ser Val Thr Thr Phe Lys Asp Phe Asp Asp Ala
                405                 410                 415

Met Arg Ile Ala Asn Asp Thr Ile Tyr Gly Leu Gly Ala Gly Val Trp
                420                 425                 430

Ser Arg Ser Ala His Thr Ser Tyr Arg Ala Gly Arg Ala Ile Glu Ala
                435                 440                 445

Gly Arg Val Trp Thr Asn Cys Tyr His Leu Tyr Pro Ala His Ala Ala
                450                 455                 460

Phe Gly Gly Tyr Lys Gln Ser Gly Ile Gly Arg Glu Asn His Arg Met
465                 470                 475                 480

Met Leu Asp His Tyr Gln Gln Thr Lys Asn Leu Leu Val Ser Tyr Ser
                485                 490                 495

Thr Lys Pro Met Gly Phe Phe
                500
```

```
<210> SEQ ID NO 31
<211> LENGTH: 506
<212> TYPE: PRT
<213> ORGANISM: Marinobacter aquaeoli

<400> SEQUENCE: 31
```

```
Met Ile Tyr Ala Gln Pro Gly Gln Glu Gly Ser Val Val Ser Phe Lys
1                   5                   10                  15

Ser Arg Tyr Glu Asn Tyr Ile Gly Gly Glu Trp Val Ala Pro Val Lys
                20                  25                  30

Gly Gln Tyr Phe Asp Asn Ile Thr Pro Val Thr Gly Ala Val Phe Cys
                35                  40                  45

Glu Val Pro Arg Ser Thr Ala Glu Asp Ile Asp Leu Ala Leu Asp Ala
                50                  55                  60

Ala His Lys Ala Ala Pro Ala Trp Gly Lys Thr Ser Pro Thr Glu Arg
65                  70                  75                  80

Ser Asn Ile Leu Leu Lys Ile Ala Asp Arg Ile Glu Ala Asn Leu Glu
                85                  90                  95
```

```
Lys Leu Ala Val Ala Glu Thr Trp Asp Asn Gly Lys Ala Val Arg Glu
            100                 105                 110

Thr Leu Asn Ala Asp Val Pro Leu Ala Ala Asp His Leu Arg Tyr Phe
            115                 120                 125

Ala Gly Cys Ile Arg Ala Gln Glu Gly His Met Ser Glu Ile Asp His
            130                 135                 140

Asn Thr Val Ala Tyr His Phe His Glu Pro Leu Gly Val Val Gly Gln
        145                 150                 155                 160

Ile Ile Pro Trp Asn Phe Pro Leu Leu Met Ala Ala Trp Lys Leu Gly
                165                 170                 175

Pro Cys Leu Ala Ser Gly Asn Cys Thr Val Leu Lys Pro Ala Glu Gln
            180                 185                 190

Thr Pro Ala Ser Ile Leu Val Leu Met Asp Ile Ile Gly Asp Leu Leu
            195                 200                 205

Pro Pro Gly Val Ile Asn Ile Val Asn Gly Tyr Gly Ile Glu Ala Gly
            210                 215                 220

Gln Ala Leu Ala Thr Ser Lys Arg Ile Ala Lys Ile Ala Phe Thr Gly
225                 230                 235                 240

Ser Thr Pro Val Gly Ser His Ile Leu Lys Cys Ala Ala Glu Asn Ile
                245                 250                 255

Ile Pro Ser Thr Val Glu Leu Gly Gly Lys Ser Pro Asn Ile Tyr Phe
                260                 265                 270

Ser Asp Val Met Lys Ala Glu Pro Glu Phe Val Asp Lys Cys Val Glu
            275                 280                 285

Gly Leu Val Leu Ala Phe Phe Asn Gln Gly Glu Ile Cys Thr Cys Pro
            290                 295                 300

Ser Arg Ala Leu Val Gln Glu Asp Met Phe Glu Glu Phe Met Gln Lys
305                 310                 315                 320

Val Val Glu Arg Thr Lys Ser Ile Lys Arg Gly Asn Pro Leu Asp Thr
                325                 330                 335

Asp Val Gln Val Gly Ala Gln Ala Ser Lys Glu Gln Phe Asp Lys Ile
            340                 345                 350

Met Ser Tyr Met Glu Ile Gly Arg Gln Glu Gly Ala Val Val Leu Thr
            355                 360                 365

Gly Gly Asp Arg Glu His Leu Glu Gly Glu Phe Asn Asn Gly Phe Tyr
        370                 375                 380

Ile Gln Pro Thr Leu Phe Lys Gly Asp Asn Lys Met Arg Val Phe Gln
385                 390                 395                 400

Glu Glu Ile Phe Gly Pro Val Val Gly Val Thr Thr Phe Lys Thr Glu
            405                 410                 415

Glu Glu Ala Leu Ala Ile Ala Asn Asp Thr Glu Phe Gly Leu Gly Ala
            420                 425                 430

Gly Val Trp Thr Arg Asp Thr Asn Leu Ala Tyr Arg Met Gly Arg Asn
            435                 440                 445

Ile Gln Ala Gly Arg Val Trp Met Asn Cys Tyr His Ala Tyr Pro Ala
            450                 455                 460

His Ala Ala Phe Gly Gly Tyr Lys Lys Ser Gly Ile Gly Arg Glu Asn
465                 470                 475                 480

His Lys Met Ala Leu Glu His Tyr Gln Gln Thr Lys Cys Met Leu Thr
                485                 490                 495

Ser Tyr Asp Thr Asn Pro Leu Gly Phe Phe
            500                 505
```

<210> SEQ ID NO 32
<211> LENGTH: 483
<212> TYPE: PRT
<213> ORGANISM: Pseudomonas oleovorans

<400> SEQUENCE: 32

```
Met Thr Ile Pro Ile Ser Leu Ala Lys Leu Asn Ser Ser Ala Asp Thr
1               5                   10                  15

His Ser Ala Leu Glu Val Phe Asn Leu Gln Lys Val Ala Ser Ser Ala
            20                  25                  30

Arg Arg Gly Lys Phe Gly Ile Ala Glu Arg Ile Ala Ala Leu Asn Leu
        35                  40                  45

Leu Lys Glu Thr Ile Gln Arg Arg Glu Pro Glu Ile Ile Ala Ala Leu
    50                  55                  60

Ala Ala Asp Phe Arg Lys Pro Ala Ser Glu Val Lys Leu Thr Glu Ile
65                  70                  75                  80

Phe Pro Val Leu Gln Glu Ile Asn His Ala Lys Arg Asn Leu Lys Asp
                85                  90                  95

Trp Met Lys Pro Arg Arg Val Arg Ala Ala Leu Ser Val Ala Gly Thr
            100                 105                 110

Arg Ala Gly Leu Arg Tyr Glu Pro Lys Gly Val Cys Leu Ile Ile Ala
        115                 120                 125

Pro Trp Asn Tyr Pro Phe Asn Leu Ser Phe Gly Pro Leu Val Ser Ala
        130                 135                 140

Leu Ala Ala Gly Asn Ser Val Val Ile Lys Pro Ser Glu Leu Thr Pro
145                 150                 155                 160

His Thr Ala Thr Leu Ile Gly Ser Ile Val Arg Glu Ala Phe Ser Val
                165                 170                 175

Asp Leu Val Ala Val Val Glu Gly Asp Ala Ala Val Ser Gln Glu Leu
            180                 185                 190

Leu Ala Leu Pro Phe Asp His Ile Phe Phe Thr Gly Ser Pro Arg Val
            195                 200                 205

Gly Lys Leu Val Met Glu Ala Ala Ser Lys Thr Leu Ala Ser Val Thr
        210                 215                 220

Leu Glu Leu Gly Gly Lys Ser Pro Thr Ile Ile Gly Pro Thr Ala Asn
225                 230                 235                 240

Leu Pro Lys Ala Ala Arg Asn Ile Val Trp Gly Lys Phe Ser Asn Asn
                245                 250                 255

Gly Gln Thr Cys Ile Ala Pro Asp His Val Phe Val His Arg Cys Ile
            260                 265                 270

Ala Gln Lys Phe Asn Glu Ile Leu Val Lys Glu Ile Val Arg Val Tyr
        275                 280                 285

Gly Lys Asp Phe Ala Ala Gln Arg Arg Ser Ala Asp Tyr Cys Arg Ile
        290                 295                 300

Val Asn Asp Gln His Phe Asn Arg Ile Asn Lys Leu Leu Thr Asp Ala
305                 310                 315                 320

Lys Ala Lys Gly Ala Lys Ile Leu Gln Gly Gly Gln Val Asp Ala Thr
                325                 330                 335

Glu Arg Leu Val Val Pro Thr Val Leu Ser Asn Val Thr Ala Ala Met
            340                 345                 350

Asp Ile Asn His Glu Glu Ile Phe Gly Pro Leu Leu Pro Ile Ile Glu
        355                 360                 365

Tyr Asp Asp Ile Asp Ser Val Ile Lys Arg Val Asn Asp Gly Asp Lys
        370                 375                 380
```

-continued

Pro Leu Ala Leu Tyr Val Phe Ser Glu Asp Lys Gln Phe Val Asn Asn
385                 390                 395                 400

Ile Val Ala Arg Thr Ser Ser Gly Ser Val Gly Val Asn Leu Ser Val
                405                 410                 415

Val His Phe Leu His Pro Asn Leu Pro Phe Gly Gly Val Asn Asn Ser
            420                 425                 430

Gly Ile Gly Ser Ala His Gly Val Tyr Gly Phe Arg Ala Phe Ser His
        435                 440                 445

Glu Lys Pro Val Leu Ile Asp Lys Phe Ser Ile Thr His Trp Leu Phe
        450                 455                 460

Pro Pro Tyr Thr Lys Lys Val Lys Gln Leu Ile Gly Ile Thr Val Lys
465                 470                 475                 480

Tyr Leu Ser

<210> SEQ ID NO 33
<211> LENGTH: 406
<212> TYPE: PRT
<213> ORGANISM: Escherichia coli

<400> SEQUENCE: 33

Met Lys Arg Ala Val Ile Thr Gly Leu Gly Ile Val Ser Ser Ile Gly
1               5                   10                  15

Asn Asn Gln Gln Glu Val Leu Ala Ser Leu Arg Glu Gly Arg Ser Gly
            20                  25                  30

Ile Thr Phe Ser Gln Glu Leu Lys Asp Ser Gly Met Arg Ser His Val
        35                  40                  45

Trp Gly Asn Val Lys Leu Asp Thr Thr Gly Leu Ile Asp Arg Lys Val
        50                  55                  60

Val Arg Phe Met Ser Asp Ala Ser Ile Tyr Ala Phe Leu Ser Met Glu
65                  70                  75                  80

Gln Ala Ile Ala Asp Ala Gly Leu Ser Pro Glu Ala Tyr Gln Asn Asn
                85                  90                  95

Pro Arg Val Gly Leu Ile Ala Gly Ser Gly Gly Gly Ser Pro Arg Phe
            100                 105                 110

Gln Val Phe Gly Ala Asp Ala Met Arg Gly Pro Arg Gly Leu Lys Ala
        115                 120                 125

Val Gly Pro Tyr Val Val Thr Lys Ala Met Ala Ser Gly Val Ser Ala
        130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175

Ile Gln Leu Gly Lys Gln Asp Ile Val Phe Ala Gly Gly Gly Glu Glu
            180                 185                 190

Leu Cys Trp Glu Met Ala Cys Glu Phe Asp Ala Met Gly Ala Leu Ser
        195                 200                 205

Thr Lys Tyr Asn Asp Thr Pro Glu Lys Ala Ser Arg Thr Tyr Asp Ala
        210                 215                 220

His Arg Asp Gly Phe Val Ile Ala Gly Gly Gly Met Val Val Val
225                 230                 235                 240

Glu Glu Leu Glu His Ala Leu Ala Arg Gly Ala His Ile Tyr Ala Glu
            245                 250                 255

Ile Val Gly Tyr Gly Ala Thr Ser Asp Gly Ala Asp Met Val Ala Pro
        260                 265                 270

```
Ser Gly Glu Gly Ala Val Arg Cys Met Lys Met Ala Met His Gly Val
        275                 280                 285

Asp Thr Pro Ile Asp Tyr Leu Asn Ser His Gly Thr Ser Thr Pro Val
        290                 295                 300

Gly Asp Val Lys Glu Leu Ala Ala Ile Arg Glu Val Phe Gly Asp Lys
305                 310                 315                 320

Ser Pro Ala Ile Ser Ala Thr Lys Ala Met Thr Gly His Ser Leu Gly
                325                 330                 335

Ala Ala Gly Val Gln Glu Ala Ile Tyr Ser Leu Leu Met Leu Glu His
                340                 345                 350

Gly Phe Ile Ala Pro Ser Ile Asn Ile Glu Glu Leu Asp Glu Gln Ala
        355                 360                 365

Ala Gly Leu Asn Ile Val Thr Glu Thr Thr Asp Arg Glu Leu Thr Thr
        370                 375                 380

Val Met Ser Asn Ser Phe Gly Phe Gly Gly Thr Asn Ala Thr Leu Val
385                 390                 395                 400

Met Arg Lys Leu Lys Asp
                405
```

```
<210> SEQ ID NO 34
<211> LENGTH: 1026
<212> TYPE: DNA
<213> ORGANISM: Synechococcus elongatus

<400> SEQUENCE: 34
atgttcggtc ttatcggtca tctcaccagt ttggagcagg cccgcgacgt ttctcgcagg      60
atgggctacg acgaatacgc cgatcaagga ttggagtttt ggagtagcgc tcctcctcaa     120
atcgttgatg aaatcacagt caccagtgcc acaggcaagg tgattcacgg tcgctacatc     180
gaatcgtgtt tcttgccgga aatgctggcg gcgcgccgct tcaaaacagc cacgcgcaaa     240
gttctcaatg ccatgtccca tgcccaaaaa cacggcatcg acatctcggc cttggggggc     300
tttacctcga ttattttcga gaatttcgat ttggccagtt tgcggcaagt gcgcgacact     360
accttggagt ttgaacggtt caccaccggc aatactcaca cggcctacgt aatctgtaga     420
caggtggaag ccgctgctaa aacgctgggc atcgacatta cccaagcgac agtagcggtt     480
gtcggcgcga ctggcgatat cggtagcgct gtctgccgct ggctcgacct caaactgggt     540
gtcggtgatt tgatcctgac ggcgcgcaat caggagcgtt tggataacct gcaggctgaa     600
ctcggccggg gcaagattct gcccttggaa gccgctctgc cggaagctga ctttatcgtg     660
tgggtcgcca gtatgcctca gggcgtagtg atcgacccag caaccctgaa gcaaccctgc     720
gtcctaatcg acgggggcta ccccaaaaac ttgggcagca aagtccaagg tgagggcatc     780
tatgtcctca atggcggggt agttgaacat tgcttcgaca tcgactggca gatcatgtcc     840
gctgcagaga tggcgcggcc cgagcgccag atgtttgcct gctttgccga ggcgatgctc     900
ttggaatttg aaggctggca tactaacttc tcctggggcc gcaaccaaat cacgatcgag     960
aagatggaag cgatcggtga ggcatcggtg cgccacggct tccaacccctt ggcattggca    1020 atttga                                                             1026
```

```
<210> SEQ ID NO 35
<211> LENGTH: 341
<212> TYPE: PRT
<213> ORGANISM: Synechococcus elongatus

<400> SEQUENCE: 35
```

-continued

```
Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
                20                  25                  30

Phe Trp Ser Ser Ala Pro Pro Gln Ile Val Asp Glu Ile Thr Val Thr
            35                  40                  45

Ser Ala Thr Gly Lys Val Ile His Gly Arg Tyr Ile Glu Ser Cys Phe
        50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
            115                 120                 125

Thr Gly Asn Thr His Thr Ala Tyr Val Ile Cys Arg Gln Val Glu Ala
        130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
            165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
            195                 200                 205

Leu Glu Ala Ala Leu Pro Glu Ala Asp Phe Ile Val Trp Val Ala Ser
        210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
            245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
            275                 280                 285

Arg Gln Met Phe Ala Cys Phe Ala Glu Ala Met Leu Leu Glu Phe Glu
            290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
                340
```